US008617813B2

(12) United States Patent
Ko et al.

(10) Patent No.: US 8,617,813 B2
(45) Date of Patent: Dec. 31, 2013

(54) METHODS FOR MODULATING EMBRYONIC STEM CELL DIFFERENTIATION

(75) Inventors: Minoru S. H. Ko, Cockeysville, MD (US); Geppino Falco, Rotondi (IT); Sung-Lim Lee, Gyeongsan (KR); Manuela Monti, Baltimore, MD (US); Ilaria Stanghellini, Baltimore, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/332,800

(22) Filed: Dec. 21, 2011

(65) Prior Publication Data
US 2012/0129161 A1    May 24, 2012

Related U.S. Application Data

(62) Division of application No. 12/529,004, filed as application No. PCT/US2008/058261 on Mar. 26, 2008, now abandoned.

(60) Provisional application No. 60/920,215, filed on Mar. 26, 2007.

(51) Int. Cl.
*C12Q 1/68* (2006.01)
*C12N 15/85* (2006.01)
*C12N 5/10* (2006.01)

(52) U.S. Cl.
USPC .......................... 435/6.1; 435/320.1; 435/325

(58) Field of Classification Search
USPC ........................................ 435/6.1, 320.1, 325
See application file for complete search history.

(56) References Cited

U.S. PATENT DOCUMENTS

| | | | |
|---|---|---|---|
| 5,226,914 A | 7/1993 | Caplan et al. | |
| 5,670,372 A | 9/1997 | Hogan | |
| 5,750,376 A | 5/1998 | Weiss et al. | |
| 6,090,622 A | 7/2000 | Gearhart et al. | |
| 6,200,806 B1 | 3/2001 | Thomson | |
| 6,506,559 B1 | 1/2003 | Fire et al. | |
| 6,943,241 B2 | 9/2005 | Isogai et al. | |
| 2002/0127715 A1* | 9/2002 | Benvenisty et al. | 435/366 |
| 2006/0251642 A1 | 11/2006 | Wolffe et al. | |

FOREIGN PATENT DOCUMENTS

| | | |
|---|---|---|
| JP | 09-500004 | 1/1997 |
| WO | WO 94/24274 | 10/1994 |
| WO | WO 00/27995 | 5/2000 |
| WO | WO 00/70021 | 11/2000 |
| WO | WO/2004/009768 | * 1/2004 |
| WO | WO 2004/067744 | 8/2004 |

OTHER PUBLICATIONS

Romano, Drug News Prospect, 2003, 16(5): 267, 267-276.*
Andrews et al Biochem Soc Trans. 2005; 33(Pt 6):1526-30.*
Koestenbauer et al Am J Reprod Immunol. 2006; 55(3):169-80.*
Zhang et al. (Nucleic Acid Research, 2006, 34(17), 4780-4790.*
Falco et al (PowerPoint presentation from the Annual Meeting of the Society for the Study of Reproduction, Jul. 24-27, 2005) or Abstract from the Annual Meeting of the Society for the Study of Reproduction.*
International Search Report from PCT/US2008/058261, dated Jan. 19, 2009.
Written Opinion of the International Searching Authority from PCT/US2008/058261, dated, Jan. 19, 2009.
Andrews et al., "Embryonic stem (ES) cells and embryonal carcinoma (EC) cells: opposite sides of the same coin," *Biochem Soc Trans* 33(Pt6):1526-1530, 2005.
Database Geneseq [Online], "Viral vector-related plasmid—pcDNA6.2/GFP-DEST." XP002492234 retrieved from EBI accession No. GSN:ADQ48564 Database accession No. ADQ48564, Sep. 9, 2004.
Carter et al., "An in situ hybridization-based screen for heterogeneously expressed genes in mouse ES cells," *Gene Expression Patterns* 8(3):181-198, Nov. 4, 2007.
Chambers et al., "Functional Expression Cloning of Nanog, a Pluripotency Sustaining Factor in Embryonic Stem Cells," *Cell* 113:643-655, 2003.
Dahéron et al., "LIF/STAT3 Signaling Fails to Maintain Self-Renewal of Human Embryonic Stem Cells," *Stem Cells* 22:770-778, 2004.
Edelstein et al., "The SCAN domain family of zinc finger transcription factors," *Gene* 359:1-1, Oct. 10, 2005.
Falco, "Zga1, a 2-cell Specific Gene Required for 2-cell to 4-cell Progression in Mouse Preimplantation Embryos," PowerPoint presentation from the Annual Meeting of the Society for the Study of Reproduction, Jul. 24-27, 2005.
Falco et al., "Identification and Characterization of Zygotic Genomic Activation Gene 1 (Zga1) in Mouse," Abstract from the Annual Meeting of the Society for the Study of Reproduction, Jul. 24-27, 2005.
Falco et al., "Zscan4: A novel gene expressed exclusively in late 2-cell embryos and embryonic stem cells," *Developmental Biology* 307(2):539-550, 2007.

(Continued)

*Primary Examiner* — Anoop Singh
(74) *Attorney, Agent, or Firm* — Klarquist Sparkman, LLP

(57) ABSTRACT

Described herein is Zscan4, a gene exhibiting 2-cell embryonic stage and embryonic stem cell specific expression. Identification of nine Zscan4 co-expressed genes is also described. Inhibition of Zscan4 expression inhibits the 2-cell to 4-cell embryonic transition and prevents blastocyst implantation, expansion and outgrowth. Provided herein are methods of inhibiting differentiation of a stem cell, promoting blastocyst outgrowth of embryonic stem cells and identifying a subpopulation of stem cells expressing Zscan4. Further described is the identification of Trim43 as a gene exhibiting morula-specific expression. Also provided are isolated expression vectors comprising a Zscan4 promoter, or a Trim43 promoter operably linked to a heterologous polypeptide and uses thereof. Further provided are transgenic animals comprising transgenes encoding marker proteins operably linked to Zscan4 and Trim43 promoters.

7 Claims, 16 Drawing Sheets

(56) References Cited

OTHER PUBLICATIONS

Falco et al., "Use of *Chuk* as an internal standard suitable for quantitative RT-PCR in mouse preimplantation embryos," *Reprod Biomed Online* 13(3):397-403, 2006.

Gerhard et al., The status, quality, and expansion of the NIH full-length cDNA project: the Mammalian Gene Collection (MGC), *Genom Res* 14:2121-2127, 2004.

Ginis et al., "Differences between human and mouse embryonic stem cells," *Dev Biol* 269:360-380, 2004.

Humphrey et al., "Maintenance of Pluripotency in Human Embryonic Stem Cells is STAT3 Independent," *Stem Cells* 22:522-530, 2004.

Koestenbauer et al., "Embryonic Stem Cells: Similarities and Differences Between Human and Murine Embryonic Stem Cells," *Am J Reprod Immunol* 55(3):169-180, 2006.

Ota et al., Complete sequencing and characterization of 21,243 full-length human cDNAs, *Nat Genet* 36(1):40-45, 2004.

Romano, "Gene Transfer in Experimental Medicine," *Drug News Prospect* 16(5):267-276, 2003.

Sato et al., "Maintenance of pluripotency in human and mouse embryonic stem cells through activation of Wnt signaling by a pharmacological GSK-3-specific inhibitor," *Nat Med* 10:55-63, 2004.

Sharov et al., Transcriptome analysis of mouse stem cells and early embryos, *PLoS Bio* 1(3):410-419, 2003.

Strausberg et al., Generation and initial analysis of more than 15,000 full-length human and mouse cDNA sequences, *Proc Natl Acad Sci USA* 99(26):16899-16903, 2002.

Thomas et al., "Progress and Problems with the Use of Viral Vectors for Gene Therapy," *Nature Rev Genet* 4:346-358, 2004.

Verma and Weitzman, "Gene Therapy: Twenty-First Century Medicine," *Annu Rev Biochem* 74:711-738, 2005.

Zhang et al., Zfp206 regulates ES cell gene expression and differentiation, *Nucleic Acids Research* 34(17):4780-4790, 2006.

Mitsui et al., "The Homeoprotein Nanog is Required for Maintenance of Pluripotency in Mouse Epiblast and ES Cells," *Cell* 113:631-642, 2003.

\* cited by examiner

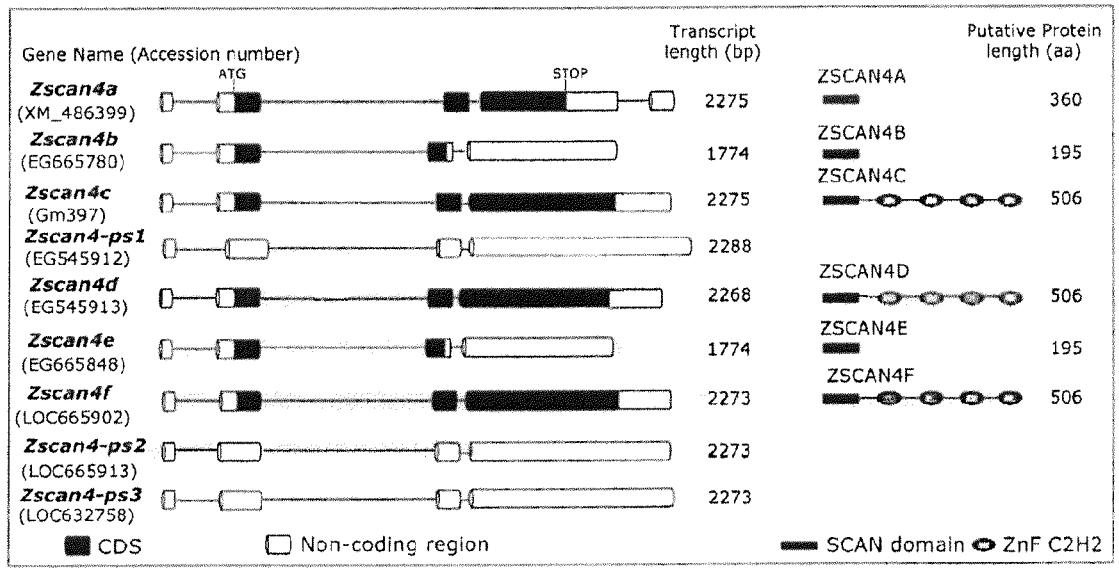

FIG. 3A
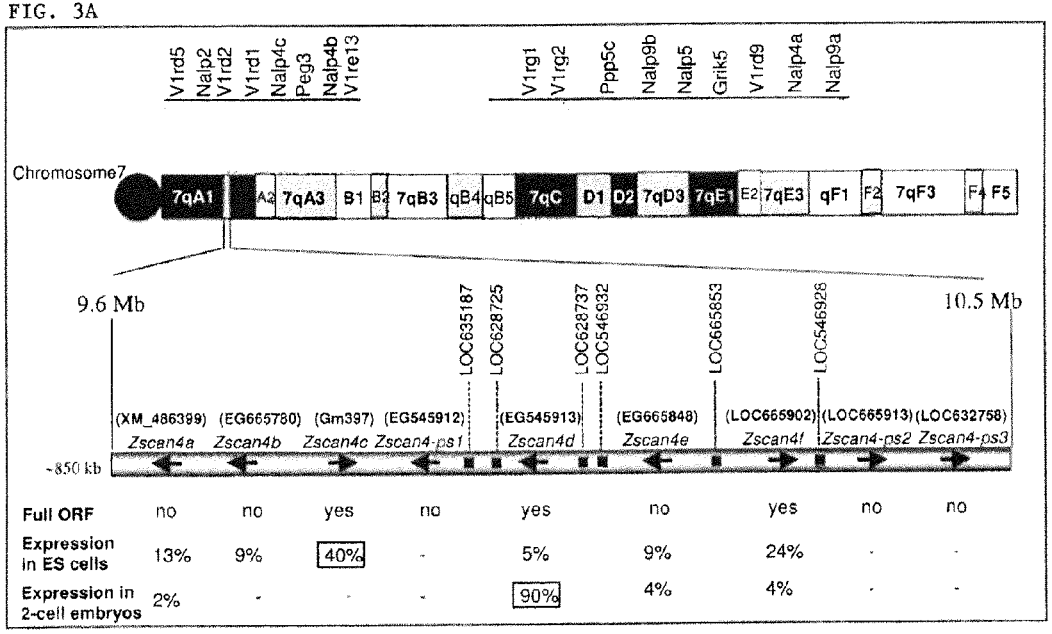
FIG. 3B
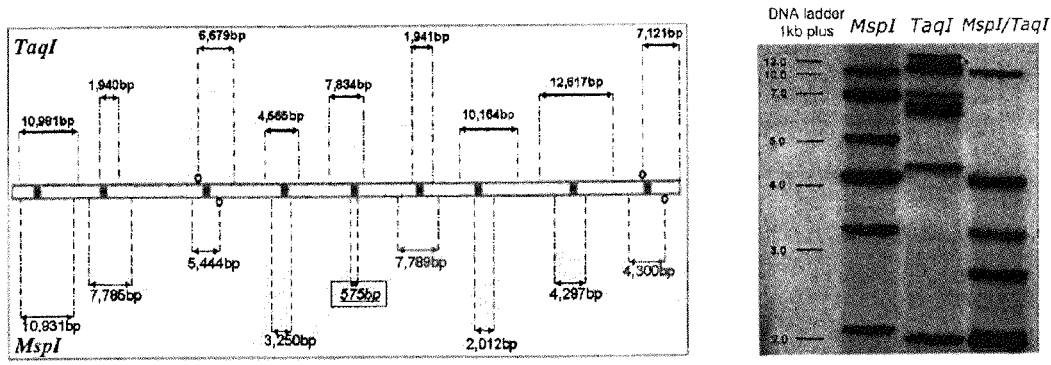
● = Target sequences of the probe used for Southern Blot hybridization
○ = Restriction sites that generate extra bands in double digestion with MspI/TaqI
FIG. 3C

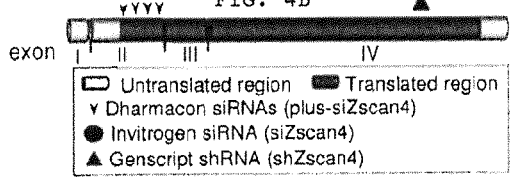
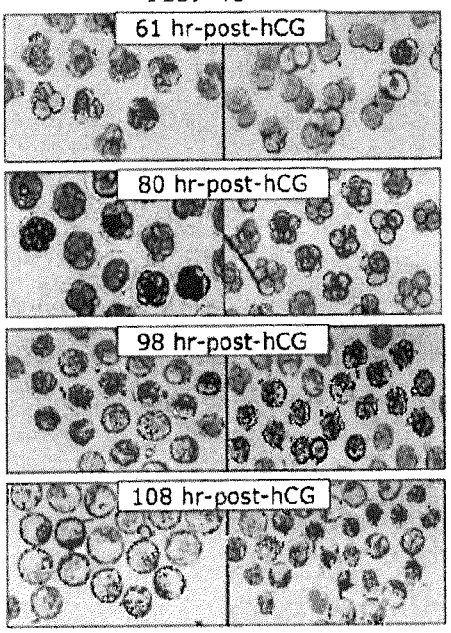
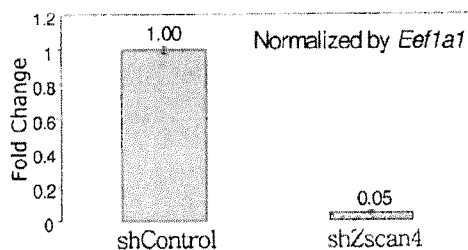
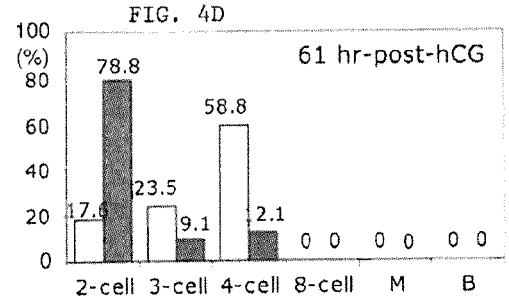
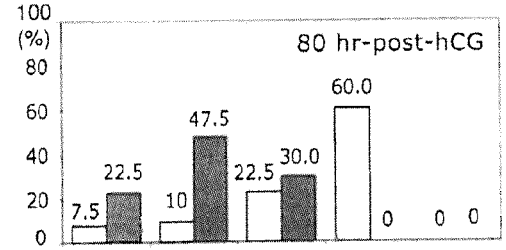
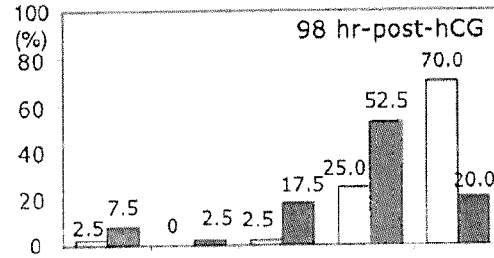
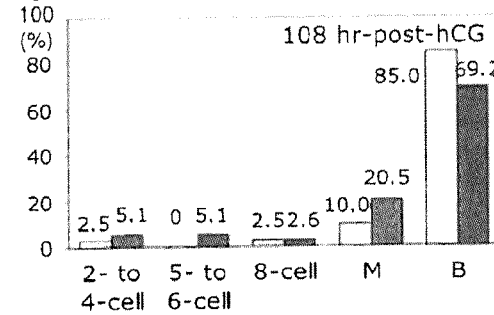

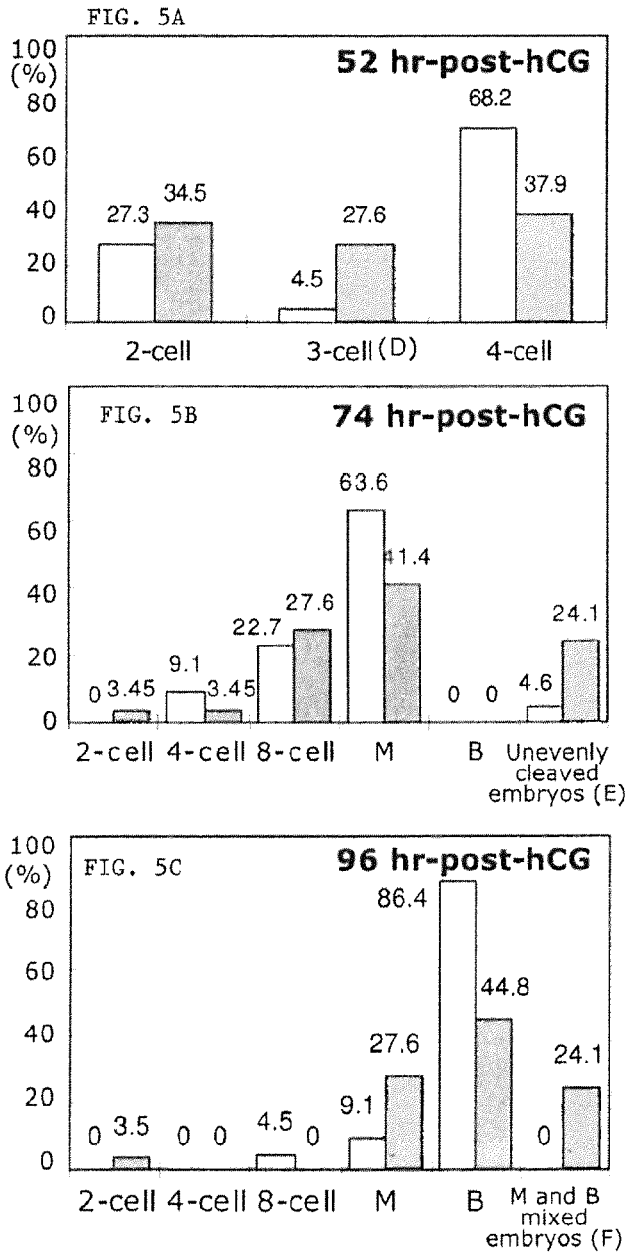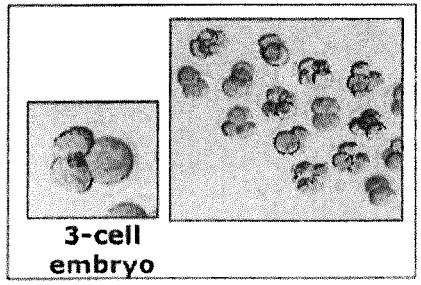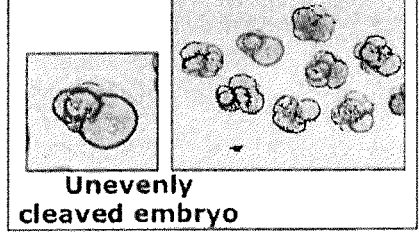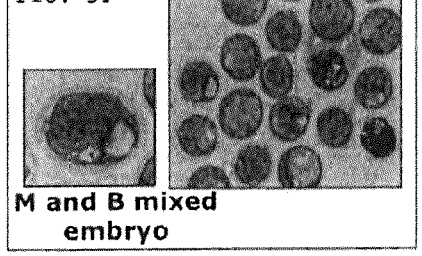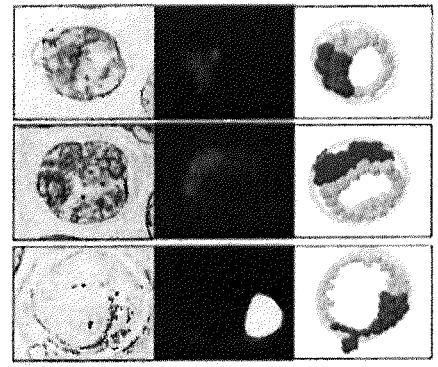

FIG. 6A
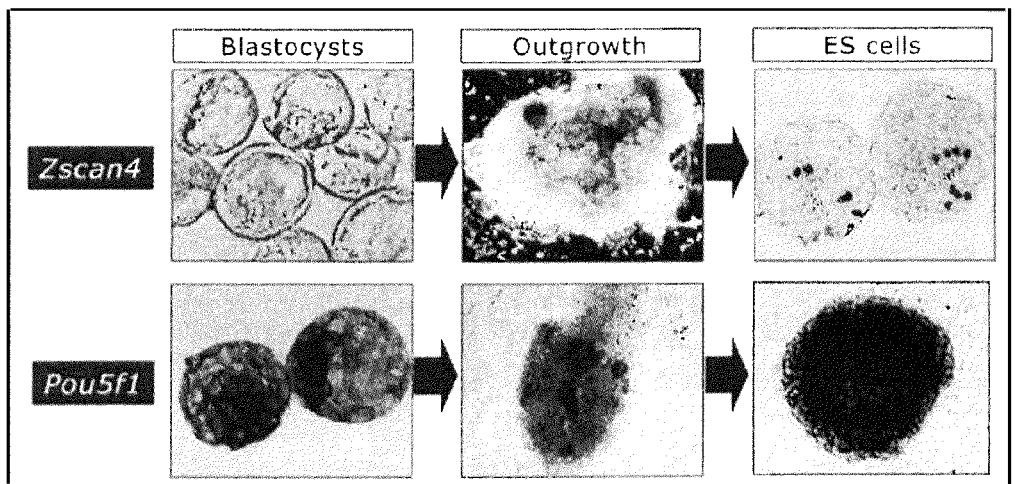
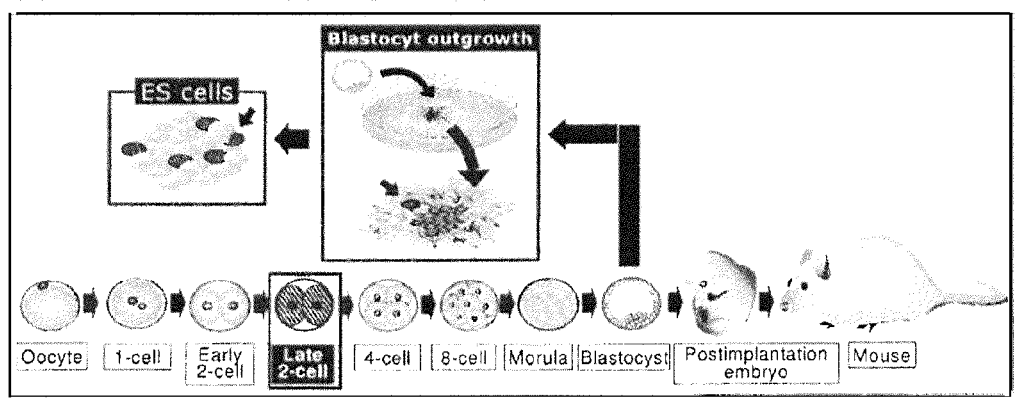
FIG. 6B

FIG. 7A

| cDNA (length) | Human ZSCAN4 (2230bp) | Mouse Zscan4c (2275bp) | Mouse Zscan4d (2268bp) | Mouse Zscan4f (2273bp) |
|---|---|---|---|---|
| ZSCAN4 | - | 54 | 55 | 54 |
| Zscan4c | | - | 97 | 99 |
| Zscan4d | | | - | 97 |
| Zscan4f | | | | - |

FIG. 7B

| CDS (length) | Human ZSCAN4 (1302bp) | Mouse Zscan4c (1518bp) | Mouse Zscan4d (1518bp) | Mouse Zscan4f (1518bp) |
|---|---|---|---|---|
| ZSCAN4 | - | 65 | 66 | 65 |
| Zscan4c | | - | 98 | 99 |
| Zscan4d | | | - | 98 |
| Zscan4f | | | | - |

FIG. 7C

| Protein (length) | Human ZSCAN4 (433aa) | Mouse ZSCAN4C (506aa) | Mouse ZSCAN4D (506aa) | Mouse ZSCAN4F (506aa) |
|---|---|---|---|---|
| ZSCAN4 | - | 45 | 44 | 44 |
| ZSCAN4C | | - | 95 | 99 |
| ZSCAN4D | | | - | 94 |
| ZSCAN4F | | | | - |

FIG. 7D

| SCAN Domain (length) | Human ZSCAN4 (96aa) | Mouse ZSCAN4C (99aa) | Mouse ZSCAN4D (99aa) | Mouse ZSCAN4F (99aa) |
|---|---|---|---|---|
| ZSCAN4 | - | 50 | 50 | 50 |
| ZSCAN4C | | - | 98 | 100 |
| ZSCAN4D | | | - | 98 |
| ZSCAN4F | | | | - |

FIG. 7E

| ZFP Domain (length) | Human ZSCAN4 (107aa) | Mouse ZSCAN4C (109aa) | Mouse ZSCAN4D (109aa) | Mouse ZSCAN4F (109aa) |
|---|---|---|---|---|
| ZSCAN4 | - | 59 | 58 | 59 |
| ZSCAN4C | | - | 99 | 100 |
| ZSCAN4D | | | - | 99 |
| ZSCAN4F | | | | - |

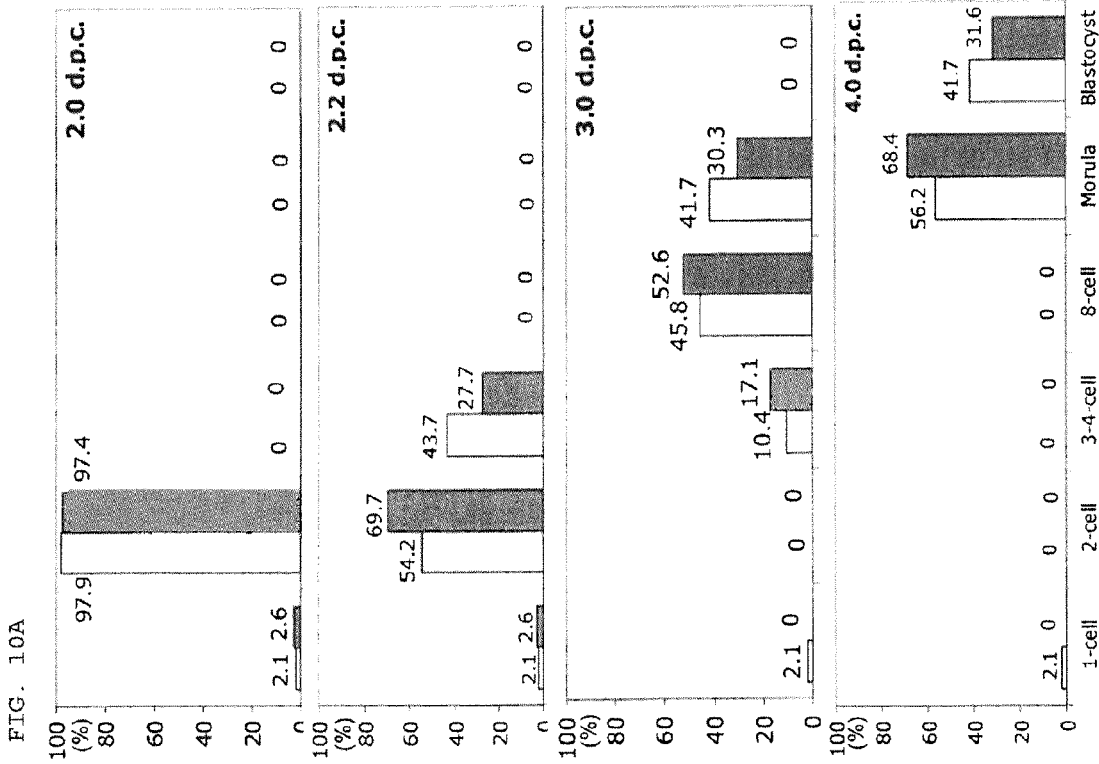

METHODS FOR MODULATING EMBRYONIC STEM CELL DIFFERENTIATION

CROSS REFERENCE TO RELATED APPLICATIONS

This is a divisional of U.S. application Ser. No. 12/529,004, filed Aug. 27, 2009, now abandoned, which is the U.S. National Stage of International Application No. PCT/US2008/058261, filed Mar. 26, 2008, published in English under PCT Article 21(2), which claims the benefit of U.S. Provisional Application No. 60/920,215, filed Mar. 26, 2007. All of the above-referenced applications are herein incorporated by reference in their entirety.

FIELD

This application relates to the field of cellular differentiation, specifically to the methods of identifying and using a subpopulation of stem cells, which can be identified by the expression of Zscan4 or one or more Zscan4 co-expressed genes described herein, and the methods of inhibiting differentiation and prolonging viability by altering Zscan4. This application also relates to the identification of Trim43 as a gene highly expressed at the morula stage.

BACKGROUND

Stem cells have been identified in several somatic tissues including the nervous system, bone marrow, epidermis, skeletal muscle, and liver. This 'set-aside' population of cells is believed to be responsible for maintaining homeostasis within individual tissues in adult animals. The number of stem cells and their decision to differentiate must be tightly controlled during embryonic development and in the adult animal to avoid premature aging or tumor formation. Different somatic stem cells share the properties of self-renewal and multi-developmental potential, suggesting the presence of common cellular machinery.

Embryonic stem (ES) cells can proliferate indefinitely in an undifferentiated state. Furthermore, ES cells are pluripotent cells, meaning that they can generate all of the cells present in the body (bone, muscle, brain cells, etc.). ES cells have been isolated from the inner cell mass of the developing murine blastocyst (Evans et al., *Nature* 292:154-156, 1981; Martin et al., *Proc. Natl. Acad. Sci. U.S.A.* 78:7634-7636, 1981; Robertson et al., *Nature* 323:445-448, 1986; Doetschman et al., *Nature* 330:576-578, 1987; and Thomas et al., *Cell* 51:503-512, 1987; U.S. Pat. No. 5,670,372). Additionally, human cells with ES cell properties have recently been isolated from the inner blastocyst cell mass (Thomson et al., *Science* 282:1145-1147, 1998) and developing germ cells (Shamblott et al., *Proc. Natl. Acad. Sci. U.S.A.* 95:13726-13731, 1998) (see also U.S. Pat. No. 6,090,622, PCT Publication Nos. WO 00/70021 and WO 00/27995).

There is growing interest in the analysis of patterns of gene expression in cells, such as stem cells. However, few studies have identified an individual gene product that functions in the complex network of signals in developing tissues to inhibit differentiation and increase proliferation.

SUMMARY

Described herein is the identification of Zscan4 as a gene specifically expressed during the 2-cell embryonic stage and in embryonic stem cells. Further described herein is the identification of Zscan4 co-expressed genes which exhibit a similar expression pattern as Zscan4 in the developing embryo. Also described herein is the identification of Trim43 as a gene abundantly expressed at the morula stage of embryonic development.

Provided herein are methods of inhibiting differentiation of a stem cell comprising increasing the expression of Zscan4 in the stem cell. In one embodiment, inhibiting differentiation of the stem cell increases viability of the stem cells. In another embodiment, inhibiting differentiation of the stem cell prevents senescence of the stem cell. As described herein, the stem cell can be any type of stem cell, including, but not limited to, an embryonic stem cell, an embryonic germ cell, a germline stem cell or a multipotent adult progenitor cell.

Also provided herein is a method of promoting blastocyst outgrowth of an embryonic stem cell, comprising increasing the expression of Zscan4 in the embryonic stem cell, thereby promoting blastocyst outgrowth of the embryonic stem cell.

Further provided is a method of identifying an undifferentiated subpopulation of stem cells expressing Zscan4, comprising transfecting stem cells with an expression vector comprising a Zscan4 promoter and a reporter gene, wherein expression of the reporter gene indicates Zscan4 is expressed in the subpopulation of stem cells. In one embodiment, the promoter is a Zscan4c promoter.

An isolated expression vector comprising a Zscan4 promoter operably linked to a heterologous polypeptide is also provided. In one embodiment, the Zscan4 promoter is a Zscan4c promoter. In another embodiment, the heterologous polypeptide is a marker, enzyme or fluorescent protein. Also provided is an expression vector comprising a Trim43 promoter operably linked to a heterologous polypeptide. In some embodiments, the Trim43 promoter comprises at least a portion of the nucleic acid sequence set forth as SEQ ID NO: 31. Isolated embryonic stem cells comprising the expression vectors described herein are also provided.

Also provided is a method of identifying an undifferentiated subpopulation of stem cells, wherein the stem cells express Zscan4, comprising detecting expression of one or more of AF067063, Tcstv1/Tcstv3, Tho4, Arginase II, BC061212 and Gm428, Eif1a, EG668777 and Pif1. Isolated stem cells identified according to this method are also provided.

The foregoing and other features and advantages will become more apparent from the following detailed description of several embodiments, which proceeds with reference to the accompanying figures.

BRIEF DESCRIPTION OF THE FIGURES

FIG. 2A shows diagrams of the exon-intron structures of nine Zscan4 paralogs. New proposed gene symbols are shown in bold italics with the current gene symbols. FIG. 2B illustrates the putative protein structures of Zscan4 paralogs, and shows predicted domains.

FIG. 3A is a diagram that illustrates the genomic structure of the Zscan4 locus (encompassing 850 kb on Chromosome 7). The top panel shows genes near the Zscan4 locus. The lower panel shows nine Zscan4 paralogous genes and their characteristic features. Six other genes (LOCs) are predicted in this region, but unrelated to Zscan4. FIG. 3B is a diagram that depicts the TaqI-, MspI-, or TaqI/MspI-digested DNA fragment sizes predicted from the genome sequences assembled from individual BAC sequences. FIG. 3C is a digital image that shows the Southern blot analysis of C57BL/6J genomic DNAs digested with TaqI, MspI, or TaqI/MspI restriction enzymes. Sizes of all DNA fragments hybridized with a Zscan4 probe (containing only exon 3 from cDNA clone C0348C03) matched with those predicted in FIG. 3B, validating the manually assembled sequences.

FIG. 4A is a table showing the three types of siRNA technologies used for the analysis of Zscan4 in preimplantation embryos and their target sequences (SEQ ID NOs: 54-59). FIG. 4B is a diagram that illustrates the locations of siRNA target sequences in the Zscan4 cDNA. FIG. 4C is a series of digital images showing the development of shZscan4-injected embryos. The morphology of representative embryos is shown. Stages of shZscan4-injected and shControl-injected embryos were assessed at 61 hrs, 80 hrs, 98 hrs and 108 hrs post-hCG injections. FIG. 4D is a series of graphs showing the percentage of shZscan4- and shControl-injected embryos at each developmental stage. shZscan4-injected (grey bars) and shControl-injected (white bars) were staged and counted at 61 hrs, 80 hrs, 98 hrs and 108 hrs post-hCG injections (M=morula; B=blastocyst). FIG. 4E is a graph showing the transcript levels of Zscan4 in shControl-injected and shZscan4-injected 2-cell embryos by qRT-PCR analysis. The expression levels were normalized by Eef1a1.

FIGS. 5A-5C are a series of graphs indicating the number of embryos at each developmental stage following injection with shZscan4. Embryos received shZscan4-injection in the nucleus of one blastomere of early 2-cell embryos. The stages of shZscan4-(gray) and shControl-(white) microinjected embryos were assessed at 52 hrs, 74 hrs and 96 hrs post-hCG injections. FIGS. 5D-5F show photographs of a 3-cell embryo (D), an unevenly cleaved embryo (E) and a mixed morula and blastocyst like embryo (F). The 3-cell embryo has one blastomere that remained at the size of a 2-cell stage blastomere and two smaller blastomeres with the size of 4-cell stage blastomeres. The 5-cell embryo has one delayed blastomere and four smaller blastomeres with the size of 8-cell blastomeres. These embryos eventually formed blastocyst-like structures, but seemed to be a mixture of a blastocyst-like cell mass and a morula-like cell mass. The morula-like cell mass was developed from one blastomere receiving shZscan4 injection, as shown by the presence of GFP, which was carried in the shZscan4 plasmid (FIG. 5G). Magnification is 200×.

FIG. 6A is an image that illustrates the expression of Zscan4 and Pou5f1 in blastocysts, blastocyst outgrowth and ES cells by whole mount in situ hybridization. FIG. 6B is a schematic illustration of the Zscan4 expression patterns.

FIGS. 7A-7E is a series of tables comparing nucleotide and amino acid sequence similarity (percent identity) among human ZSCAN4, mouse Zscan4c, Zscan4d, and Zscan4f genes.

FIG. 9A shows the percentage of embryos at each developmental stage for siControl-injected embryos (white bar) and siZscan4-injected embryos (gray bar) at 2.0, 3.5 and 4.0 d.p.c. FIG. 9B shows the percentage of expanded and hatched blastocysts at 4.5 d.p.c. in siControl-injected embryos (gray bar; photograph (a)) and siZscan4-injected embryos (black bar; photograph (b)).

FIGS. 10A-10D are a series of graphs and a table showing the development of embryos that received plus-siZscan4-injection in cytoplasm. FIG. 10A shows the percentage of embryos at each developmental stage for siControl-injected embryos (white bar) and plus-siZscan4-injected embryos (gray bar) at 2.0, 2.2, 3.0, and 4.0 days post coitus. FIGS. 10B and 10C show the transcript levels of Zscan4 in siControl-injected embryos and plus-siZscan4-injected embryos, measured by qRT-PCR analysis and normalized by Chuk (FIG. 10B) and H2afz (FIG. 10C). FIG. 10D provides the raw data of 3 biological replications of qRT-PCR analysis. †, the mean value of the cycle threshold for each biological replicate; ‡, the standard deviation.

SEQUENCE LISTING

Figure 1A:
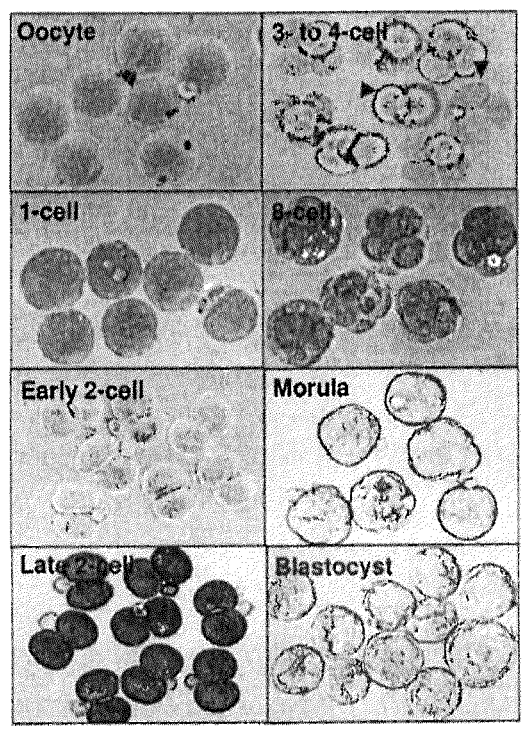
FIG. 1A is a series of digital images showing the expression profile of Zscan4 during preimplantation development by whole mount in situ hybridization. Hybridizations were performed simultaneously under the same experimental conditions for all preimplantation developmental stages. Images were taken at 200× magnification using phase contrast. Zscan4 shows a transient and high expression in the late 2-cell embryos. Such a high level of expression was not observed in 3-cell (two examples indicated by red arrows) and 4-cell embryos.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 14, 2011, 170 KB, which is incorporated by reference herein. In the accompanying sequence listing:

SEQ ID NOs: 1 and 2 are the nucleotide sequences of forward and reverse PCR primers for amplification of Zscan4d from 2-cell embryos.

SEQ ID NOs: 3 and 4 are the nucleotide sequences of PCR primers for amplifying a probe designed to contain exon 3 of Zscan4.

SEQ ID NO: 5 is the nucleotide sequence of the Zscan4 PCR and sequencing primer Zscan4_For.

SEQ ID NO: 6 is the nucleotide sequence of the Zscan4 PCR and sequencing primer Zscan4_Rev.

SEQ ID NO: 7 is the nucleotide sequence of the Zscan4 sequencing primer Zscan4_400Rev.

SEQ ID NO: 8 is the nucleotide sequence of the Zscan4 sequencing primer Zscan4_300Rev.

SEQ ID NO: 9 is the nucleotide sequence of the shZscan4 siRNA. SEQ ID NO: 10 is the nucleotide sequence of the siControl siRNA.

SEQ ID NO: 11 is the nucleotide sequence of Genbank Accession No. BC050218 (deposited Apr. 3, 2003), a cDNA clone derived from ES cells (Clone No. C0348C03).

SEQ ID NO: 12 is the nucleotide sequence of Zscan4-ps1.

SEQ ID NO: 13 is the nucleotide sequence of Zscan4-ps2.

SEQ ID NO: 14 is the nucleotide sequence of Zscan4-ps3.

SEQ ID NOs: 15 and 16 are the nucleotide and amino acid sequences of Zscan4a.

SEQ ID NOs: 17 and 18 are the nucleotide and amino acid sequences of Zscan4b.

SEQ ID NOs: 19 and 20 are the nucleotide and amino acid sequences of Zscan4c.

SEQ ID NOs: 21 and 22 are the nucleotide and amino acid sequences of Zscan4d.

SEQ ID NOs: 23 and 24 are the nucleotide and amino acid sequences of Zscan4e.

SEQ ID NOs: 25 and 26 are the nucleotide and amino acid sequences of Zscan4f.

SEQ ID NO: 27 is the nucleotide sequence of Genbank Accession No. XM_145358, deposited Jan. 10, 2006, incorporated by reference herein.

SEQ ID NO: 28 is the nucleotide sequence of the Zscan4-Emerald expression vector.

SEQ ID NOs: 29 and 30 are the nucleotide and amino acid sequences of human ZSCAN4 (Genbank Accession No. NM_152677, deposited Sep. 6, 2002, incorporated by reference herein).

SEQ ID NO: 31 is the nucleotide sequence of the Trim43 promoter.

SEQ ID NOs: 32 and 33 are the nucleotide and amino acid sequences of Trim43.

SEQ ID NOs: 34 and 35 are the nucleotide and amino acid sequences of AF067063, Genbank Accession No. NM_001001449, deposited May 29, 2004, incorporated by reference herein.

SEQ ID NOs: 36 and 37 are the nucleotide and amino acid sequences of BC061212, Genbank Accession No. NM_198667.1, deposited Nov. 15, 2003, incorporated by reference herein.

SEQ ID NOs: 38 and 39 are the nucleotide and amino acid sequences of Gm428, Genbank Accession No. NM_001081644, deposited Feb. 22, 2007, incorporated by reference herein.

SEQ ID NOs: 40 and 41 are the nucleotide and amino acid sequences of Arginase II, Genbank Accession No. NM_009705, deposited Jan. 26, 2000, incorporated by reference herein.

SEQ ID NOs: 42 and 43 are the nucleotide and amino acid sequences of Tcstv1, Genbank Accession No. NM_018756, deposited Jul. 12, 2007, incorporated by reference herein.

SEQ ID NOs: 44 and 45 are the nucleotide and amino acid sequences of Tcstv3, Genbank Accession No. NM_153523, deposited Oct. 13, 2002, incorporated by reference herein.

SEQ ID NOs: 46 and 47 are the nucleotide and amino acid sequences of Tho4, Genbank Accession No. XM_902103, deposited Dec. 2, 2005, incorporated by reference herein.

SEQ ID NOs: 48 and 49 are the nucleotide and amino acid sequences of Eif1a, Genbank Accession No. NM_010120, deposited Aug. 3, 2002, incorporated by reference herein.

SEQ ID NOs: 50 and 51 are the nucleotide and amino acid sequences of EG668777, Genbank Accession No. XM_001003556, deposited Apr. 27, 2006, incorporated by reference herein.

SEQ ID NOs: 52 and 53 are the nucleotide and amino acid sequences of Pif1, Genbank Accession No. NM_172453, deposited Dec. 24, 2002, incorporated by reference herein.

SEQ ID NO: 54 is the nucleotide sequence of the Plus-siZscan4 (J-064700-05) target sequence.

SEQ ID NO: 55 is the nucleotide sequence of the Plus-siZscan4 (J-064700-06) target sequence.

SEQ ID NO: 56 is the nucleotide sequence of the Plus-siZscan4 (J-064700-07) target sequence.

SEQ ID NO: 57 is the nucleotide sequence of the Plus-siZscan4 (J-064700-08) target sequence.

SEQ ID NO: 58: is the nucleotide sequence of the siZscan4 target sequence.

SEQ ID NO: 59 is the nucleotide sequence of the of shZscan4 target sequence.

SEQ ID NO: 60 is the nucleotide consensus sequence of nucleotides 1-1848 of Zscan4c, Zscan4d and Zscan4f.

DETAILED DESCRIPTION

I. Abbreviations

| | |
|---|---|
| CDS | Coding sequence |
| CMV | Cytomegalovirus |
| DNA | Deoxyribonucleic acid |
| d.p.c. | Days post coitus |
| EC | Embryonic carcinoma |
| EG | Embryonic germ |
| ES | Embryonic stem |
| GS | Germline stem |
| GFP | Green fluorescent protein |
| hCG | Human chorionic gonadotropin |
| ICM | Inner cell mass |
| IVF | In vitro fertilization |
| LIF | Leukemia inhibitory factor |
| maGSC | Multipotent adult germline stem cell |
| MAPC | Multipotent adult progenitor cell |
| PCR | Polymerase chain reaction |
| qRT-PCR | Quantitative reverse-transcriptase polymerase chain reaction |
| RNA | Ribonucleic acid |
| siRNA | small interfering RNA |
| TS | Trophoblast stem |
| USSC | Unrestricted somatic stem cell |
| ZGA | Zygotic genome activation |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Alter: A change in an effective amount of a substance of interest, such as a polynucleotide or polypeptide. The amount of the substance can be changed by a difference in the amount of the substance produced, by a difference in the amount of the substance that has a desired function, or by a difference in the activation of the substance. The change can be an increase or a decrease. The alteration can be in vivo or in vitro. In several embodiments, altering an effective amount of a polypeptide or polynucleotide is at least about a 50%, 60%, 70%, 80%, 90%, 95%, 96%, 97%, 98%, 99%, or 100% increase or decrease in the effective amount (level) of a substance. Altering an effective amount of a polypeptide or polypeptide includes increasing the expression of Zscan4 in a cell. In another embodiment, an alteration in a polypeptide or polynucleotide affects a physiological property of a cell, such as the differentiation, proliferation, or viability of the cell. For example, increasing expression of Zscan4 in a stem cell inhibits differentiation and promotes viability of the stem cell.

Blastocyst: The structure formed in early mammalian embryogenesis, after the formation of the blastocele, but before implantation. It possesses an inner cell mass, or embryoblast, and an outer cell mass, or trophoblast. The human blastocyst comprises 70-100 cells. As used herein, blastocyst outgrowth refers to the process of culturing embryonic stem cells derived from the inner cell mass of a blastocyst. Promoting blastocyst outgrowth refers to enhancing the viability and proliferation of embryonic stem cells derived from the blastocyst.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Co-expressed: In the context of the present disclosure, genes that are "co-expressed" with Zscan4 (also referred to as "Zscan4 co-expressed genes") are genes that exhibit a similar expression pattern as Zscan4 during embryonic development and in ES cells. Specifically, the co-expressed genes are expressed in the same undifferentiated subpopulation of ES cells as Zscan 4, and during embryonic development, these genes are most abundantly expressed at the 2-cell stage. Nine co-expressed genes are described herein, including AF067063, Tcstv1/Tcstv3, Tho4, Arginase II, BC061212 and Gm428, Eif1a, EG668777 and Pif1. However, co-expressed genes are not limited to those disclosed herein, but include any genes exhibiting an expression pattern similar to Zscan4.

AF067063 encodes hypothetical protein LOC380878. The full length cDNA sequence of AF067063 (SEQ ID NO: 34) is 886 base pairs in length and is organized into three exons encoding several hypothetical proteins (for example, SEQ ID NO: 35), which appear to be mouse specific.

BC061212 encodes a protein belonging to the PRAME (preferentially expressed antigen melanoma) family. The full length cDNA sequence of BC061212 (SEQ ID NO: 36) is 1625 base pairs in length and is organized into four exons, encoding a protein of 481 residues in length (SEQ ID NO: 37).

Gm428 (gene model 428) encodes a hypothetical protein. The full length cDNA sequence of Gm428 (SEQ ID NO: 38) is 1325 base pairs in length and is organized into five exons encoding a protein of 360 residues in length (SEQ ID NO: 39).

Arginase II belongs to the Arginase family and may play a role in the regulation of extra-urea cycle arginine metabolism, and in down-regulation of nitric oxide synthesis. The full length cDNA sequence of Arginase II (SEQ ID NO: 40) is 1415 base pairs in length and is organized into eight exons encoding a protein of 354 residues in length (SEQ ID NO: 41).

Tsctv1 and Tsctv3 are splice variants. The full length cDNA of Tsctv1 (SEQ ID NO: 42) is 858 base pairs in length and contains two exons encoding a protein of 171 residues (SEQ ID NO: 43). The full length cDNA sequence of Tsctv3 (SEQ ID NO: 44) is 876 base pairs in length and contains one exon encoding a protein of 169 residues (SEQ ID NO: 45). This family of proteins consists of several hypothetical proteins of approximately 170 residues in length and appears to be mouse-specific.

Tho4 (also called EG627488) encodes a protein with an RNA recognition motif (RRM) involved in regulation of alternative splicing, and protein components of small nuclear ribonucleoproteins (snRNPs). The full length cDNA sequence of Tho4 (SEQ ID NO: 46) is 811 base pairs in length and is organized into three exons encoding a protein of 163 residues in length (SEQ ID NO: 47).

Eif1a belongs to the eukaryotic translation initiation factor family. The full length cDNA sequence of Eif1a (SEQ ID NO: 48) is 2881 base pairs in length and encodes a protein of 144 amino acids (SEQ ID NO: 49).

EG668777 is a predicted gene having similarity to retinoblastoma-binding protein 6, isoform 2. The full length cDNA sequence of EG668777 is 1918 base pairs in length (SEQ ID NO: 50) and contains one exon encoding a protein of 547 residues (SEQ ID NO: 51).

Pif1 is an ATP-dependent DNA helicase. The full length cDNA sequence of Pif1 (SEQ ID NO: 52) is 3680 base pairs in length and contains 12 exons encoding a protein of 650 amino acids (SEQ ID NO: 53).

Degenerate variant: A polynucleotide encoding a polypeptide, such as a Zscan4 polypeptide, that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

Differentiation: Refers to the process by which a cell develops into a specific type of cell (for example, muscle cell, skin cell etc.). In the context of the present disclosure, differentiation of embryonic stem cells refers to the development of the cells toward a specific cell lineage. As a cell becomes more differentiated, the cell loses potency, or the ability to become multiple different cell types. As used herein, inhibiting differentiation means preventing or slowing the development of a cell into a specific lineage.

Embryonic stem (ES) cells: Pluripotent cells isolated from the inner cell mass of the developing blastocyst. "ES cells" can be derived from any organism. ES cells can be derived from mammals. In one embodiment, ES cells are produced from mice, rats, rabbits, guinea pigs, goats, pigs, cows, monkeys and humans. Human and murine derived ES cells are preferred. ES cells are pluripotent cells, meaning that they can generate all of the cells present in the body (bone, muscle, brain cells, etc.). Methods for producing murine ES cells can be found in U.S. Pat. No. 5,670,372, herein incorporated by reference. Methods for producing human ES cells can be found in U.S. Pat. No. 6,090,622, PCT Publication No. WO 00/70021 and PCT Publication No. WO 00/27995, herein incorporated by reference.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion", or "expanded." Typically, during expansion, the cells do not differentiate to form mature cells.

Expression vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

Heterologous: A heterologous polypeptide or polynucleotide refers to a polypeptide or polynucleotide derived from a different source or species.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Isolated: An isolated nucleic acid has been substantially separated or purified away from other nucleic acid sequences and from the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids. Similarly, "isolated" proteins have been substantially separated or purified from other proteins of the cells of an organism in which the protein naturally occurs, and encompasses proteins prepared by recombination expression in a host cell as well as chemically synthesized proteins.

Multipotent cell: Refers to a cell that can form multiple cell lineages, but not all cell lineages.

Non-human animal: Includes all animals other than humans. A non-human animal includes, but is not limited to, a non-human primate, a farm animal such as swine, cattle, and poultry, a sport animal or pet such as dogs, cats, horses, hamsters, rodents, such as mice, or a zoo animal such as lions, tigers or bears. In one example, the non-human animal is a transgenic animal, such as a transgenic mouse, cow, sheep, or goat. In one specific, non-limiting example, the transgenic non-human animal is a mouse.

Operably linked: A first nucleic acid sequence is operably linked to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and where necessary to join two protein coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Pharmaceutical agent: A chemical compound, small molecule, or other composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Pluripotent cell: Refers to a cell that can form all of an organism's cell lineages (endoderm, mesoderm and ectoderm), including germ cells, but cannot form an entire organisms autonomously.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide, such as a Zscan4. Biologically functional fragments, for example, can vary in size from a polypeptide fragment as small as an epitope capable of binding an antibody molecule to a large polypeptide capable of participating in the characteristic induction or programming of phenotypic changes within a cell, including affecting cell proliferation or differentiation. An "epitope" is a region of a polypeptide capable of binding an immunoglobulin generated in response to contact with an antigen. Thus, smaller peptides containing the biological activity of Zscan4, or conservative variants of Zscan4, are thus included as being of use.

The term "soluble" refers to a form of a polypeptide that is not inserted into a cell membrane.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. Thus, in several non-limiting examples, a Zscan4 polypeptide, or other polypeptides disclosed herein, includes at most two, at most five, at most ten, at most twenty, or at most fifty conservative substitutions. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may be, for example, at least 80%, 90% or even 95% or 98% identical to the native amino acid sequence.

Primers: Short nucleic acids, for example DNA oligonucleotides ten nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Probes and primers as used herein may, for example, include at least 10 nucleotides of the nucleic acid sequences that are shown to encode specific proteins. In order to enhance specificity, longer probes and primers may also be employed, such as probes and primers that comprise 15, 20, 30, 40, 50, 60, 70, 80, 90 or 100 consecutive nucleotides of the disclosed nucleic acid sequences. Methods for preparing and using probes and primers are described in the references, for example Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences; Innis et al. (1990) *PCR Protocols, A Guide to Methods and Applications*, Innis et al. (Eds.), Academic Press, San Diego, Calif. PCR primer pairs can be derived from a known sequence, for example, by using computer programs intended for that purpose such as Primer (Version 0.5, 1991, Whitehead Institute for Biomedical Research, Cambridge, Mass.).

When referring to a probe or primer, the term "specific for (a target sequence)" indicates that the probe or primer hybridizes under stringent conditions substantially only to the target sequence in a given sample comprising the target sequence.

Prolonging viability: As used herein, "prolonging viability" of a stem cell refers to extending the duration of time a stem cell is capable of normal growth and/or survival.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

Reporter gene: A reporter gene is a gene operably linked to another gene or nucleic acid sequence of interest (such as a promoter sequence). Reporter genes are used to determine whether the gene or nucleic acid of interest is expressed in a cell or has been activated in a cell. Reporter genes typically have easily identifiable characteristics, such as fluorescence, or easily assayed products, such as an enzyme. Reporter genes can also confer antibiotic resistance to a host cell. In one embodiment, the reporter gene encodes the fluorescent protein Emerald. In another embodiment, the reporter gene encodes the fluorescent protein Strawberry.

Senescence: The inability of a cell to divide further. A senescent cell is still viable, but does not divide.

Stem cell: A cell having the unique capacity to produce unaltered daughter cells (self-renewal; cell division produces at least one daughter cell that is identical to the parent cell) and to give rise to specialized cell types (potency). Stem cells include, but are not limited to, ES cells, EG cells, GS cells, MAPCs, maGSCs and USSCs. In one embodiment, stem cells can generate a fully differentiated functional cell of more than one given cell type. The role of stem cells in vivo is to replace cells that are destroyed during the normal life of an animal. Generally, stem cells can divide without limit. After division, the stem cell may remain as a stem cell, become a precursor cell, or proceed to terminal differentiation. A precursor cell is a cell that can generate a fully differentiated functional cell of at least one given cell type. Generally, precursor cells can divide. After division, a precursor cell can remain a precursor cell, or may proceed to terminal differentiation.

Subpopulation: An identifiable portion of a population. As used herein, a "subpopulation" of stem cells expressing Zscan4 is the portion of stem cells in a given population that has been identified as expressing Zscan4. In one embodiment, the subpopulation is identified using an expression vector comprising a Zscan4 promoter and a reporter gene, wherein detection of expression of the reporter gene in a cell indicates the cell expresses Zscan4 and is part of the subpopulation. As described herein, the subpopulation of ES cells expressing Zscan4 can further be identified by co-expression of one or more genes disclosed herein, including AF067063, Tcstv1/Tcstv3, Tho4, Arginase II, BC061212 and Gm428, Eif1a, EG668777 and Pif1.

Totipotent cell: Refers to a cell that can form an entire organism autonomously. Only a fertilized egg (oocyte) possesses this ability (stem cells do not).

Transgenic animal: A non-human animal, usually a mammal, having a non-endogenous (heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. A "transgene" is meant to refer to such heterologous nucleic acid, such as, heterologous nucleic acid in the form of an expression construct (such as for the production of a "knock-in" transgenic animal) or a heterologous nucleic acid that upon insertion within or adjacent to a target gene results in a decrease in target gene expression (such as for production of a "knock-out" transgenic animal).

Transfecting or transfection: Refers to the process of introducing nucleic acid into a cell or tissue. Transfection can be achieved by any one of a number of methods, such as, but not limited to, liposomal-mediated transfection, electroporation and injection.

Trim43 (tripartite motif-containing protein 43): A gene identified herein as exhibiting morula-specific expression during embryonic development. The nucleotide and amino acid sequences of Trim43 are provided herein as SEQ ID NO: 32 and SEQ ID NO: 33, respectively.

Zscan4: A group of genes identified herein as exhibiting 2-cell embryonic stage and ES cell-specific expression. In the mouse, the term "Zscan4" refers to a collection of genes including three pseudogenes (Zscan1-ps1, Zscan4-ps2 and Zscan4-ps3) and six expressed genes (Zscan4a, Zscan4b, Zscan4c, Zscan4d, Zscan4e and Zscan4f). As used herein, Zscan4 also includes human ZSCAN4. Zscan4 refers to Zscan4 polypeptides and Zscan4 polynucleotides encoding the Zscan4 polypeptides.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein are Zscan4 polypeptides and polynucleotides encoding these polypeptides, which are of use in inhibiting differentiation and increasing proliferation of cells, such as stem cells, including embryonic stem cells. Stem cells, especially ES cells in the undifferentiated condition, were previously considered to be a relatively homogenous cell population. However, described herein is the unique expression of Zscan4 in a subpopulation of stem cells, which establishes the presence of a unique cell population among undifferentiated ES cells and provides the means to identify and isolate these cells. Also described herein is the identification of nine genes co-expressed with Zscan4 in the undifferentiated ES cell subpopulation. These genes include AF067063, Tcstv1/Tcstv3, Tho4, Arginase II, BC061212 and Gm428, Eif1a, EG668777 and Pif1. Further described herein is the identification of Trim43 as a gene exhibiting morula-specific gene expression.

It is disclosed herein that Zscan4 is specifically expressed during the 2-cell embryonic stage and in a subpopulation of embryonic stem cells. There is a genus of Zscan4-related genes, including three pseudogenes (Zscan4-ps1, Zscan4-ps2 and Zscan4-ps3) and six expressed genes (Zscan4a, Zscan4b, Zscan4c, Zscan4d, Zscan4e and Zscan4f). The Zscan4 genus also includes human ZSCAN4. It is further disclosed herein that AF067063, Tcstv1/Tcstv3, Tho4, Arginase II, BC061212 and Gm428, Eif1a, EG668777 and Pif1 are co-expressed with Zscan4 during embryonic development. Like Zscan4, during embryonic development, these genes are expressed most abundantly at the 2-cell stage.

Methods are provided herein for inhibiting differentiation of a stem cell comprising increasing the expression of Zscan4 in the stem cell. As described herein, the use of Zscan4 includes the use of any Zscan4 gene, including Zscan4a, Zscan4b, Zscan4c, Zscan4d, Zscan4e, Zscan4f and human ZSCAN4. In some embodiments, the Zscan4 gene is at least 90%, at least 95%, at least 96%, at least 97%, at least 98% or at least 99% identical to Zscan4c (SEQ ID NO: 19), Zscan4d (SEQ ID NO: 21) or Zscan4f (SEQ ID NO: 25). In another embodiment, the Zscan4 gene comprises SEQ ID NO: 60.

Increasing expression of Zscan4 in a cell, such as a stem cell, can be achieved according to any number of methods well known in the art. In one embodiment, increasing expression of Zscan4 in a stem cell comprises transfecting the stem cell with a nucleotide encoding Zscan4 operably linked to a promoter. The promoter can be any type of promoter, including a constitutive promoter or an inducible promoter. In one embodiment, the stem cells are transfected with a vector comprising the nucleotide sequence encoding Zscan4 operably linked to the promoter. The vector can be any type of vector, such as a viral vector or a plasmid vector. In one embodiment, the Zscan4 nucleotide sequence is at least 90%, at least 95%, at least 96%, at least 97%, at least 98% or at least 99% identical to Zscan4c (SEQ ID NO: 19), Zscan4d (SEQ ID NO: 21) or Zscan4f (SEQ ID NO: 25). In another embodiment, the Zscan4 nucleotide sequence comprises SEQ ID NO: 60.

In one embodiment of the methods described herein, inhibiting differentiation of the stem cell increases viability of the stem cells. In another embodiment, inhibiting differentiation of the stem cell prevents senescence of the stem cell. As described herein, the stem cell can be any type of stem cell, including, but not limited to, an embryonic stem cell, an embryonic germ cell, a germline stem cell or a multipotent adult progenitor cell.

Also provided herein is a method of promoting blastocyst outgrowth of an embryonic stem cell, comprising increasing the expression of Zscan4 in the embryonic stem cell, thereby promoting blastocyst outgrowth of the embryonic stem cell. Promoting blastocyst outgrowth can include increasing the efficiency of outgrowth or increasing the number of embryonic stem cells resulting from blastocyst outgrowth. In one embodiment, the method comprises increasing expression of Zscan4 in the cells during the early stages of blastocyst outgrowth, such as prior to proliferation of the stem cells. As described herein, Zscan4 includes any Zscan4 gene, including Zscan4a, Zscan4b, Zscan4c, Zscan4d, Zscan4e, Zscan4f, and human ZSCAN4. In one embodiment, the Zscan4 gene is at least 90%, at least 95%, at least 96%, at least 97%, at least 98% or at least 99% identical to Zscan4c (SEQ ID NO: 19), Zscan4d (SEQ ID NO: 21) or Zscan4f (SEQ ID NO: 25). In another embodiment, the Zscan4 gene comprises SEQ ID NO: 60.

In one embodiment, increasing the expression of Zscan4 in the stem cell comprises transfecting the stem cell with a nucleotide sequence encoding a Zscan4 operably linked to a promoter. The promoter can be any type of promoter, including an inducible promoter or a constitutive promoter. In one embodiment, the cells are transfected with a vector comprising the nucleotide encoding Zscan4 operably linked to a promoter. The vector can be any type of vector, including a viral vector or a plasmid vector.

A method is also provided for identifying a subpopulation of stem cells expressing Zscan4, comprising transfecting the cells with an expression vector comprising a Zscan4 promoter and a reporter gene, wherein expression of the reporter gene indicates Zscan4 is expressed in the subpopulation of stem cells. In one embodiment, the promoter is a Zscan4c promoter. In another embodiment, the Zscan4c promoter includes the nucleic acid sequence set forth as nucleotides 1-2540 of SEQ ID NO: 28, such as nucleotides 1-2643, 1-3250, or 1-3347 of SEQ ID NO: 28. In another embodiment, the expression vector comprises the nucleic acid sequence set forth as SEQ ID NO: 28. As described herein, the subpopulation of ES cells expressing Zscan4 are in an undifferentiated state. Further provided is a method of identifying the undifferentiated subpopulation of ES cells by detecting expression of one or more Zscan4 co-expressed genes, such as AF067063, Tcstv1/Tcstv3, Tho4, Arginase II, BC061212 and Gm428, Eif1a, EG668777 and Pif1. Detection of expression of these genes can be accomplished using any means well known in the art, such as, for example, RT-PCR, Northern blot or in situ hybridization. Further provided are isolated stem cells identified according to this method.

An isolated expression vector comprising a Zscan4 promoter operably linked to a nucleic acid sequence encoding a heterologous polypeptide is also provided. In one embodiment, the Zscan4 promoter is a Zscan4c promoter. In another embodiment, the Zscan4c promoter comprises the nucleic acid sequence set forth as nucleotides 1-2540 of SEQ ID NO: 28, such as nucleotides 1-2643, 1-3250, or 1-3347 of SEQ ID NO: 28. In another embodiment, the heterologous polypeptide is a marker, enzyme or fluorescent protein. The expression vector can be any type of vector, including, but not limited to a viral vector or a plasmid vector.

Further provided herein is an ES cell line comprising an expression vector comprising a Zscan4 promoter operably linked to a heterologous polypeptide. In one embodiment, the Zscan4 promoter is a Zscan4c promoter. In another embodiment, the Zscan4c promoter comprises the nucleic acid sequence set forth as nucleotides 1-2540 of SEQ ID NO: 28, such as nucleotides 1-2643, 1-3250, or 1-3347 of SEQ ID NO: 28. In another embodiment, the heterologous polypeptide is a marker, enzyme or fluorescent protein. In one example, the fluorescent protein is Emerald.

An isolated expression vector comprising a Trim43 promoter operably linked to a nucleic acid sequence encoding a heterologous polypeptide is also provided. In one embodiment, the Trim43 promoter comprises at least a portion of the nucleic acid sequence set forth as SEQ ID NO: 31. The portion of SEQ ID NO: 31 to be included in the expression vector is at least a portion of SEQ ID NO: 31 that is capable of promoting transcription of the heterologous polypeptide in a cell in which Trim43 is expressed. In some embodiments, the Trim43 promoter sequence is at least 70%, at least 80%, at least 90%, at least 95% or at least 99% identical to SEQ ID NO: 31. In another embodiment, the Trim43 promoter comprises SEQ ID NO: 31. In another embodiment, the Trim43 promoter consists of SEQ ID NO: 31. In some embodiments, the heterologous polypeptide is a marker, enzyme or fluorescent protein. In one example the fluorescent protein is Strawberry. The expression vector can be any type of vector, including, but not limited to a viral vector or a plasmid vector.

Further provided herein is an ES cell line containing an expression vector comprising a Trim43 promoter operably linked to a heterologous polypeptide. In one embodiment, the Trim43 promoter comprises at least a portion of the nucleic acid sequence set forth as SEQ ID NO: 31. In some embodiments, the Trim43 promoter sequence is at least 70%, at least 80%, at least 90%, at least 95% or at least 99% identical to SEQ ID NO: 31. In another embodiment, the Trim43 promoter comprises SEQ ID NO: 31. In another embodiment, the Trim43 promoter consists of SEQ ID NO: 31. In another embodiment, the heterologous polypeptide is a marker, enzyme or fluorescent protein. In one example, the fluorescent protein is Strawberry.

Provided herein are antibodies specific for Zscan4. In one embodiment, the Zscan4 antibodies specifically recognize Zscan4a, Zscan4b, Zscan4c, Zscan4d, Zscan4e, Zscan4f or human ZSCAN4. Also provided are antibodies specific for each Zscan4 co-expressed gene, including antibodies raised against at least a portion of a polypeptide encoded by AF067063, Tcstv1/Tcstv3, Tho4, Arginase II, BC061212 and Gm428, Eif1a, EG668777 or Pif1.

Also described herein are transgenic animals harboring a transgene that includes the Zscan4 polynucleotide sequences disclosed herein. Also provided are transgenic animals harboring a transgene that includes polynucleotide sequences of one or more of the Zscan4 co-expressed genes. Such transgenic animals include, but are not limited to, transgenic mice.

Further provided is a transgenic non-human animal comprising a nucleic acid sequence (a transgene) encoding a heterologous polypeptide operably linked to a Zscan4 promoter. In some embodiments, the heterologous polypeptide is a marker, enzyme or fluorescent protein. In one embodiment, the heterologous polypeptide is fluorescent protein. In one example, the fluorescent protein is Emerald. In one embodiment, the Zscan4 promoter is a Zscan4c promoter. In another embodiment, the Zscan4c promoter comprises the nucleic acid sequence set forth as nucleotides 1-2540 of SEQ ID NO: 28, such as nucleotides 1-2643, 1-3250, or 1-3347 of SEQ ID NO: 28.

In another embodiment, the transgenic non-human animal further comprises a nucleic acid sequence encoding a heterologous polypeptide operably linked to a Trim43 promoter. In one embodiment, the Trim43 promoter comprises the nucleic acid sequence set forth as SEQ ID NO: 31. The heterologous polypeptide can be, for example, a marker, enzyme or fluorescent protein. In one embodiment, the heterologous polypeptide is a fluorescent protein. In one example, the fluorescent protein is Strawberry. In some embodiments, the transgenic non-human animal is a transgenic mouse.

Also provided herein are isolated embryonic stem cells obtained from an embryo of the transgenic non-human animal. In one embodiment, the transgenic non-human animal is a transgenic mouse.

IV. Methods of Inducing Differentiation and/or Inhibiting Proliferation of Stem Cells A method for inhibiting differentiation of a stem cell is disclosed herein. A method for increasing viability and/or inducing proliferation of a stem cell is also disclosed herein. A method is also provided herein for inhibiting senescence of a stem cell. The methods include altering the level of a Zscan4 polypeptide in the cell, thereby inhibiting differentiation and/or inducing proliferation of the cell, and/or inhibiting senescence of the cell. The cell can be in vivo or in vitro.

It is shown herein that inhibiting Zscan4 in embryos blocks the 2- to 4-cell stage embryonic transition. Inhibition of Zscan4 expression also prevents blastocysts from expanding and implanting and prevents the outgrowth of embryonic stem cells from blastocysts. In addition, in embryonic stem cells, Zscan4 expression is only detected in a subpopulation of undifferentiated stem cells. Thus, expression of Zscan4 plays an important role in maintaining ES cells in an undifferentiated state, which is necessary for ES cell viability and proliferation. Zscan4 is also important in allowing outgrowth of ES cells from blastocysts. Therefore, provided herein are methods of increasing expression of Zscan4 in a stem cell to inhibit differentiation, increase viability and prevent senescence of a stem cell. The methods provided herein also include increasing expression of Zscan4 to promote blastocyst outgrowth of ES cells.

Expression of Zscan4 can be increased to inhibit differentiation and/or induce proliferation. In one example, expression of Zscan4 is increased as compared to a control. Increased expression includes, but is not limited to, at least a 20% increase in the amount of Zscan4 mRNA or polypeptide in a cell as compared to a control, such as, but not limited to, at least about a 30%, 50%, 75%, 100%, or 200% increase of Zscan4 mRNA or polypeptide. Suitable controls include a cell not contacted with an agent that alters Zscan4 expression, or not transfected with a vector encoding Zscan4, such as a wild-type stem cell. Suitable controls also include standard values. Exemplary Zscan4 amino acid sequences are set forth in the Sequence Listing as SEQ ID NO: 16 (Zscan4a), SEQ ID NO: 18 (Zscan4b), SEQ ID NO: 20 (Zscan4c), SEQ ID NO: 22 (Zscan4d), SEQ ID NO: 24 (Zscan4e), SEQ ID NO: 26 (Zscan4f) and SEQ ID NO: 30 (human ZSCAN4).

Specific, non-limiting examples of Zscan4 polypeptides include polypeptides including an amino acid sequence at least about 80%, 85%, 90%, 95%, or 99% homologous to the amino acid sequence set forth in SEQ ID NO: 16, 18, 20, 22, 24, 26 or 30. In a further embodiment, a Zscan4 polypeptide is a conservative variant of SEQ ID NO: 16, 18, 20, 22, 24, 26 or 30, such that it includes no more than fifty conservative amino acid substitutions, such as no more than two, no more than five, no more than ten, no more than twenty, or no more than fifty conservative amino acid substitutions in SEQ ID NO: 16, 18, 20, 22, 24, 26 or 30. In another embodiment, a Zscan4 polypeptide has an amino acid sequence as set forth in SEQ ID NO: 16, 18, 20, 22, 24, 26 or 30.

Fragments and variants of a Zscan4 polypeptide can readily be prepared by one of skill in the art using molecular techniques. In one embodiment, a fragment of a Zscan4 polypeptide includes at least 8, 10, 15, or 20 consecutive amino acids of the Zscan4 polypeptide. In another embodiment, a fragment of a Zscan4 polypeptide includes a specific antigenic epitope found on a full-length Zscan4. In a further embodiment, a fragment of Zscan4 is a fragment that confers a function of Zscan4 when transferred into a cell of interest, such as, but not limited to, inhibiting differentiation or increasing proliferation of the cell.

One skilled in the art, given the disclosure herein, can purify a Zscan4 polypeptide using standard techniques for protein purification. The substantially pure polypeptide will yield a single major band on a non-reducing polyacrylamide gel. The purity of the Zscan4 polypeptide can also be determined by amino-terminal amino acid sequence analysis.

Minor modifications of the Zscan4 polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein.

One of skill in the art can readily produce fusion proteins including a Zscan4 polypeptide and a second polypeptide of interest. Optionally, a linker can be included between the Zscan4 polypeptide and the second polypeptide of interest. Fusion proteins include, but are not limited to, a polypeptide including a Zscan4 polypeptide and a marker protein. In one embodiment, the marker protein can be used to identify or purify a Zscan4 polypeptide. Exemplary fusion proteins include, but are not limited to, green fluorescent protein, six histidine residues, or myc and a Zscan4 polypeptide.

Polynucleotides encoding a Zscan4 polypeptide are also provided, and are termed Zscan4 polynucleotides. These polynucleotides include DNA, cDNA and RNA sequences which encode a Zscan4. It is understood that all polynucleotides encoding a Zscan4 polypeptide are also included herein, as long as they encode a polypeptide with the recognized activity, such as the binding to an antibody that recognizes a Zscan4 polypeptide, or modulating cellular differentiation or proliferation. The polynucleotides include sequences that are degenerate as a result of the genetic code. There are 20 natural amino acids, most of which are specified by more than one codon. Therefore, all degenerate nucleotide sequences are included as long as the amino acid sequence of the Zscan4 polypeptide encoded by the nucleotide sequence is functionally unchanged. A Zscan4 polynucleotide encodes a Zscan4 polypeptide, as disclosed herein. Exemplary polynucleotide sequences encoding Zscan4 are set for in the Sequence Listing as SEQ ID NO: 12 (Zscan4-ps1), SEQ ID NO: 13 (Zscan4-ps2), SEQ ID NO: 14 (Zscan4-ps3), SEQ ID NO: 15 (Zscan4a), SEQ ID NO: 17 (Zscan4b), SEQ ID NO: 19 (Zscan4c), SEQ ID NO: 21 (Zscan4d), SEQ ID NO: 23 (Zscan4e), SEQ ID NO: 25 (Zscan4f) and SEQ ID NO: 29 (human ZSCAN4).

In some embodiments, the Zscan4 polynucleotide sequence is at least 90%, at least 95%, at least 96%, at least 97%, at least 98% or at least 99% identical to Zscan4c (SEQ ID NO: 19), Zscan4d (SEQ ID NO: 21) or Zscan4f (SEQ ID NO: 25). In another embodiment, the Zscan4 gene comprises SEQ ID NO: 60.

The Zscan4 polynucleotides include recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA. Also included in this disclosure are fragments of the above-described nucleic acid sequences that are at least 15 bases in length, which is sufficient to permit the fragment to selectively hybridize to DNA that encodes the disclosed Zscan4 polypeptide (e.g., a polynucleotide that encodes SEQ ID NO: 16, 18, 20, 22, 24, 26 or 30) under physiological conditions. The term "selectively hybridize" refers to hybridization under moderately or highly stringent conditions, which excludes non-related nucleotide sequences.

Also contemplated herein is the use of a Zscan4 polynucleotide, or the complement of a Zscan4 polynucleotide, for RNA interference. Fragments of Zscan4 polynucleotides or their complements can be designed as siRNA molecules to inhibit expression of one or more Zscan4 proteins. In one embodiment, the siRNA compounds are fragments of a Zscan4 pseudogene. Methods of preparing and using siRNA are generally disclosed in U.S. Pat. No. 6,506,559, incorporated herein by reference (see also reviews by Milhavet et al., *Pharmacological Reviews* 55:629-648, 2003; and Gitlin et al., *J. Virol.* 77:7159-7165, 2003; incorporated herein by reference). The double-stranded structure of siRNA can be formed by a single self-complementary RNA strand or two complementary RNA strands.

The siRNA can comprise one or more strands of polymerized ribonucleotide, and may include modifications to either the phosphate-sugar backbone or the nucleoside. For example, the phosphodiester linkages of natural RNA can be modified to include at least one of a nitrogen or sulfur heteroatom. Modifications in RNA structure can be tailored to allow specific genetic inhibition while avoiding a general panic response in some organisms which is generated by dsRNA. Likewise, bases can be modified to block the activity of adenosine deaminase.

Inhibition is sequence-specific in that nucleotide sequences corresponding to the duplex region of the RNA are targeted for genetic inhibition. Nucleic acid containing a nucleotide sequence identical to a portion of a target sequence can be used for inhibition. RNA sequences with insertions, deletions, and single point mutations relative to the target sequence have also been found to be effective for inhibition. Sequence identity may be optimized by alignment algorithms known in the art and calculating the percent difference between the nucleotide sequences. Alternatively, the duplex region of the RNA can be defined functionally as a nucleotide sequence that is capable of hybridizing with a portion of the target gene transcript.

Sequence identity can optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of particular target gene sequence is preferred. Alternatively, the duplex region of the RNA can be defined functionally as a nucleotide sequence that is capable of hybridizing with a portion of the particular target gene (e.g., 400 mM NaCl, 40 mM PIPES pH 6.4, 1 mM EDTA, 50° C. or 70° C. hybridization for 12-16 hours; followed by washing). The length of the identical nucleotide sequences may be at least 20, 25, 50, 100, 200, 300 or 400 bases. A 100% sequence identity between the RNA and Zscan4 is not required to practice the present methods.

For siRNA (RNAi), the RNA can be directly introduced into the cell (such as intracellularly); or introduced extracellularly into a cavity, interstitial space, into the circulation of an organism, introduced orally, or may be introduced by bathing an organism in a solution containing RNA. Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle can efficiently introduce an expression construct into the cell can provide transcription of RNA encoded by the expression construct. Other methods known in the art for introducing nucleic acids to cells may be used, such as lipid-mediated carrier transport, chemical-mediated transport, such as calcium phosphate, and the like. Thus, the RNA may be introduced along with components that perform one or more of the following activities: enhance RNA uptake by the cell, promote annealing of the duplex strands, stabilize the annealed strands, or other-wise increase inhibition of the target gene.

RNA may be synthesized either in vivo or in vitro. Endogenous RNA polymerase of the cell can mediate transcription in vivo, or cloned RNA polymerase can be used for transcription in vivo or in vitro. For transcription from a transgene in vivo or an expression construct, a regulatory region can be used to transcribe the RNA strand (or strands). RNA may be chemically or enzymatically synthesized by manual or automated reactions. The RNA may be synthesized by a cellular RNA polymerase or a bacteriophage RNA polymerase (for example, T3, T7, SP6). The use and production of expression constructs are known in the art (for example, PCT Publication No. WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA can be purified prior to introduction into the cell. For example, RNA can be purified from a mixture by extraction with a solvent or resin, precipitation, electrophoresis, chromatography, or a combination thereof. Alternatively, the RNA can be used with no or a minimum of purification to avoid losses due to sample processing. The RNA can be dried for storage or dissolved in an aqueous solution. The solution can contain buffers or salts to promote annealing, and/or stabilization of the duplex strands.

A polynucleotide encoding Zscan4 can be included in an expression vector to direct expression of the Zscan4 nucleic acid sequence. Thus, other expression control sequences including appropriate promoters, enhancers, transcription terminators, a start codon (i.e., ATG) in front of a protein-encoding gene, splicing signal for introns, maintenance of the correct reading frame of that gene to permit proper translation of mRNA, and stop codons can be included in an expression vector. Generally expression control sequences include a promoter, a minimal sequence sufficient to direct transcription.

The expression vector typically contains an origin of replication, a promoter, as well as specific genes which allow phenotypic selection of the transformed cells (e.g. an antibiotic resistance cassette). Vectors suitable for use include, but are not limited, to the pMSXND expression vector for expression in mammalian cells (Lee and Nathans, *J. Biol. Chem.* 263:3521, 1988). Generally, the expression vector will include a promoter. The promoter can be inducible or constitutive. The promoter can be tissue specific. Suitable promoters include the thymidine kinase promoter (TK), metallothionein I, polyhedron, neuron specific enolase, thyrosine hyroxylase, beta-actin, or other promoters. In one embodiment, the promoter is a heterologous promoter.

In one example, the polynucleotide encoding Zscan4 is located downstream of the desired promoter. Optionally, an enhancer element is also included, and can generally be located anywhere on the vector and still have an enhancing effect. However, the amount of increased activity will generally diminish with distance.

Expression vectors including a polynucleotide encoding Zscan4 can be used to transform host cells. Hosts can include isolated microbial, yeast, insect and mammalian cells, as well as cells located in the organism. Biologically functional viral and plasmid DNA vectors capable of expression and replication in a host are known in the art, and can be used to transfect any cell of interest. Where the cell is a mammalian cell, the genetic change is generally achieved by introduction of the DNA into the genome of the cell (i.e., stable) or as an episome. Thus, host cells can be used to produce Zscan4 polypeptides. Alternatively, expression vectors can be used to transform host cells of interest, such as stem cells.

A "transfected cell" is a cell into which (or into an ancestor of which) has been introduced, by means of recombinant DNA techniques, a DNA molecule encoding Zscan4. Transfection of a host cell with recombinant DNA may be carried out by conventional techniques as are well known in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such as a stem cell, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding Zscan4, and a second foreign DNA molecule encoding a selectable phenotype, such as neomycin resistance. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). Other specific, non-limiting examples of viral vectors include adenoviral vectors, lentiviral vectors, retroviral vectors, and pseudorabies vectors.

Differentiation can be induced, or proliferation decreased, of any cell, either in vivo or in vitro, using the methods disclosed herein. In one embodiment, the cell is a stem cell, such as, but not limited to, an embryonic stem cell, a germline stem cell or a multipotent adult progenitor cell. In several examples, a Zscan4 polypeptide, or a polynucleotide encoding the Zscan4 polypeptide, is introduced into a stem cell to decrease differentiation and/or increase proliferation.

In one example, the cells are stem cells, such as embryonic stem cells. For example, murine, primate or human cells can be utilized. ES cells can proliferate indefinitely in an undifferentiated state. Furthermore, ES cells are totipotent cells, meaning that they can generate all of the cells present in the body (bone, muscle, brain cells, etc.). ES cells have been isolated from the inner cell mass (ICM) of the developing murine blastocyst (Evans et al., *Nature* 292:154-156, 1981; Martin et al., *Proc. Natl. Acad. Sci.* 78:7634-7636, 1981; Robertson et al., *Nature* 323:445-448, 1986). Additionally, human cells with ES properties have been isolated from the inner blastocyst cell mass (Thomson et al., *Science* 282:1145-1147, 1998) and developing germ cells (Shamblott et al., *Proc. Natl. Acad. Sci. USA* 95:13726-13731, 1998), and human and non-human primate embryonic stem cells have been produced (see U.S. Pat. No. 6,200,806, which is incorporated by reference herein).

As disclosed in U.S. Pat. No. 6,200,806, ES cells can be produced from human and non-human primates. In one embodiment, primate ES cells are isolated "ES medium" that express SSEA-3; SSEA-4, TRA-1-60, and TRA-1-81 (see U.S. Pat. No. 6,200,806). ES medium consists of 80% Dulbecco's modified Eagle's medium (DMEM; no pyruvate, high glucose formulation, Gibco BRL), with 20% fetal bovine serum (FBS; Hyclone), 0.1 mM β-mercaptoethanol (Sigma), 1% non-essential amino acid stock (Gibco BRL). Generally, primate ES cells are isolated on a confluent layer of murine embryonic fibroblast in the presence of ES cell medium. In one example, embryonic fibroblasts are obtained from 12 day old fetuses from outbred mice (such as CF1, available from SASCO), but other strains may be used as an alternative. Tissue culture dishes treated with 0.1% gelatin (type I; Sigma) can be utilized. Distinguishing features of ES cells, as compared to the committed "multipotential" stem cells present in adults, include the capacity of ES cells to maintain an undifferentiated state indefinitely in culture, and the potential that ES cells have to develop into every different cell types. Unlike mouse ES cells, human ES (hES) cells do not express the stage-specific embryonic antigen SSEA-1, but express SSEA-4, which is another glycolipid cell surface antigen recognized by a specific monoclonal antibody (see, e.g., Amit et al., *Devel. Biol.* 227:271-278, 2000).

For rhesus monkey embryos, adult female rhesus monkeys (greater than four years old) demonstrating normal ovarian cycles are observed daily for evidence of menstrual bleeding (day 1 of cycle=the day of onset of menses). Blood samples are drawn daily during the follicular phase starting from day 8 of the menstrual cycle, and serum concentrations of luteinizing hormone are determined by radioimmunoassay. The female is paired with a male rhesus monkey of proven fertility from day 9 of the menstrual cycle until 48 hours after the luteinizing hormone surge; ovulation is taken as the day following the leutinizing hormone surge. Expanded blastocysts are collected by non-surgical uterine flushing at six days after ovulation. This procedure generally results in the recovery of an average 0.4 to 0.6 viable embryos per rhesus monkey per month (Seshagiri et al., *Am J Primatol.* 29:81-91, 1993).

For marmoset embryos, adult female marmosets (greater than two years of age) demonstrating regular ovarian cycles are maintained in family groups, with a fertile male and up to five progeny. Ovarian cycles are controlled by intramuscular injection of 0.75 g of the prostaglandin PGF2a analog cloprostenol (Estrumate, Mobay Corp, Shawnee, Kans.) during the middle to late luteal phase. Blood samples are drawn on day 0 (immediately before cloprostenol injection), and on days 3, 7, 9, 11, and 13. Plasma progesterone concentrations are determined by ELISA. The day of ovulation is taken as the day preceding a plasma progesterone concentration of 10 ng/ml or more. At eight days after ovulation, expanded blastocysts are recovered by a non-surgical uterine flush procedure (Thomson et al., *J Med Primatol.* 23:333-336, 1994). This procedure results in the average production of 1.0 viable embryos per marmoset per month.

The zona pellucida is removed from blastocysts, such as by brief exposure to pronase (Sigma). For immunosurgery, blastocysts are exposed to a 1:50 dilution of rabbit anti-marmoset spleen cell antiserum (for marmoset blastocysts) or a 1:50 dilution of rabbit anti-rhesus monkey (for rhesus monkey blastocysts) in DMEM for 30 minutes, then washed for 5 minutes three times in DMEM, then exposed to a 1:5 dilution of Guinea pig complement (Gibco) for 3 minutes. After two further washes in DMEM, lysed trophoectoderm cells are removed from the intact inner cell mass (ICM) by gentle pipetting, and the ICM plated on mouse inactivated (3000 rads gamma irradiation) embryonic fibroblasts.

After 7-21 days, ICM-derived masses are removed from endoderm outgrowths with a micropipette with direct observation under a stereo microscope, exposed to 0.05% Trypsin- EDTA (Gibco) supplemented with 1% chicken serum for 3-5 minutes and gently dissociated by gentle pipetting through a flame polished micropipette.

Dissociated cells are re-plated on embryonic feeder layers in fresh ES medium, and observed for colony formation. Colonies demonstrating ES-like morphology are individually selected, and split again as described above. The ES-like morphology is defined as compact colonies having a high nucleus to cytoplasm ratio and prominent nucleoli. Resulting ES cells are then routinely split by brief trypsinization or exposure to Dulbecco's Phosphate Buffered Saline (PBS, without calcium or magnesium and with 2 mM EDTA) every 1-2 weeks as the cultures become dense. Early passage cells are also frozen and stored in liquid nitrogen.

Cell lines may be karyotyped with a standard G-banding technique (such as by the Cytogenetics Laboratory of the University of Wisconsin State Hygiene Laboratory, which provides routine karyotyping services) and compared to published karyotypes for the primate species.

Isolation of ES cell lines from other primate species would follow a similar procedure, except that the rate of development to blastocyst can vary by a few days between species, and the rate of development of the cultured ICMs will vary between species. For example, six days after ovulation, rhesus monkey embryos are at the expanded blastocyst stage, whereas marmoset embryos do not reach the same stage until 7-8 days after ovulation. The rhesus ES cell lines can be obtained by splitting the ICM-derived cells for the first time at 7-16 days after immunosurgery; whereas the marmoset ES cells were derived with the initial split at 7-10 days after immunosurgery. Because other primates also vary in their developmental rate, the timing of embryo collection, and the timing of the initial ICM split, varies between primate species, but the same techniques and culture conditions will allow ES cell isolation (see U.S. Pat. No. 6,200,806, which is incorporated herein by reference for a complete discussion of primate ES cells and their production).

Human ES cell lines exist and can be used in the methods disclosed herein. Human ES cells can also be derived from preimplantation embryos from in vitro fertilized (IVF) embryos. Experiments on unused human IVF-produced embryos are allowed in many countries, such as Singapore and the United Kingdom, if the embryos are less than 14 days old. Only high quality embryos are suitable for ES isolation. Present defined culture conditions for culturing the one cell human embryo to the expanded blastocyst have been described (see Bongso et al., *Hum Reprod.* 4:706-713, 1989). Co-culturing of human embryos with human oviductal cells results in the production of high blastocyst quality. IVF-derived expanded human blastocysts grown in cellular co-culture, or in improved defined medium, allows isolation of human ES cells with the same procedures described above for non-human primates (see U.S. Pat. No. 6,200,806).

Precursor cells can also be utilized with the methods disclosed herein. The precursor cells can be isolated from a variety of sources using methods known to one skilled in the art. The precursor cells can be of ectodermal, mesodermal or endodermal origin. Any precursor cells which can be obtained and maintained in vitro can potentially be used in accordance with the present methods. Such cells include cells of epithelial tissues such as the skin and the lining of the gut, embryonic heart muscle cells, and neural precursor cells (Stemple and Anderson, 1992, Cell 71:973-985).

In one example, the cells are mesenchymal progenitor cells. Mesenchymal progenitors give rise to a very large number of distinct tissues (Caplan, J. Orth. Res 641-650, 1991). Mesenchymal cells capable of differentiating into bone and cartilage have also been isolated from marrow (Caplan, J. Orth. Res. 641-650, 1991). U.S. Pat. No. 5,226,914 describes an exemplary method for isolating mesenchymal stem cells from bone marrow.

In other examples, the cells are epithelial progenitor cells or keratinocytes can be obtained from tissues such as the skin and the lining of the gut by known procedures (Rheinwald, Meth. Cell Bio. 21A:229, 1980). In stratified epithelial tissue such as the skin, renewal occurs by mitosis of precursor cells within the germinal layer, the layer closest to the basal lamina. Precursor cells within the lining of the gut provide for a rapid renewal rate of this tissue. The cells can also be liver stem cells (see PCT Publication No. WO 94/08598) or kidney stem cells (see Karp et al., *Dev. Biol.* 91:5286-5290, 1994).

In one non-limited example, neuronal precursor cells are utilized. Undifferentiated neural stem cells differentiate into neuroblasts and glioblasts which give rise to neurons and glial cells. During development, cells that are derived from the neural tube give rise to neurons and glia of the CNS. Certain factors present during development, such as nerve growth factor (NGF), promote the growth of neural cells. Methods of isolating and culturing neural stem cells and progenitor cells are well known to those of skill in the art (Hazel and Muller, 1997; U.S. Pat. No. 5,750,376). Methods for isolating and culturing neuronal precursor cells are disclosed, for example, in U.S. Pat. No. 6,610,540.

V. Zscan4 and Trim43 Promoter Sequences

A Zscan4 promoter or a Trim43 promoter can be included in an expression vector to direct expression of a heterologous nucleic acid sequence. Other expression control sequences including appropriate enhancers, transcription terminators, a start codon (i.e., ATG) in front of a protein-encoding gene, splicing signal for introns, maintenance of the correct reading frame of that gene to permit proper translation of mRNA, and stop codons can be included with the Zscan4 or Trim43 promoter in an expression vector. Generally the promoter includes at least a minimal sequence sufficient to direct transcription of a heterologous nucleic acid sequence. In several examples, the heterologous nucleic acid sequence encodes a polypeptide. However, the heterologous nucleic acid can be any RNA sequence of interest, such as an inhibitory RNA.

Expression vectors typically contain an origin of replication as well as specific genes which allow phenotypic selection of the transformed cells. Vectors suitable for use include, but are not limited to the pMSXND expression vector for expression in mammalian cells (Lee and Nathans, *J. Biol. Chem.* 263:3521, 1988).

In one example, an enhancer is located upstream of the Zscan4 or Trim43 promoter, but enhancer elements can generally be located anywhere on the vector and still have an enhancing effect. However, the amount of increased activity will generally diminish with distance. Additionally, two or more copies of an enhancer sequence can be operably linked one after the other to produce an even greater increase in promoter activity.

Generally, an expression vector includes a nucleic acid sequence encoding a polypeptide of interest. A polypeptide of interest can be a heterologous polypeptide, such as a polypeptide that affects a function of the transfected cell. Polypeptides of interest include, but are not limited to, polypeptides that confer antibiotic resistance, receptors, oncogenes, and neurotransmitters. A polypeptide of interest can also be a marker polypeptide, which is used to identify a cell of interest. Marker polypeptides include fluorescent polypeptides, enzymes, or antigens that can be identified using conventional molecular biology procedures. For example, the polypeptide can be a fluorescent marker (such as green fluorescent protein, Emerald (Invitrogen, Carlsbad, Calif.), Strawberry (Clontech, Mountain View, Calif.), *Aequoria victoria*, or *Discosoma* DSRed); an antigenic marker (such as human growth hormone, human insulin, human HLA antigens); a cell-surface marker (such as CD4, or any cell surface receptor); or an enzymatic marker (such as lacZ, alkaline phosphatase). Techniques for identifying these markers in host cells include immunohistochemistry and fluorescent microscopy, and are well known in the art.

RNA molecules transcribed from an expression vector need not always be translated into a polypeptide to express a functional activity. Specific non-limiting examples of other molecules of interest include antisense RNA molecules complementary to an RNA of interest, ribozymes, small inhibitory RNAs, and naturally occurring or modified tRNAs.

Expression vectors including a Zscan4 or Trim43 promoter can be used to transform host cells. Hosts can include isolated microbial, yeast, insect and mammalian cells, as well as cells located in the organism. Biologically functional viral and plasmid DNA vectors capable of expression and replication in a host are known in the art, and can be used to transfect any cell of interest. Where the cell is a mammalian cell, the genetic change is generally achieved by introduction of the DNA into the genome of the cell (stable integration). However, the vector can also be maintained as an episome.

A "transfected cell" is a host cell into which (or into an ancestor of which) has been introduced, by means of recombinant DNA techniques, a DNA molecule including a Zscan4 promoter element. Transfection of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences including the Zscan4 promoter, and a second foreign DNA molecule encoding a selectable phenotype, such as neomycin resistance. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). Other specific, non-limiting examples of viral vectors include adenoviral vectors, lentiviral vectors, retroviral vectors, and pseudorabies vectors.

In one embodiment described in the Examples below, an expression vector comprising a Zsan4 promoter sequence operably linked to a heterologous polypeptide is used to identify cells that express Zscan4. In one embodiment, the Zscan4 promoter is a Zscan4c promoter. In some embodiments, the Zscan4c promoter comprises Zsan4c exon and/or intron sequence. The heterologous protein is typically a marker, an enzyme, or a fluorescent protein. In one embodiment, the heterologous protein is green fluorescent protein (GFP), or a variant of GFP, such as Emerald.

Provided herein is a method of identifying a subpopulation of stem cells expressing Zscan4. In one embodiment, the subpopulation is identified by transfecting the stem cells with an expression vector, wherein the expression vector comprises a Zscan4 promoter sequence and a reporter gene. In one embodiment, the Zscan4 promoter is a Zscan4c promoter. In another embodiment, the Zscan4c promoter comprises the nucleic acid sequence set forth as nucleotides 1-2540 of SEQ ID NO: 28, such as nucleotides 1-2643, 1-3250, or 1-3347 of SEQ ID NO: 28.

The reporter gene can be any type of identifiable marker, such as an enzyme or a fluorescent protein. In one embodiment, the reporter gene is GFP or a variant of GFP, such as Emerald. Expression of the reporter gene indicates the cell expresses Zscan4. Methods of detecting expression of the reporter gene vary depending upon the type of reporter gene and are well known in the art. For example, when a fluorescent reporter is used, detection of expression can be achieved by fluorescence activated cell sorting or fluorescence microscopy. Identification of a subpopulation of stem cells expressing Zscan4 can be achieved with alternative methods, including, but not limited to, using antibodies specific for Zscan4 or by in situ hybridization. In one embodiment, the subpopulation of ES cells expressing Zscan4 is identified by detecting expression of one or more Zscan4 co-expressed genes, including AF067063, Tcstv1/Tcstv3, Tho4, Arginase II, BC061212 and Gm428, Eif1a, EG668777 and Pif1.

Also described herein is an expression vector comprising a Trim43 promoter sequence operably linked to a heterologous polypeptide. The heterologous protein is typically a marker, an enzyme, or a fluorescent protein. In one embodiment, the heterologous protein is the fluorescent protein Strawberry. In some embodiments, the Trim43 promoter sequence is at least 70%, at least 80%, at least 90%, at least 95% or at least 99% identical to SEQ ID NO: 31. In another embodiment, the Trim43 promoter comprises SEQ ID NO: 31. In another embodiment, the Trim43 promoter consists of SEQ ID NO: 31.

Also provided herein are isolated ES cells comprising the Zscan4 or Trim43 expression vectors described herein. In one embodiment, the ES cells are a stable cell line.

VI. Transgenic Animals

The Zscan4 polynucleotide sequences disclosed herein can also be used in the production of transgenic animals such as transgenic mice, as described below. Transgenic animals can also be produced that contain polynucleotide sequences of one or more Zscan4 co-expressed genes, including AF067063, Tcstv1/Tcstv3, Tho4, Arginase II, BC061212 and Gm428, Eif1a, EG668777 and Pif1.

In one embodiment, a non-human animal is generated that carries a transgene comprising a nucleic acid encoding Zscan4 operably linked to a promoter. Specific promoters of use include, but are not limited to, a tissue specific promoter such as, but not limited to, an immunoglobulin promoter, a neuronal specific promoter, or the insulin promoter. Specific promoters of use also include a constitutive promoter, such as, but not limited to, the thymidine kinase promoter or the human β-globin minimal, or an actin promoter, amongst others. The Zscan4 promoter can also be used.

In another embodiment, the transgenic non-human animal carries a transgene comprising a nucleic acid encoding a heterologous peptide, such as a marker, enzyme or fluorescent protein, operably linked to a Zscan4 promoter. In one example, the Zscan4 promoter is a Zscan4c promoter, or a portion thereof. In another embodiment, the Zscan4c promoter comprises the nucleic acid sequence set forth as nucleotides 1-2540 of SEQ ID NO: 28, such as nucleotides 1-2643, 1-3250, or 1-3347 of SEQ ID NO: 28. In one example, the heterologous peptide is the fluorescent protein Emerald.

In another embodiment, the transgenic non-human animal carries a transgene comprising a nucleic acid encoding a heterologous peptide, such as a marker, enzyme or fluorescent protein, operably linked to a Trim43 promoter. In one example, the Trim43 promoter comprises the nucleotide sequence of SEQ ID NO: 31, or a portion thereof. The portion of SEQ ID NO: 31 to be included in the expression vector is at least a portion of SEQ ID NO: 31 that is capable of promoting transcription of the heterologous polypeptide in a cell in which Trim43 is expressed. In some embodiments, the Trim43 promoter sequence is at least 70%, at least 80%, at least 90%, at least 95% or at least 99% identical to SEQ ID NO: 31. In another embodiment, the Trim43 promoter comprises SEQ ID NO: 31. In another embodiment, the Trim43 promoter consists of SEQ ID NO: 31. In one example, the heterologous peptide is the fluorescent protein Strawberry.

In another embodiment, the transgenic non-human animal carries two transgenes, a transgene comprising the Zscan4 promoter linked to a nucleic acid sequence encoding a heterologous peptide, and a transgene comprising the Trim43 promoter linked to a nucleic acid sequence encoding a heterologous peptide, as described above. In some cases, the transgenic non-human animal is a mouse comprising the Zscan4 promoter transgene and the Trim43 promoter transgene. In one specific example, the heterologous polypeptide operably linked to the Zscan4 promoter sequence is the fluorescent protein Emerald and the heterologous polypeptide operably linked to the Trim43 promoter sequence is the fluorescent protein Strawberry. This mouse is referred to as a "rainbow" mouse (see Example 10 below).

Embryos obtained from transgenic "rainbow" animals exhibit green color at the late 2-cell stage and red color at the 4-cell to morula stages (with strongest expression at the morula stage). The expression of these colors at the proper timing and intensity indicates the progress of a correct genetic program, and thus, can be used as indicators of proper development of preimplantation embryos. These embryos have a variety of applications, including, but not limited to development of optimized culture media for human embryos for in vitro fertilization (IVF); training of technicians and clinicians in the IVF clinic and research laboratories; testing of chemical compounds and drugs for embryo toxicity; and as indicators of successful nuclear reprogramming for nuclear transplantation/cloning procedures.

The nucleic acid sequences described herein can be introduced into a vector to produce a product that is then amplified, for example, by preparation in a bacterial vector, according to conventional methods (see, for example, Sambrook et al., *Molecular Cloning: a Laboratory Manual*, Cold Spring Harbor Press, 1989). The amplified construct is thereafter excised from the vector and purified for use in producing transgenic animals.

Any transgenic animal can be of use in the methods disclosed herein, provided the transgenic animal is a non-human animal. A "non-human animal" includes, but is not limited to, a non-human primate, a farm animal such as swine, cattle, and poultry, a sport animal or pet such as dogs, cats, horses, hamsters, rodents, or a zoo animal such as lions, tigers or bears. In one specific, non-limiting example, the non-human animal is a transgenic animal, such as, but not limited to, a transgenic mouse, cow, sheep, or goat. In one specific, non-limiting example, the transgenic animal is a mouse. In a particular example, the transgenic animal has altered proliferation and/or differentiation of a cell type as compared to a non-transgenic control (wild-type) animal of the same species.

A transgenic animal contains cells that bear genetic information received, directly or indirectly, by deliberate genetic manipulation at the subcellular level, such as by microinjection or infection with a recombinant virus, such that a recombinant DNA is included in the cells of the animal. This molecule can be integrated within the animal's chromosomes, or can be included as extrachromosomally replicating DNA sequences, such as might be engineered into yeast artificial chromosomes. A transgenic animal can be a "germ cell line" transgenic animal, such that the genetic information has been taken up and incorporated into a germ line cell, therefore conferring the ability to transfer the information to offspring. If such offspring in fact possess some or all of that information, then they, too, are transgenic animals.

Transgenic animals can readily be produced by one of skill in the art. For example, transgenic animals can be produced by introducing into single cell embryos DNA encoding a marker, in a manner such that the polynucleotides are stably integrated into the DNA of germ line cells of the mature animal and inherited in normal Mendelian fashion. Advances in technologies for embryo micromanipulation permit introduction of heterologous DNA into fertilized mammalian ova. For instance, totipotent or pluripotent stem cells can be transformed by microinjection, calcium phosphate mediated precipitation, liposome fusion, retroviral infection or other means. The transformed cells are then introduced into the embryo, and the embryo then develops into a transgenic animal. In one non-limiting method, developing embryos are infected with a retrovirus containing the desired DNA, and a transgenic animal is produced from the infected embryo.

In another specific, non-limiting example, the appropriate DNA(s) are injected into the pronucleus or cytoplasm of embryos, preferably at the single cell stage, and the embryos are allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., *Manipulating the Mouse Embryo*, Cold Spring Harbor Press, 1986; Krimpenfort et al., *Bio/Technology* 9:86, 1991; Palmiter et al., *Cell* 41:343, 1985; Kraemer et al., *Genetic Manipulation of the Early Mammalian Embryo*, Cold Spring Harbor Laboratory Press, 1985; Hammer et al., *Nature* 315:680, 1985; Purcel et al., *Science* 244:1281, 1986; U.S. Pat. No. 5,175,385; U.S. Pat. No. 5,175,384.

VII. Antibodies

A Zscan4 polypeptide or a fragment or conservative variant thereof can be used to produce antibodies which are immunoreactive or specifically bind to an epitope of a Zscan4. Polyclonal antibodies, antibodies which consist essentially of pooled monoclonal antibodies with different epitopic specificities, as well as distinct monoclonal antibody preparations are included. In one embodiment, the Zscan4 antibodies recognize all Zscan4 proteins, including Zscan4a, Zscan4b, Zscan4c, Zscan4d, Zscan4e, Zscan4f and human ZSCAN4. In another embodiment, the antibodies specifically recognize only one Zscan4 protein. As used herein, the ability of an antibody to specifically a particular Zscan4 protein means that the antibody detects expression of one Zscan4 protein, but none of the other Zscan4 proteins. In an alternative embodiment, the antibodies recognize two or more different Zscan4 proteins. For example, a Zscan4 antibody may recognize only the Zscan4 proteins comprising a SCAN domain (e.g., Zscan4c, Zscan4d, Zscan4f). Or, a Zscan4 antibody may recognize only the Zscan4 proteins comprising the zinc finger domains, but lacking the SCAN domain (e.g., Zscan4a, Zscan4b, Zscan4e).

Antibodies can also be raised against one or more proteins encoded by genes identified herein as Zscan4 co-expressed genes. Thus, in some embodiments, a polypeptide encoded by AF067063, Tcstv1/Tcstv3, Tho4, Arginase II, BC061212 and Gm428, Eif1a, EG668777 or Pif1, or a fragment or conservative variant thereof, can be used to produce antibodies which are immunoreactive or specifically bind to an epitope of the polypeptide.

In addition, antibodies can be generated that specifically bind Trim43. In one embodiment, a Trim43 polypeptide, or a fragment or conservative variant thereof, can be used to produce antibodies which are immunoreactive or specifically bind to an epitope of Trim43.

The preparation of polyclonal antibodies is well known to those skilled in the art. See, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992.

The preparation of monoclonal antibodies likewise is conventional. See, for example, Kohler & Milstein, *Nature* 256: 495, 1975; Coligan et al., sections 2.5.1-2.6.7; and Harlow et al. in: *Antibodies: a Laboratory Manual*, page 726, Cold Spring Harbor Pub., 1988. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, such as syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from a subhuman primate antibody. General techniques for raising therapeutically useful antibodies in baboons can be found, for example, in PCT Publication No. WO 91/11465, 1991; and Losman et al., *Int. J. Cancer* 46:310, 1990.

Alternatively, an antibody that specifically binds a Zscan4 polypeptide can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. U.S.A.* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.

Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from STRATAGENE Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, F(ab')$_2$, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Natl. Acad. Sci. U.S.A.* 69:2659, 1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., *Methods: a Companion to Methods in Enzymology*, Vol. 2, page 106, 1991).

Antibodies can be prepared using an intact polypeptide or fragments containing small peptides of interest as the immunizing antigen. The polypeptide or peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (see, for example, Coligan et al., Unit 9, *Current Protocols in Immunology*, Wiley Interscience, 1991).

It is also possible to use the anti-idiotype technology to produce monoclonal antibodies which mimic an epitope. For example, an anti-idiotypic monoclonal antibody made to a first monoclonal antibody will have a binding domain in the hypervariable region that is the "image" of the epitope bound by the first mono-clonal antibody.

Binding affinity for a target antigen is typically measured or determined by standard antibody-antigen assays, such as competitive assays, saturation assays, or immunoassays such as ELISA or RIA. Such assays can be used to determine the dissociation constant of the antibody. The phrase "dissociation constant" refers to the affinity of an antibody for an antigen. Specificity of binding between an antibody and an antigen exists if the dissociation constant ($K_D=1/K$, where K is the affinity constant) of the antibody is, for example <1 µM, <100 nM, or <0.1 nM. Antibody molecules will typically have a $K_D$ in the lower ranges. $K_D=[Ab-Ag]/[Ab][Ag]$ where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds.

Effector molecules, e.g., therapeutic, diagnostic, or detection moieties can be linked to an antibody that specifically binds Zscan4, using any number of means known to those of skill in the art. Exemplary effector molecules include, but not limited to, radiolabels, fluorescent markers, or toxins (e.g. *Pseudomonas* exotoxin (PE), see "*Monoclonal Antibody-Toxin Conjugates: Aiming the Magic Bullet*," Thorpe et al., "Monoclonal Antibodies in Clinical Medicine," Academic Press, pp. 168-190, 1982; Waldmann, *Science,* 252: 1657, 1991; U.S. Pat. No. 4,545,985 and U.S. Pat. No. 4,894,443, for a discussion of toxins and conjugation). Both covalent and noncovalent attachment means may be used. The procedure for attaching an effector molecule to an antibody varies according to the chemical structure of the effector. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (e.g. enzymes or fluorescent molecules) drugs, toxins, and other agents to antibodies, one skilled in the art will be able to determine a suitable method for attaching a given agent to an antibody or other polypeptide.

The following examples are provided to illustrate certain particular features and/or embodiments. These examples should not be construed to limit the invention to the particular features or embodiments described.

EXAMPLES

The characterization of Zscan4 is disclosed herein. Zscan4 is shown herein to exhibit transient and specific expression at the late 2-cell embryonic stage and in embryonic stem cells. Without being bound by theory, Zscan4 is the only gene that is exclusively expressed during the first wave of de novo transcription, zygotic genome activation.

Zscan4 was identified from a cDNA clone derived from ES cells (clone number C0348C03) and subsequently sequenced by the Mammalian Gene Collection project (Gerhard et al. *Genom Res.* 14:2121-2127, 2004). The cDNA sequence, deposited under Genbank Accession No. BC050218 (SEQ ID NO: 11), comprised 2292 bp organized into 4 exons encoding a protein of 506 amino acids. As described in the Examples below, using this cDNA clone as a probe, a high level of Zscan4 transcript was detected in late 2-cell stage embryos. Since the original cDNA was isolated from ES cells, RT-PCR was performed on RNAs derived from late 2-cell stage embryos and the amplification product was sequenced, as described in the Examples below. The amplified sequence was 2268 bp in length and like the cDNA isolated from ES cells, encoded a protein of 506 amino acids. Analysis of the nucleotide and amino acid sequences of the cDNA clones isolated from ES cells and late 2-cell embryos showed they were two different, but similar genes.

As described in the Examples below, nine Zscan4 gene copies were identified in the mouse genome. Three copies are pseudogenes and were designated Zscan4-ps1 (SEQ ID NO: 12), Zscan4-ps2 (SEQ ID NO: 13) and Zscan4 ps3 (SEQ ID NO: 14), according to the convention of mouse gene nomenclature. The remaining six gene copies are transcribed and encode ORFs, thus they were named Zscan4a (SEQ ID NOs: 15 and 16), Zscan4b (SEQ ID NOs: 17 and 18), Zscan4c (SEQ ID NOs: 19 and 20), Zscan4d (SEQ ID NOs: 21 and 22), Zscan4e (SEQ ID NOs: 23 and 24) and Zscan4f (SEQ ID NOs: 25 and 26). Zscan4c, Zscan4d and Zscan4f encode proteins of 506 amino acids, while Zscan4a, Zscan4b and Zscan4e encode shorter proteins of 360, 195 and 195 amino acids, respectively. A polypeptide comprising any of the amino acid sequences set forth as SEQ ID NOs: 16, 18, 20, 22, 24, 26 or 30, or a polynucleotide encoding these polypeptides, are of use in the methods disclosed herein. A polynucleotide encoding a Zscan4 pseudogene set forth as SEQ ID NOs: 12, 13 or 14 are also of use in the methods disclosed herein.

Analysis of the expression levels of Zscan4 demonstrated that expression of each of the six Zscan4 genes could be detected in ES cells with Zscan4c being the predominant transcript. Zscan4d was the predominant transcript in 2-cell stage embryos; however, low levels of Zscan4a Zscan4e and Zscan4f could also be detected. These findings are consistent with the origin of each cDNA clone since Zscan4c was derived from the ES cell cDNA library and Zscan4d was derived from the 2-cell embryo cDNA library. Furthermore, expression of Zscan4 was not detected in blastocysts (including the inner cell mass) or early blastocyst outgrowth. After approximately six days of outgrowth, Zscan4 expression was detected in a subpopulation of undifferentiated ES cells.

It is shown herein that expression of Zscan4 is temporally regulated and its expression or lack of expression at different embryonic stages is critical to proper development. As described in the Examples below, inhibition of Zscan4 expression in embryos blocked the 2- to 4-cell embryonic transition, prevented blastocysts from expanding, prevented blastocysts from implanting and prevented proliferation of ES cells from blastocyst outgrowths.

Also described herein is the development of a mouse ES cell line expressing a heterologous protein, Emerald, under the control of a Zscan4 promoter. Further described is the identification of nine Zscan4 co-expressed genes exhibiting 2-cell stage specific expression.

Also shown herein is the identification of Trim43 as a gene exhibiting expression during the 4-cell to morula embryonic stages, with the highest level of expression observed at the morula stage. Also described herein is the development of a transgenic mouse, which comprises two transgenes, the first comprising Emerald operably linked to the Zscan4c promoter and the second comprising Strawberry operably linked to the Trim43 promoter.

Example 1

Materials and Methods

Identification and Cloning of the Mouse Zscan4d Gene

Using DNA microarray data of mouse preimplantation embryos (Hamatani et al., *Dev. Cell* 6:117-131, 2004), Zscan4d gene was identified for its specific expression in 2-cell embryos. A corresponding cDNA clone (no. C0348C03; R1 ES cells, 129 strain; Genbank Accession No. BC050218, SEQ ID NO: 11) was identified in the mouse cDNA collection described previously (Sharov et al., *PLoS Bio.* 1:E74, 2003). Based on this full-length cDNA sequence, a primer pair (5'-cctccctgggcttcttggcat-3', SEQ ID NO: 1; 5'-agctgccaaccagaaagacactgt-3', SEQ ID NO: 2) was designed and used to PCR-amplify the full-length cDNA sequence of this gene from 2-cell embryos (B6D2F1 mouse). In brief, mRNA was extracted from 2-cell embryos and treated with DNAase (DNA-free, Ambion). The mRNA was annealed with an oligo-dT primer and reverse-transcribed into cDNA with ThermoScript Reverse Transcriptase (Invitrogen). A full-length cDNA clone was PCR-amplified with Ex Taq Polymerase (Takara Minis Bio, Madison, Wis.), purified with the Wizard SV Gel and PCR Clean-Up System (Promega Biosciences, San Luis Obispo, Calif.), cloned into a pENTR plasmid vector with the Directional TOPO Cloning Kit (Invitrogen), and completely sequenced using BigDye Terminator kit (PE Applied Biosystems, Foster City, Calif.) and DyeEX 96 Kit (Qiagen Valencia, Calif.) on ABI 3100 Genetic Analyzer (PE Applied Biosystems). The sequence is set forth herein as SEQ ID NO: 21).

The WU-BLAST (available online) and UCSC genome browser were used to obtain Zscan4 orthologs in the human genome sequence. Open reading frames (ORFs) were deduced by ORF finder (available online from the National Center for Biotechnology Information) and protein domains were identified by Pfam HMM database (available online). Orthologous relationships were assessed with the phylogenetic tree of amino acid sequences determined by a sequence distance method and the Neighbor Joining (NJ) algorithm (Saitou and Nei, 1987) using Vector NTI software (Invitrogen, Carlsbad, Calif.).

All gene names and gene symbols were consulted with and approved by the mouse gene nomenclature committee.

Southern Blot Analysis

Southern blot analysis was carried out to validate the genome sequence of the Zscan4 locus assembled using individual BAC clone sequences downloaded from the public database (RPCI-23 and RPCI-24 BAC libraries: C57BL/6J strain). A probe containing exon 3 was designed and amplified from mouse DNA extracted from ES cells (C57BL/6) using a primer pair (5'-gcattcctacataccaatta-3', SEQ ID NO: 3; 5'-gatttaatttagctgggctg-3', SEQ ID NO: 4). The PCR product was purified using GFX PCR DNA and Gel band purification kit (GE Healthcare). Fifteen µg of mouse genomic DNA extracted from ES cells (BL6.9 line derived from C57BL/6 strain) was digested overnight with restriction enzymes (MspI, TaqI, and MspI/TaqI, see FIG. 3B), fractionated on a 1% (w/v) agarose gel, transferred and immobilized onto nitrocellulose membranes. Blots were hybridized with random-primed $^{32}$P-labeled DNA probes under standard conditions. Membranes were subjected to 3 washes of 30 min each (2×SSC/0.1% (w/v) SDS at room temperature, 0.5× SSC/0.1% (w/v) SDS at 42° C., and 0.1×SSC/0.1% (w/v) SDS at room temperature) and autoradiographed for 48 hours at −80° C.

Measurement of Gene Expression Levels cDNAs from ES cells (129.3 ES cells purchased from the Transgenic Core Laboratory of the Johns Hopkins University School of Medicine, Baltimore, Md.) and 2-cell embryos (B6D2F1 mice) were synthesized. Zscan4 cDNA fragments were amplified using a Zscan4-specific primer pair (Zscan4_For:5'-cagatgccagtagacaccac-3', SEQ ID NO: 5; Zscan4_Rev 5'-gtagatgttccttgacttgc-3', SEQ ID NO: 6), which were 100%-matched to all Zscan4 paralogs. These cDNA fragments were sequenced using the following primers: Zscan4_For, 5'-cagatgccagtagacaccac-3', SEQ ID NO: 5; Zscan4__400Rev, 5'-ggaagtgttatagcaattgttc-3', SEQ ID NO: 7; Zscan4_Rev, 5'-gtagatgttccttgacttgc-3', SEQ ID NO: 6; and Zscan4__300Rev, 5'-gtgttatagcaattgttcttg-3', SEQ ID NO: 8. Electropherograms of these sequences were used to calculate the relative expression levels of nine paralogous copies of Zscan4 in the following manner. Based on sequence information of transcripts (either predicted from the genome sequence or determined by sequencing cDNA clones), nucleotide positions were identified where one or a few paralogous copies can be distinguished based on the nucleotide mismatches. The phred base calling program (version 0.020425.c (Ewing et al., Genome Res. 8:175-185, 1998)) was used to obtain the amplitudes of all four bases in the electropherogram for those nucleotide sites. After subtracting the noise level (i.e., the average of amplitudes of the bases that are not present in any of the nine paralogous copies), the amplitudes of each base (A, T, G, C) were obtained. The expression levels of each of the paralogous copies were calculated by the least square fitting, which found the expression levels that are most consistent with all mismatched nucleotide positions.

Collection and Manipulation of Embryos

Four- to six-week old B6D2F1 mice were superovulated by injecting 5 IU pregnant mare serum gonadotropin (PMS; Sigma, St Louis, Mo., USA) and 5 IU human chorionic gonadotropin (HCG; Sigma) after 46-47 h (Protocol#220MSK-Mi approved by the National Institute on Aging Animal Care and Use Committee). Unfertilized eggs were harvested at 21 h post-HCG according to the standard method (Nagy et al., 2003, "Manipulation of the Mouse Embryo, A Laboratory Manual," Cold Spring Harbor Laboratory Press, New York). After removing cumulus cells by incubation in M2 medium (MR-015-D) supplemented with bovine testicular hyaluronidase (HY, 0.1% (w/v), 300 Umg-1), unfertilized eggs were thoroughly washed, selected for good morphology and collected. Fertilized eggs (1-cell embryos) were also harvested from mated superovulated mice in the same way as unfertilized eggs. Fertilized eggs (1-cell embryos) were cultured in synthetic oviductal medium enriched with potassium (KSOMaa MR-121-D) at 37° C. in an atmosphere of 5% CO2. For the embryo transfer procedure, 3.5 d.p.c. blastocysts were transferred into the uteri of 2.5 d.p.c. pseudopregnant ICR female mice.

To synchronize in vitro embryo development, embryos with two pronuclei (PN) were selected. When some of these 1-cell stage embryos started to cleave, the early 2-cell stage embryos were selected and transferred to another microdrop culture. The early 2-cell stage embryos were cultured until some of them started $2^{nd}$ cleavage and the embryos that were still at the 2-cell stage were collected. These embryos were synchronized at the late 2-cell stage.

DNA was microinjected into embryos according to the following procedures.

(1) Pronuclear injection: Plasmid vectors constitutively expressing a siRNA against mouse Zscan4 were constructed by inserting the following target sequences in a pRNAT-U6.1/Neo vector (GenScript Corp., Scotch Plains, N.J., USA), shZscan4 (gagtgaattgctttgtgtc, SEQ ID NO: 9) and siControl (randomized 21-mer, agagacatagaatcgcacgca, SEQ ID NO: 10). This vector contains a green fluorescence protein (GFP) marker under a cytomegalovirus (CMV) promoter. For RNA interference experiments, 1-2 pl (2-3 ng/µl) of a linearized vector DNA (shZscan4 or shControl) was microinjected into the male pronucleus of zygotes. A plasmid vector constitutively expressing the Zscan4d gene was constructed by cloning the CDS of Zscan4d into a plasmid pPyCAGIP (Chambers et al., Cell 113:643-655, 2003). For overexpression experiments, 1-2 pl (2-3 ng/l) of plasmid DNA (Zscan4d-inserted or no insert pPyCAGIP vector) linearized by ScaI was microinjected into the male pronucleus of zygotes.

(2) Cytoplasmic injection: Transient RNA interference experiments were carried out by microinjecting ~10 pl (5 ng/µl) of oligonucleotide (siZscan4, plus-siZscan4, and siControl) into the cytoplasm of zygotes. The optimal amount of siRNA was determined by testing different concentrations of siRNA (4, 20, and 100 ng/µl).

All siRNAs were resuspended and diluted with the microinjection buffer (Specialty Media). The transfer of cultured blastocysts into pseudopregnant recipients was done according to the standard protocol (Nagy et al., 2003, "Manipulation of the Mouse Embryo, A Laboratory Manual," Cold Spring Harbor Laboratory Press, New York). All media were purchased from Specialty Media (Phillipsburg, N.J.).

Culture of ES Cells and Blastocyst Outgrowth

A mouse ES cell line (129.3 line derived from strain 129 and purchased from The Transgenic Core Laboratory of the Johns Hopkins University School of Medicine, Baltimore, Md., USA) was first cultured for two passages into a gelatin-coated culture dish in the presence of leukemia inhibitory factor (LIF) to remove contaminating feeder cells. Cells were then seeded on gelatin coated 6-well plates at the density of $1-2 \times 10^5$/well ($1-2 \times 10^4$/cm$^2$) and cultured for 3 days with complete ES medium (DMEM, 15% FBS; 1000 U/ml ESGRO (mLIF; Chemicon, Temecula, Calif.); 1 mM sodium pyruvate; 0.1 mM NEAA; 2 mM glutamate; 0.1 mM beta-mercapto ethanol and 50 U/50 μg per ml penicillin/streptomycin).

For the outgrowth experiments, blastocysts at 3.5 days post coitum (d.p.c.) were cultured individually in DMEM (Gibco catalog no. 10313-021) supplemented with 15% fetal bovine serum, 15 mM HEPES buffer, 100 units/ml of penicillin, 100 μg/ml of streptomycin, 100 μM nonessential amino acids, 4.5 mM of L-glutamine, and 100 μM of β-mercapto ethanol on gelatinized chamber slides at 37° C. in 5% CO2.

Whole Mount In Situ Hybridization (WISH)

A plasmid DNA (clone C0348C03) was digested with SalI/NotI and transcribed in vitro into digoxigenin-labeled antisense and sense probe as control. Embryos obtained from young (7 weeks old) B6D2F1a mice were fixed in 4% paraformaldehyde and used to perform whole mount in situ hybridization (WISH) according to the previously described protocol. WISH was also carried out on cultured ES cells according to the same protocol (Yoshikawa et al., *Gene Expr. Patterns* 6:213-224, 2006).

Quantitative Reverse Transcriptase PCR

Embryos for quantitative reverse transcriptase (qRT)-PCR experiments were collected as described above and harvested at 23, 43, 55, 66, 80 and 102 hours post-hCG for 1-cell, early 2 cell, late 2-cell, 4-cell, 8-cell, morula and blastocyst embryos, respectively. Three subsets of 10 synchronized and intact embryos were transferred in PBT 1X (PBS supplemented 0.1% Tween X20) and stored in liquid nitrogen. These pools of embryos were mechanically ruptured by a freeze/thaw and directly used as a template for cDNA preparations. The Ovation system (NuGen technologies, San Carlos, Calif., USA) was used to synthesize cDNAs from each pool. The cDNAs were then diluted to 1:25 in a total of 1000 μl and 2 μl was used as a template for qPCR. The qPCR was performed on the ABI 7900HT Sequence Detection System (Applied Biosystems, Foster City, Calif., USA) as previously described (Falco et al., *Reprod. Biomed. Online* 13:394-403, 2006) and data were normalized by Chuk and H2afz with the ΔΔCt method (Falco et al., *Reprod. Biomed. Online* 13:394-403, 2006; Livak and Schmittgen, *Methods* 25:402-408, 2001). Embryos subjected to RNA interference experiments were analyzed in the same way as described above for the normal preimplantation embryos Example 2

Identification of 2-Cell-Specific Genes During Preimplantation Development

After fertilization, the maternal genetic program governed by maternally stored RNAs and proteins must be switched to the embryonic genetic program governed by de novo transcription, called zygotic genome activation (ZGA), from the newly-formed zygotic genome (DePamphilis et al., "Activation of Zygotic Gene Expression" In Advances in Developmental Biology and Biochemistry, Vol. 12, pp. 56-84, Elsevier Science B.V., 2002; Latham and Schultz, *Front Biosci.* 6:D748-759, 2001). The ZGA is one of the first and most critical events in animal development. Earlier reports have established that the ZGA begins during the 1-cell stage (Aoki et al., *Dev. Biol.* 181:296-307, 1997) (Nothias et al., *J. Biol. Chem.* 270:22077-22080, 1995; Ram and Schultz, *Dev. Biol.* 156:552-556, 1993). However, global gene expression profiling by DNA microarray analysis has recently revealed that nearly all genes identified for their increase of expression at the 1-cell stage were insensitive to alpha-amanitin treatment, which blocks RNA polymerase II (Hamatani et al., *Dev. Cell* 6:117-131, 2004; Zeng and Schultz, *Dev. Biol.* 283:40-57, 2005). Thus, these studies not only identified many ZGA genes, but also revealed that de novo transcription of the zygotic genome begins during the 2-cell stage of mouse preimplantation development (Hamatani et al., *Dev. Cell* 6:117-131, 2004; Zeng and Schultz, *Dev. Biol.* 283:40-57, 2005). Furthermore, it has been shown that the major burst of ZGA does not occur at the early 2-cell stage, but during the late 2-cell stage (Hamatani et al., *Dev. Cell* 6:117-131, 2004).

Arrest of development at the 2-cell stage has been reported for the loss-of-function mutants of Mater/Nalp5 (Tong et al., *Nat. Genet.* 26:267-268, 2000), Mhr6a/Ube2a (Roest et al., *Mol. Cell. Biol.* 24:5485-5495, 2004) and Brg1/Smarca4 (Bultman et al., *Genes Dev.* 20:1744-1754, 2006). Although the timing of the developmental arrest coincides with that of the ZGA, these genes are expressed during oogenesis and stored in oocytes, but are not transcribed in the 2-cell stage. Therefore, these maternal effect genes are not suitable for the study of the ZGA. Previously the ZGA has been studied using either exogenous plasmid-borne reporter genes Nothias et al., *J. Biol. Chem.* 270:22077-22080), or endogenous, but rather ubiquitously expressed genes, such as Hsp70.1 (Christians et al., 1995), eIF-4C (Davis et al., *Dev. Biol.* 174:190-201, 1996), Xist (Zuccotti et al., *Mol. Reprod. Dev.* 61:14-20, 2002) and other genes (DePamphilis et al., "Activation of Zygotic Gene Expression" In Advances in Developmental Biology and Biochemistry, Vol. 12, pp. 56-84, Elsevier Science B.V., 2002). Although TEAD-2/TEF-4 (Kaneko et al., *Development* 124:1963-1973, 1997) and Pou5f1/Oct4 (Palmieri et al., *Dev. Biol.* 166:259-267, 1994) are considered as transcription factors selectively expressed at ZGA (DePamphilis et al., "Activation of Zygotic Gene Expression" In Advances in Developmental Biology and Biochemistry, Vol. 12, pp. 56-84, Elsevier Science B.V., 2002), these genes are known to be expressed in cells other than 2-cell embryos. It is thus important to identify and study individual ZGA genes, especially the genes expressed exclusively at the 2-cell stage.

Global gene expression profiling of preimplantation embryos was previously carried out and a group of genes was identified that showed transient spike-like expression in the 2-cell embryo (Hamatani et al., *Dev. Cell* 6:117-131, 2004). By examining the expression of these genes in the public expressed sequence tag (EST) database (NCBI/NIH), a novel gene was identified represented by only 29 cDNA clones out of 4.7 million mouse ESTs. These cDNA clones have been isolated from cDNA libraries derived from ES cells and preimplantation embryos. Furthermore, the previous DNA microarray data showed that the expression of this gene is detected in ES cells, but not in embryonal carcinoma (EC) cells (F9 and P19), trophoblast stem (TS) cells, or neural stem/progenitor (NS) cells (Aiba et al., *Stem Cells* 24:889-895, 2006).

Figure 1B:
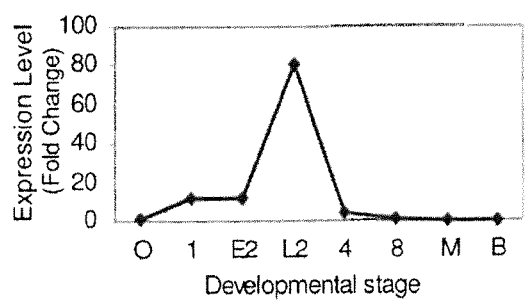
FIG. 1B shows a graph of the expression levels of Zscan4 during preimplantation development quantitated by qRT-PCR analysis. Three sets of 10 pooled embryos were collected from each stage (O, oocyte; 1, 1-cell embryo; E2, early 2-cell embryo; L2, late 2-cell embryo; 4, 4-cell embryo; 8, 8-cell embryo; M, morula; and B, blastocyst) and used for qRT-PCR analysis. The expression levels of Zscan4 were normalized to Chuk control, and the average expression levels at each stage are represented as a fold change compared to the expression level in oocytes.

One of the cDNA clones derived from ES cells (clone number C0348C03; (Sharov et al., *PLoS Biol.* 1:E74, 2003)) was completely sequenced by the Mammalian Gene Collection (MGC) project (Genbank Accession No. BC050218; SEQ ID NO: 11 (Gerhard et al., *Genome Res.* 14:2121-2127, 2004)). Whole mount in situ hybridization (WISH) using this cDNA clone as a probe detected high level of transcripts in late 2-cell embryos (FIG. 1A). The transcript was not detected in unfertilized eggs and embryos in other preimplantation stages including 3-cell embryos, suggesting a high specificity of gene expression at the late 2-cell stage and a relatively short half-life of the transcripts. Quantitative reverse-transcriptase PCR (qRT-PCR) analysis confirmed the WISH results (FIG. 1B). Previous microarray analysis showed that the expression of this gene at the late 2-cell stage was suppressed in embryos treated with α-amanitin (a blocker of RNA pol II-based transcription) (Hamatani et al., *Dev. Cell* 6:117-131, 2004), confirming that this gene is transcribed de novo during the major burst of ZGA. The transient expression pattern was observed in both in vitro cultured embryos and freshly isolated in vivo embryos (Hamatani et al., *Dev. Cell* 6:117-131, 2004).

Example 3

Structure and Expression of Zscan4 Paralogous Genes

The full-length cDNA sequence (BC050218; SEQ ID NO: 11) of 2292 bp was organized into 4 exons, encoding a protein of 506 amino acids (FIG. 2A). Because this cDNA clone was isolated from a cDNA library made from ES cells (Sharov et al., *PLoS Biol.* 1:E74, 2003), another cDNA clone was isolated by performing RT-PCR on RNAs isolated from late 2 cell-stage embryos and completely sequenced (SEQ ID NO: 21). This 2268 bp cDNA clone encoded a protein of 506 amino acids. DNA sequence and protein sequences clearly showed that these two cDNAs (SEQ ID NOs: 11 and 21) were two different genes with close similarity. Domain prediction analysis revealed a SCAN (Leucine Rich Element) domain and four zinc finger domains at the N- and C-terminal ends, respectively (FIG. 2B). A hypothetical human ortholog—zinc finger and SCAN domain containing 4 (ZSCAN4) was also identified that shares 45% of amino acid sequence similarity with the high conservation in SCAN (50%) and zinc finger domains (59%) (FIG. 7).

Figure 8:
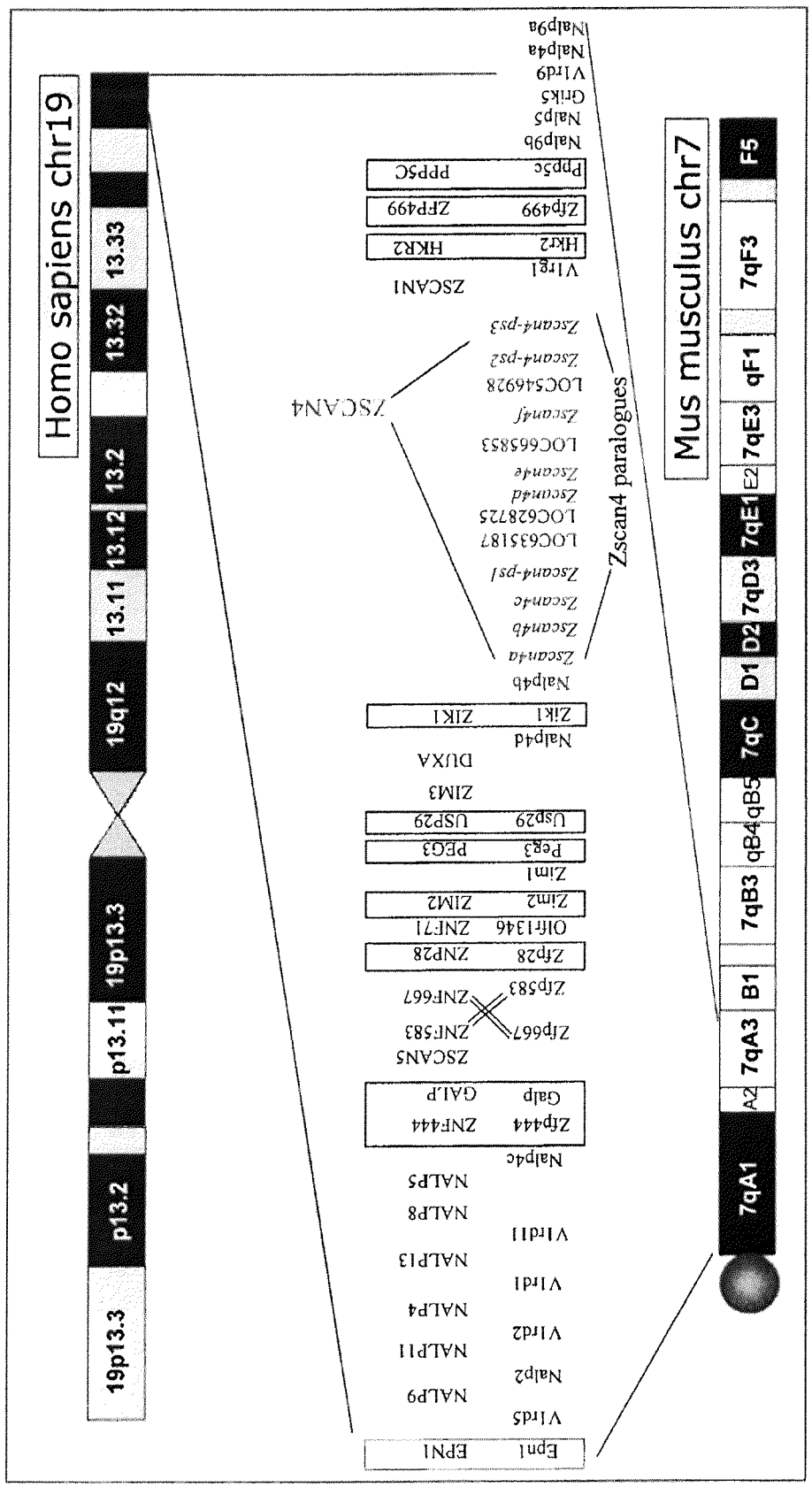
FIG. 8 is an illustration showing the Zscan4 syntenic regions of mouse and human genomes.

Alignment of full-length cDNA sequences (SEQ ID NOs: 11 and 21) to the mouse genome sequence (mm7) revealed multiple hits in the proximal region of chromosome 7, the syntenic region of human ZSCAN4 (FIG. 8). One notable feature of this genome region was repetitions of a very similar sequence segment. The sequences of each copy of Zscan4 and the surrounding region were very similar to each other, leaving the assembled genome sequences of this region less accurate than those of other regions. To understand the genome structure of this region better, individual BAC clone sequences were manually reassembled from this region into ~850 kb genome sequence contigs (FIG. 3A). Because it was difficult to find a hybridization probe or oligonucleotides to distinguish each copy, restriction enzymes were used that can distinguish small sequence differences among gene copies. Southern blot analysis was carried out by digesting C57BL/6J mouse genomic DNAs with TaqI alone, MspI alone, or TaqI/MspI (FIGS. 3B and C). All the detected DNA fragments confirmed nine paralogous Zscan4 genes predicted in the assembled genome sequences.

The full-length cDNA sequence (BC050218; SEQ ID NO: 11) was then aligned to the assembled genome sequence and nine gene copies were found, all of which had multi-exon gene organizations (FIGS. 2, 3A). Three gene copies were apparently pseudogenes as no evidence was found that they were transcribed based on available EST information and sequencing analysis of RT-PCR products. Therefore, the genes were named Zscan4-ps1 (SEQ ID NO: 12), Zscan4-ps2 (SEQ ID NO: 13), and Zscan4-ps3 (SEQ ID NO: 14), according to the convention of mouse gene nomenclature. Because the remaining 6 gene copies were transcribed and encoded ORFs, they were named Zscan4a (SEQ ID NO: 15), Zscan4b (SEQ ID NO: 17), Zscan4c (SEQ ID NO: 19), Zscan4d (SEQ ID NO: 21), Zscan4e (SEQ ID NO: 23) and Zscan4f (SEQ ID NO: 25). Three of the these genes, Zscan4a, Zscan4b, and Zscan4e, encoded ORFs of 360, 195 and 195 amino acids, respectively, which included the SCAN domain, but not the four zinc finger domains (FIG. 2B).

The remaining three genes, Zscan4c, Zscan4d and Zscan4f, encoded full-length ORFs (506 amino acids). The main features of these genes are summarized in FIG. 3A. Zscan4c corresponds to the cDNA clone isolated from ES cells (C0348C03; Genbank Accession No. BC050218; Gm397; SEQ ID NO: 11). Zscan4d corresponds to the cDNA clone isolated from 2-cell embryos (SEQ ID NO: 21). Zscan4f corresponds to a gene predicted from the genome sequence (Genbank Accession No. XM_145358; SEQ ID NO: 27). Similarities of both ORFs and mRNAs between these three genes were very high (FIG. 7). Thus, it is most likely that these three genes have the same function. To measure the expression levels of each paralog, DNA sequences of the nine Zscan4 paralogs were analyzed by the Clustal X multiple-sequence alignment program, which showed the presence of sequence differences specific to each paralog. To examine the expression levels of each gene in 2-cell embryos and ES cells, cDNA fragments amplified by RT-PCR from 2-cell embryos and ES cells were sequenced. The expression level of each paralog were estimated based on the amplitudes of each nucleotide at polymorphic sites. The results are summarized in FIG. 3A. In 2-cell embryos, Zscan4d was a predominant transcript (90%). In contrast, in ES cells, Zscan4c was a predominant transcript (40%), although Zscan4f was a lesser, but significant transcript (24%). These results were consistent with the origin of each cDNA clone; Zscan4c was derived from the ES cell cDNA library, whereas Zscan4d was derived from the 2-cell embryo library.

Example 4

Function of Zscan4 in Preimplantation Development

As a first step to characterize the function of Zscan4 genes, the studies focused on preimplantation development. Initially a possibility to carry out a standard gene targeting strategy was explored, but it was difficult for the following three reasons. First, sequences of Zscan4 paralogs and surrounding genomic regions are too similar to design targeting constructs for specific genes. Second, it is highly likely that Zscan4d$^{-/-}$ phenotype can be compensated functionally by other Zscan4 paralogs, because in addition to predominantly-expressed Zscan4d, at least 3 other similar copies (Zscan4a, Zscan4e, and Zscan4f) were also transcribed in 2-cell embryos. Third, the presence of other predicted genes, though not annotated as genes yet, within ~850 kb Zscan4 locus makes a strategy to delete the entire Zscan4 locus less attractive. Therefore, siRNA technology was used. Although RNAi and siRNA technology has been successfully used for blocking the expression of specific genes in preimplantation embryos (Kim et al., *Biochem. Biopys. Res. Commun.* 296:1372-1377, 2002; Stein et al., *Dev. Biol.* 286:464-471, 2005), widely-recognized off-target effects are generally a major concern (Jackson et al., *Rna* 12:1179-1187, 2006; Scacheri et al., *Proc. Natl. Acad. Sci. U.S.A.* 101:1892-1897, 2004; Semizarov et al., *Proc. Natl. Acad. Sci. U.S.A.* 100:6347-6352, 2003). To increase the confidence of the effects by siRNA against Zscan4, the siRNA experiments were carried out by three independent siRNA technologies, an oligonucleotide-based siRNA (denoted here siZscan4 and obtained from Invitrogen); a vector-based shRNA (denoted here shZscan4 and obtained from Genscript); and a mixture of oligonucleotide siRNAs (denoted here plus-siZscan4 and obtained from Dharmacon) (FIGS. 4A, B). Oligonucleotide sequences used for siZscan4, shZscan4, plus-siZscan4 matched 100% with cDNA sequences of Zscan4a, Zscan4b, Zscan4c, Zscan4d, Zscan4e and Zscan4f, except for shZscan4 with 2 bp mismatches with Zscan4b and Zscan4e (FIG. 4A, B).

Figures 9A, 9B:
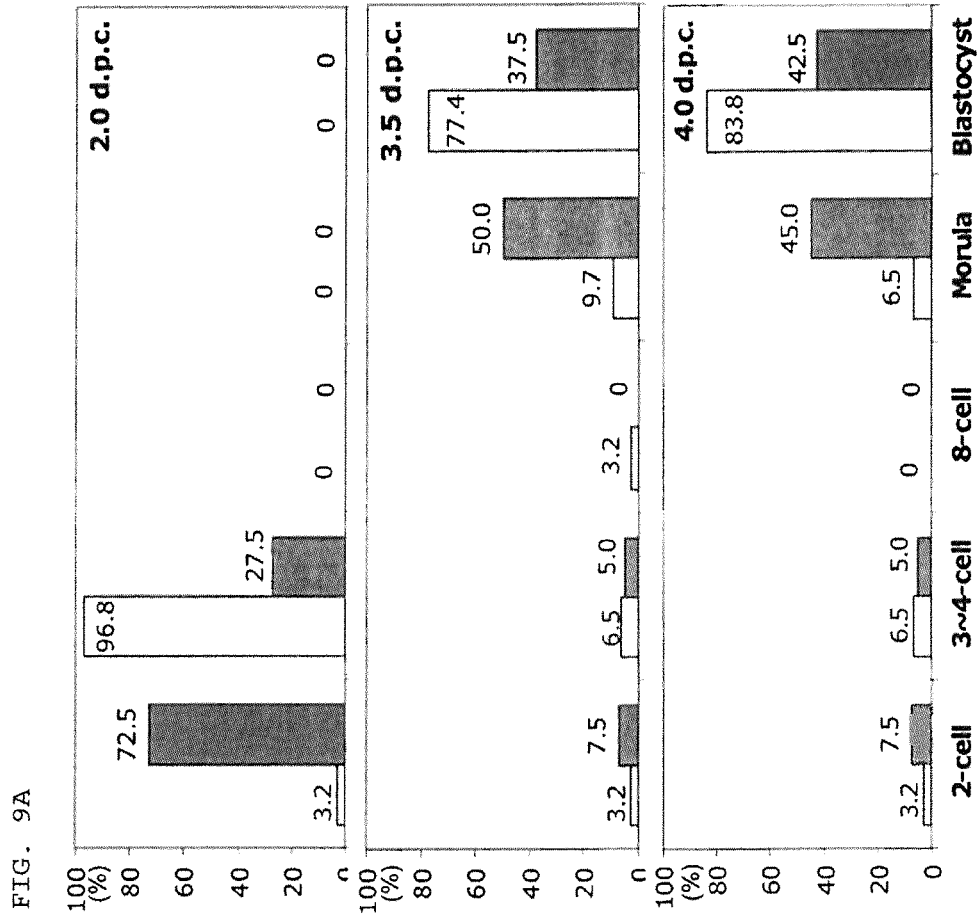
FIGS. 9A-9B is a series of graphs and photographs showing the development of embryos that received a siZscan4-injection in the cytoplasm.

A shZscan4 vector was microinjected into the male pronucleus of zygotes at 21-23 hours after the hCG injection and embryos were observed during preimplantation development (FIGS. 4C and D). At 61 hours post-hCG, when the majority (58.8%) of shControl-injected embryos have already reached the 4-cell stage, the majority (78.8%) of shZscan4-injected embryos remained at the 2-cell stage. By 98 hours post-hCG, when the majority (70.0%) of shControl-injected embryos have reached blastocyst stage, the majority (52.5%) of shZscan4-injected embryos reached only morula stage. A significant reduction (~95%) of Zscan4 RNA levels was confirmed by the qRT-PCR analysis (FIG. 4E). Taken together, these results indicate that the development of shZscan4-injected embryos was delayed for about 24 hrs between the 2- and 4-cell stages, followed by progression to the later stages at a speed comparable to that of shControl-injected embryos. Essentially the same results were obtained using two different siRNA technologies: siZscan4 (FIG. 9) and plus-siZscan4 (FIG. 10).

siZscan4-injected embryos formed normal looking early blastocysts (3.5 d.p.c.), but often failed to form expanded blastocysts (4.5 d.p.c.; 45% of siZscan4-injected embryos versus 6% of siControl-injected embryos; FIG. 9B). To test whether these blastocysts had any compromise even at 3.5 d.p.c., shZscan4-injected blastocysts were transferred to the uterus of pseudo-pregnant mice. None of the shZscan4-injected blastocysts implanted, whereas most shControl-injected embryos implanted (Table 1). In vitro blastocyst outgrowth experiments determined that cells of shZscan4-injected blastocysts failed to proliferate in culture (Table 1). These results clearly demonstrated that the transient expression of Zscan4 at the late 2-cell stage is required for the development of proper blastocysts.

TABLE 1

Blastocyst outgrowth (A) and post-implantation development (B) of embryos received pronuclear injection of shZscan4 or shControl

| A Blastocyst Outgrowth | Number of tested blastocysts | Number of successful outgrowth |
|---|---|---|
| shZscan4 | 16 | 0 |
| shControl | 17 | 7 |

TABLE 1-continued

Blastocyst outgrowth (A) and post-implantation development (B) of embryos received pronuclear injection of shZscan4 or shControl

| B Embryo Transfer | Number of blastocysts transferred to pseudo-pregnant mother | Number of pups born |
|---|---|---|
| shZscan4 | 8 | 0 |
| shControl | 10 | 4 |

*A shZscan4 or shControl vector was microinjected into the male pronucleus of zygotes at 21-23 hours after the hCG injection. Early blastocysts (3.5 d.p.c.) formed from these embryos were subjected to tests of blastocysts outgrowth (A) and embryo transfer (B). In the outgrowth assay, the presence of proliferating cells after 6 days in culture was considered as successful outgrowth.

The notion that the reduction of Zscan4 expression level delays the development of preimplantation embryos at the 2-cell stage was further supported by the fact that when shZscan4 was injected into one of the blastomeres of early 2-cell stage embryos, ~28% of embryos became 3-cell embryos (FIG. 5A). One blastomere that received shZscan4 injection remained as a 2-cell blastomere, whereas the other blastomere cleaved into two smaller blastomeres with the size of 4-cell blastomeres (FIG. 5D). Subsequently, these embryos (24%) became unevenly cleaved embryos, typically 5-cell embryos, with one 2-cell-sized blastomere and four 8-cell-sized blastomeres (FIG. 5B, E). These embryos eventually formed blastocyst-like structures, but they seemed to be the mixtures of blastocyst-like cell mass and morula-like cell mass, which was often GFP-positive, a marker for shRNA-injected blastomere (FIG. 5C, F, G). In contrast, when shControl was injected into one of the blastomeres at the early 2-cell stage, nearly all embryos cleaved normally (FIGS. 5A, B, C).

To investigate the effect of prolonged Zscan4d expression on preimplantation development, Zscan4d was overexpressed by microinjecting a Zscan4d-expressing plasmid into the male pronucleus of zygotes. Although the Zscan4d plasmid-injected embryos showed a rate of development similar to control plasmid-injected embryos, the former blastocysts failed to produce the outgrowth (Table 2A) and failed to implant (Table 2B). The results suggest that the timely down-regulation of Zscan4d is also important for the proper development of blastocysts.

TABLE 2

Blastocyst outgrowth (A) and post-implantation development (B) of embryos received pronuclear injection of a Zscan4d-expressing plasmid or a control plasmid

| A Blastocyst Outgrowth | Number of tested blastocysts | Number of successful outgrowth |
|---|---|---|
| Zscan4d-expressing plasmid | 10 | 2 |
| Control plasmid | 15 | 11 |

| B Embryo Transfer | Number of blastocysts transferred to pseudo-pregnant mother | Number of pups |
|---|---|---|
| Zscan4d-expressing plasmid | 10 | 0 |
| Control plasmid | 14 | 5 |

*A plasmid vector constitutively expressing Zscan4d gene or control empty vector was microinjected into the male pronucleus of zygotes at 21-23 hours after the hCG injection. Early blastocysts (3.5 d.p.c.) formed from these embryos were subjected to the same tests as described in Table 1.

Example 5

Analysis of Zscan4 Expression Using the Whole Mount In Situ Hybridization (WISH)

One intriguing aspect of the expression pattern of Zscan4 is the exclusive expression in late 2-cell embryos and ES cells. This appears to be counter-intuitive, because ES cells are derived from the ICM and many genes that are expressed in ES cells are also expressed in the ICM (e.g., Yoshikawa et al., Gene Expr. Patterns 6:213-224, 2006). Therefore the expression of Zscan4 in blastocysts, blastocyst outgrowth, and ES cells was examined using WISH. The results demonstrated that the expression of Zscan4 was not detected anywhere in blastocysts, including the ICM and the early blastocyst outgrowth (FIG. 6A). However, the expression of Zscan4 began to be detected in a small fraction of cells by the day 6 of the outgrowth. Surprisingly, the strong expression of Zscan4 was detected in only a small fraction of ES cells in undifferentiated colonies. In contrast, the expression of Pou5f1 (Oct3/4), a well-known marker for pluripotency, was detected in the ICM of blastocysts, a large fraction of the cells in the blastocyst outgrowth, and the majority of ES cells in undifferentiated colonies (FIG. 6A). Due to the close similarity of cDNA sequences, each Zscan4 paralog could not be distinguished by WISH, but the expression analysis by sequencing RT-PCR products mentioned above indicates that Zscan4c and Zscan4f were the genes detected in the subpopulation of the cells in blastocyst outgrowth and ES cells by WISH.

Example 6

Zscan4 Promoter Expression Vector

Figure 11:
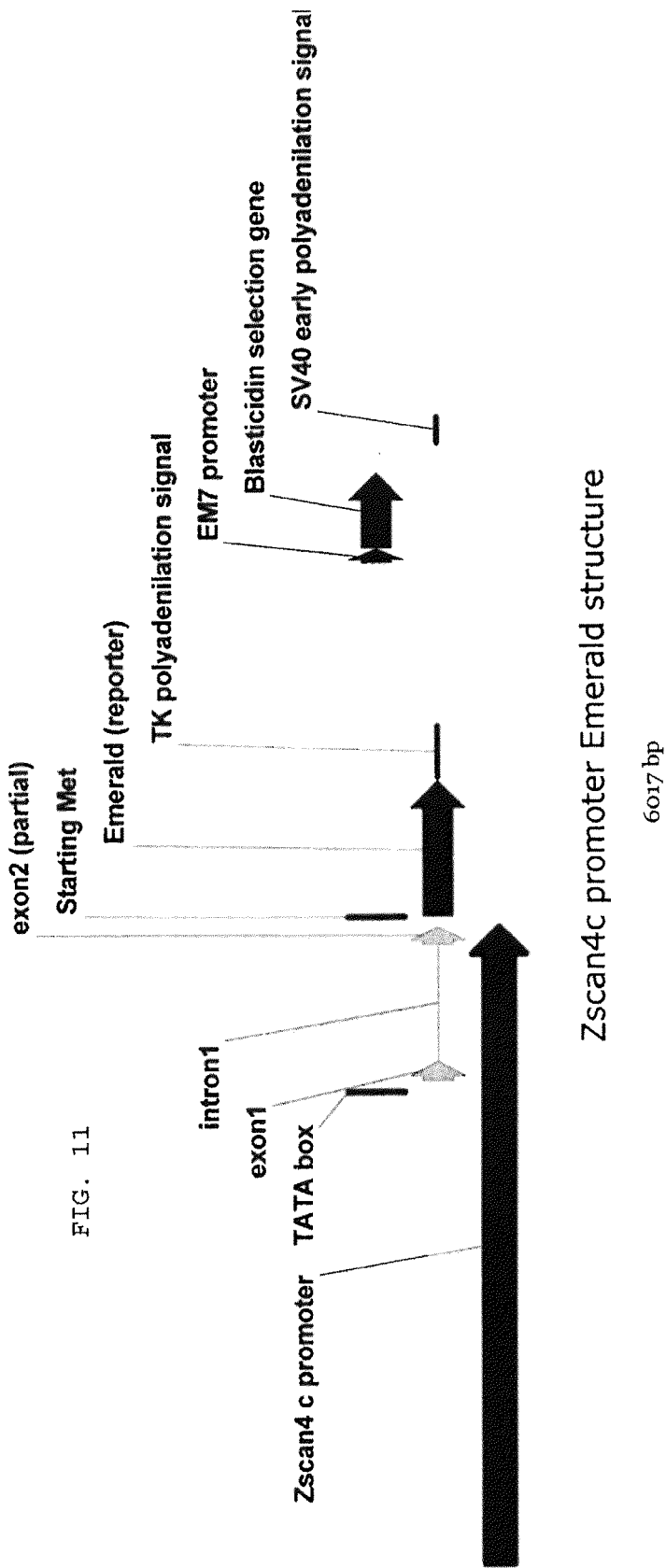
FIG. 11 is an illustration depicting the expression vector comprising the Zscan4c promoter sequence and reporter gene Emerald. The sequence of the expression vector is set forth as SEQ ID NO: 28.

As described in previous Examples herein, Zscan4 expression is only detected in a subpopulation of undifferentiated ES cells. In order to identify this subpopulation of ES cells, and to identify any other cell expressing Zscan4, an expression plasmid was developed which comprises a Zscan4c promoter sequence and the Emerald reporter gene (a variant of green fluorescent protein). The components and orientation of the expression vector are illustrated in FIG. 11. The sequence of the Zscan4c promoter-Emerald expression vector is set forth as SEQ ID NO: 28. The nucleotide ranges of SEQ ID NO: 28 of the components of the expression vector are provided in Table 3.

TABLE 3

Zscan4c Promoter-Emerald Expression Vector

| Component | Nucleotides of SEQ ID NO: 28 |
| --- | --- |
| Zscan4c promoter | 1-3347 |
| TATA box | 2483-2489 |
| Zscan4c exon 1 | 2541-2643 |
| Zscan4c intron 1 | 2644-3250 |
| Zscan4c exon 2 (partial) | 3251-3347 |
| Emerald start codon | 3398-3400 |
| Emerald reporter gene | 3398-4117 |
| TK poly A signal | 4132-4403 |
| EM7 promoter | 5257-5323 |
| Blasticidin selection gene | 5330-5722 |
| SV40 polyA signal | 5880-6010 |

Figures 12A, 12B:
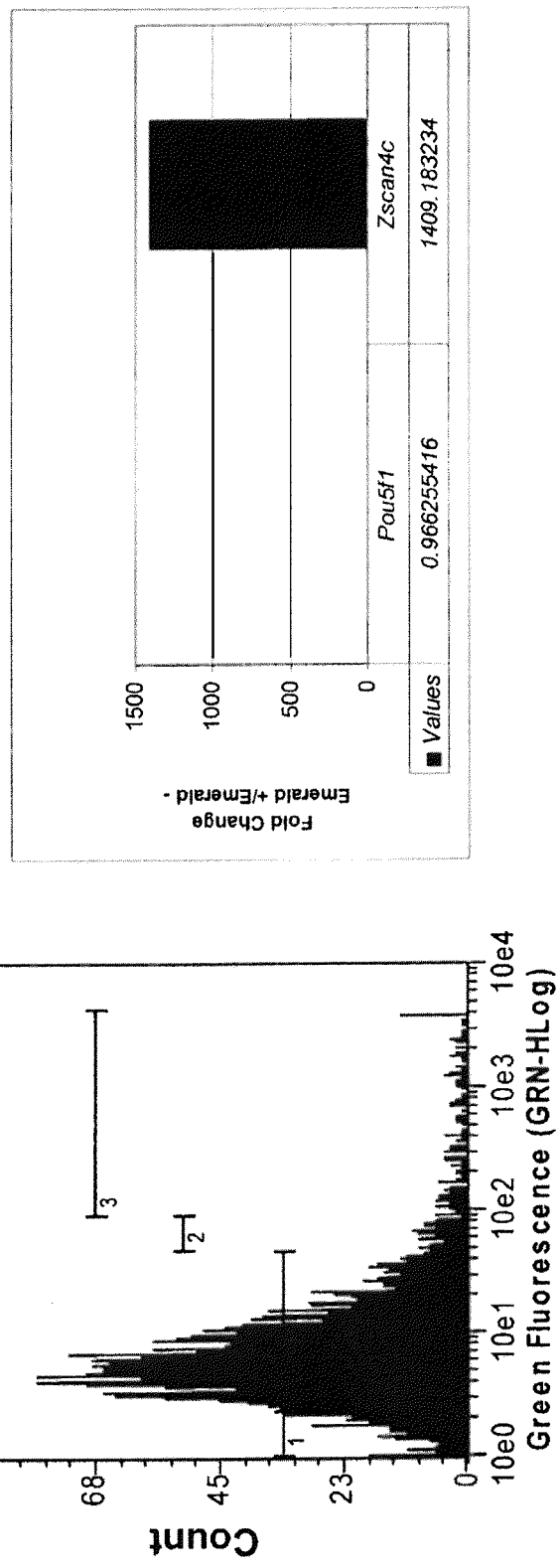
FIG. 12A is a fluorescence activated cell sorting (FACS) graph showing a subpopulation of mouse ES expressing Zscan4. Mouse ES cells were transfected with an expression vector comprising a Zscan4c promoter and a fluorescent reporter gene (Emerald). Expression of the reporter gene in a cell (an Emerald-positive cell) indicates the cell expresses Zscan4.
FIG. 12B is a graph showing expression levels of Zscan4c and Pou5f1 in the subpopulation of ES cells identified as Emerald-positive. The Y-axis represents the fold difference in gene expression between Emerald-positive and Emerald-negative cells.
Figure 13A:
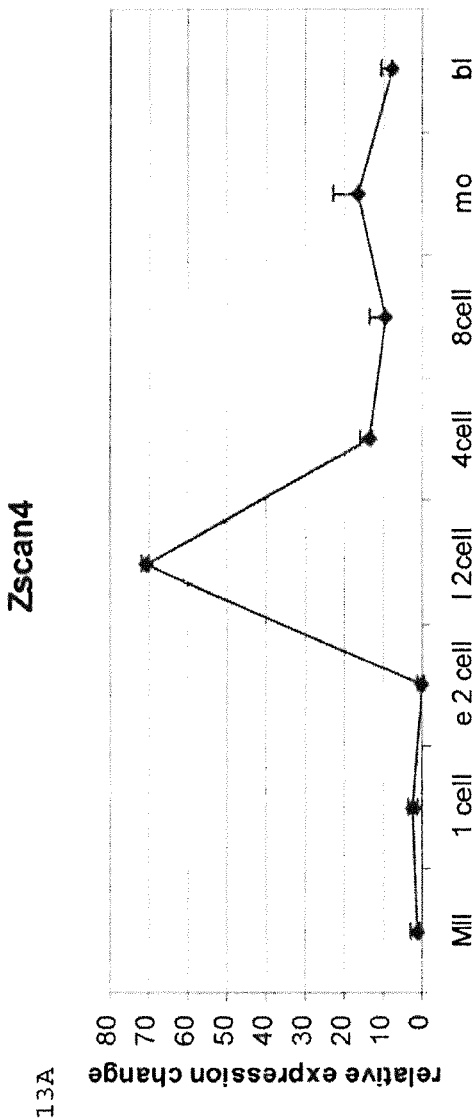
FIGS. 13A-G are graphs showing expression profiles of Zscan4 and six genes co-expressed with Zscan4 in a subpopulation of ES cells. Shown are the expression profiles of Zscan4 (A), AF067063 (B), Tcstv3 (C), Tho4 (D), Arginase II (E), BC061212 (F) and Gm428 (G)) in metaphase II oocytes (MII), 1 cell embryos, early 2 cell (e 2 cell) embryos, late 2 cell (l 2 cell) embryos, 4 cell embryos, 8 cell embryos, morula (mo) and blastocyts (bl).
Figure 13B:
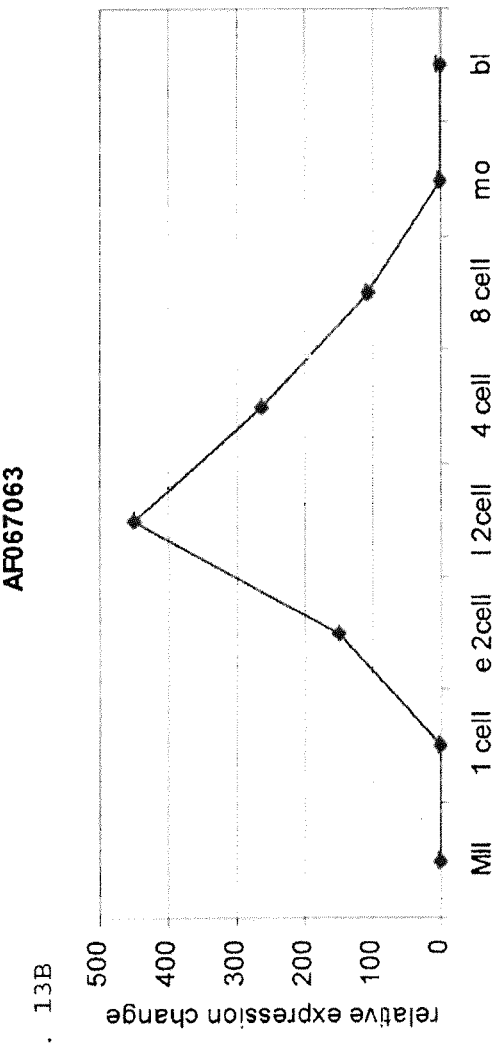
Figure 13C:
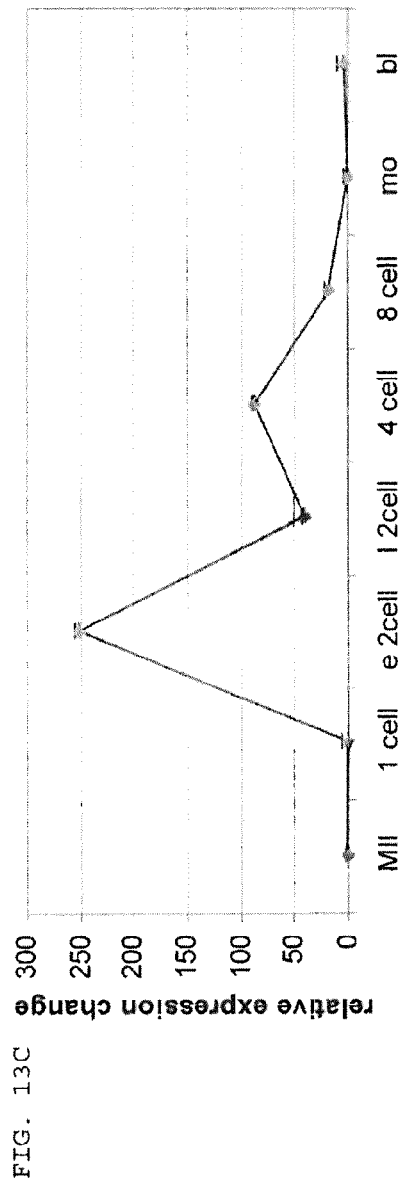
Figure 13D:
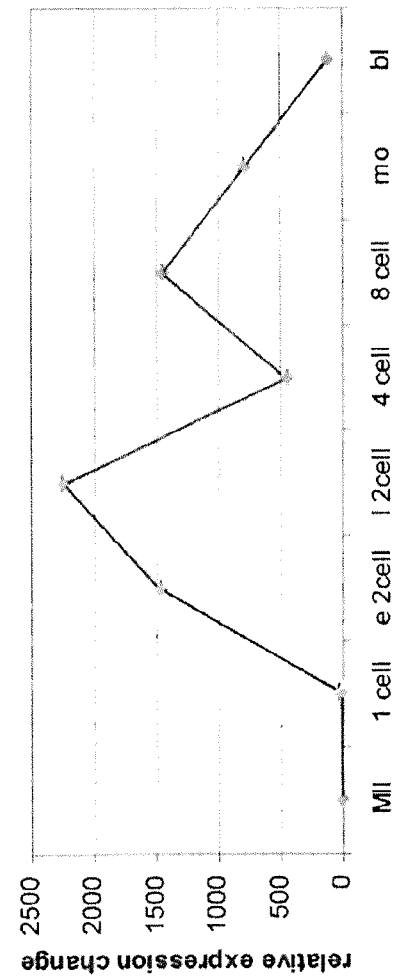
Figure 13E:
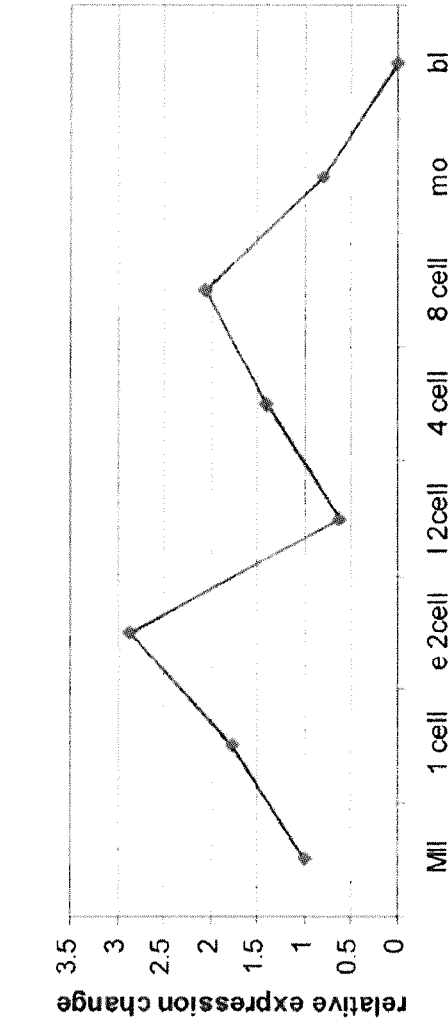
Figure 13F:
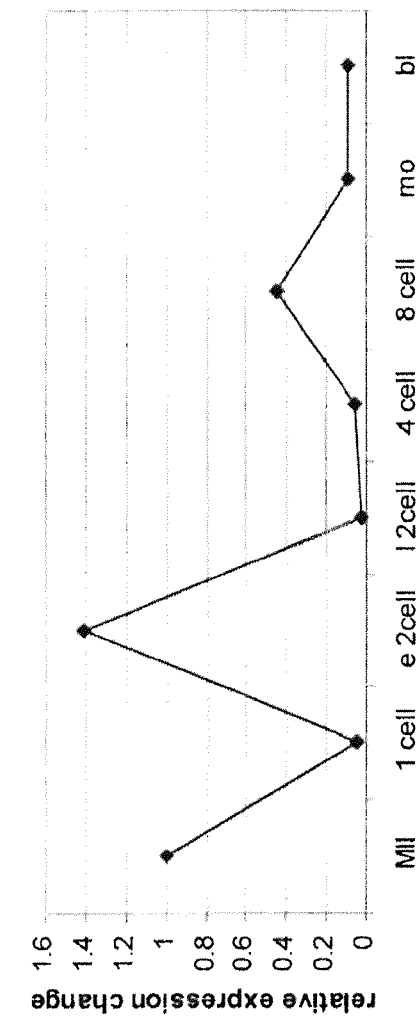
Figure 13G:
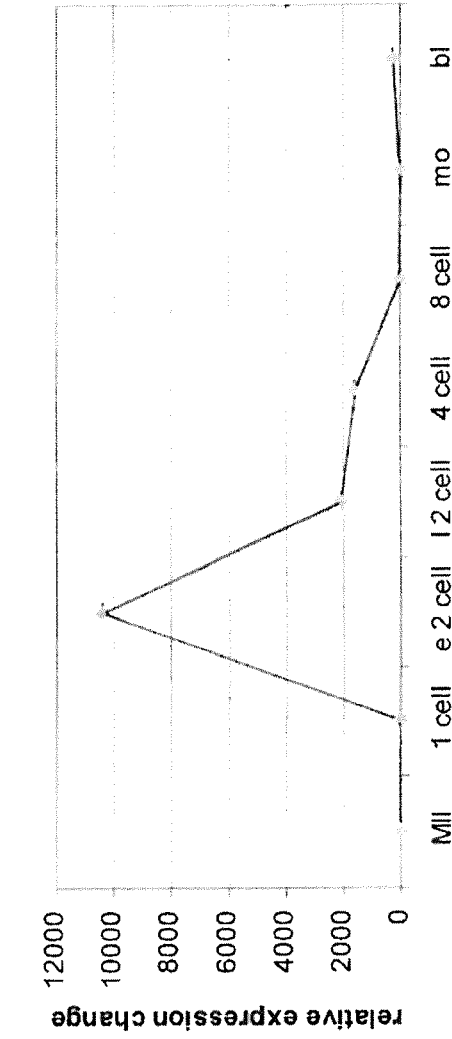

Mouse ES cells were transfected with the Zscan4c promoter expression vector and analyzed by fluorescence activated cell sorting to identify Emerald-positive cells and Emerald-negative cells. If Zscan4 is expressed in a cell, it is Emerald-positive. The results show approximately 3-5% of mouse ES cells express Zscan4 (FIG. 12).

Sorted cells were collected and analyzed by quantitative real time PCR (qPCR) for expression of Zscan4c and Pou5f1 (also known as Oct3, Oct4, Oct3/4), a well known marker for pluripotency. As shown in FIG. 12, Pou5f1 is expressed at the same level in both Emerald-positive and Emerald-negative cells, whereas Zscan4c is more highly expressed in Emerald-positive cells than in Emerald-negative cells. The data indicate that the Zscan4c promoter sequence used in this vector can reproduce the expression of endogenous Zscan4c gene, and thus the Zscan4c promoter-Emerald expression vector can be used to purify Zscan4-expressing cells. The data also indicate that both Zscan4-expressing cells and non-expressing cells retain the pluripotency-marker Pou5f1 expression, thus this subpopulation of ES cells cannot be identified by a standard pluripotency marker.

Example 7

Mouse ES Cell Line Expressing Emerald Under Control of the Zscan4 Promoter

A mouse ES cell line was established in which the Zscan4c promoter expression vector described in Example 6 was stably incorporated into the cells. The ES cell line expresses Emerald under control of the Zscan4c promoter. After transfecting a linearlized plasmid DNA into mouse ES cells, the cells were cultured in the presence of the selectable marker (blasticidin). The blasticidin-resistant ES cell clones were isolated and used for further analysis.

As described herein, Zscan4 is only expressed in a subpopulation of undifferentiated ES cells (approximately 3-5% of ES cells). Accordingly, the ES cell line incorporating the Zscan4 promoter expression vector exhibits expression in only a small percentage, approximately three percent, of cells.

Example 8

Identification of Nine Genes Co-Expressed with Zscan4 in a Sub-Population of ES Cells Using the mouse ES cell line stably transfected with the Zscan4c promoter (as described in Example 7), DNA microarray analysis was performed to compare gene expression patterns of Emerald(+) and Emerald(−) cells. Emerald (+) and Emerald(−) cells were sorted by FACS and total RNAs were isolated from each cell population. These RNAs were labeled and hybridized to the NIA-Agilent 44K DNA microarray (Agilent Technologies).

Nine genes were identified as being co-expressed with Zscan4: AF067063, Tcstv1/Tcstv3, Tho4, Arginase II, BC061212 and Gm428, Eif1a, EG668777 and Pif1. In situ hybridization was performed to confirm expression of these genes in mouse ES cells. The 2-cell embryo-specific expression profiles of six of these genes (AF067063, Tcstv3, Tho4, Arginase II, BC061212 or Gm428) are shown in FIGS. 13A-G.

Example 9

Trim43 is Specifically Expressed in 4-Cell to Morula Stage Embryos

To identify genes that are specifically expressed at the 8-cell and morula stages, publicly available EST frequency data (TIGR Mouse Gene Index; MGI Library Expression Search; NIA Mouse Gene Index (Sharov et al., *PLoS Bio.* 1:E74, 2003)) and microarray data from mouse preimplantation embryos (Hamatani et al., *Dev. Cell* 6 (1):117-31, 2004) were used. After selecting candidate genes, quantitative RT-PCR analysis was carried out to confirm the specific expression pattern of Trim43 (tripartite motif-containing protein 43).

Trim43 expression was detected beginning at the 4-cell embryonic stage and peaked at the morula stage. A low level of Trim43 expression was detected in blastocysts. The function of the Trim43 protein is unknown. The nucleotide and amino acid sequences of Trim43 are provided herein as SEQ ID NO: 32 and SEQ ID NO: 33, respectively. The nucleic acid sequence of the Trim43 promoter is provided herein as SEQ ID NO: 31.

Example 10

Transgenic "Rainbow" Mouse

As described herein, an expression vector comprising a Zscan4c promoter operably linked to a first heterologous polypeptide (Emerald) and an expression vector comprising a Trim43 promoter operably linked to a second heterologous polypeptide (Strawberry), have been generated. A transgenic mouse (a "rainbow" mouse) can be generated which incorporates both of these expression constructs.

A 7155 base pair DNA fragment containing the Insulator-Zscan4 promoter-emerald and TK polyA and a 8672 base pair DNA fragment containing the Insulator-Trim43 promoter-Strawberry are co-injected into the pronucleus of fertilized mouse eggs (B6C3X B6).

Embryos obtained from the rainbow mouse will exhibit green color (as a result of expression of Emerald) at the late 2-cell stage, and red color (due to expression of Strawberry) from the 4-cell stage to the morula stage (with peak expression at the morula stage). The expression of Emerald and Strawberry at the appropriate stage of embryonic development indicates proper development of the embryo. Thus, these embryos will be useful for a number of research and clinical purposes. For example, embryos obtained from the rainbow mouse can be used to develop optimized culture conditions for embryos, which can be applied to human embryos used in the IVF clinic. In addition, these embryos can be used to test chemical compounds or drugs for toxicity to the embryo. The embryos can also be used as indicators of successful nuclear reprogramming for nuclear transplantation procedures.

This disclosure provides methods of inhibiting differentiation of stem cells and promoting blastocyst outgrowth of ES cells. The disclosure further provides a Zscan4 promoter sequence and methods of use, including identification of a subpopulation of stem cells expressing Zscan4. It will be apparent that the precise details of the methods described may be varied or modified without departing from the spirit of the described invention. We claim all such modifications and variations that fall within the scope and spirit of the claims below.

The invention claimed is:

1. An in vitro method of identifying a subpopulation of cultured human or mouse embryonic stem (ES) cells expressing Zscan4, comprising:
    (a) transfecting a population of mouse or human ES cells with an expression vector comprising a Zscan4c promoter operably linked to a nucleotide sequence encoding a reporter, wherein the Zscan4c promoter is selected from group consisting of the nucleic acid sequence as set forth in nucleotides (i) 1-2540 of SEQ ID NO: 28, (ii) 1-2643 of SEQ ID NO: 28, (iii) 1-3250 of SEQ ID NO: 28 and (iv) 1-3347 of SEQ ID NO: 28; and
    (b) identifying a subpopulation of cells that expresses the reporter gene indicating Zscan-4 is expressed in the subpopulation of stem cells.

2. The method of claim 1, wherein the expression vector consists of the nucleotide sequence as set forth in SEQ ID NO: 28.

3. The method of claim 1, wherein the reporter gene encodes a marker, enzyme, or fluorescent protein.

4. The method of claim 1, wherein the expression vector is a viral vector.

5. The method of claim 1, wherein the expression vector is a plasmid vector.

6. The method of claim 1, wherein the population of embryonic stem cells are mouse embryonic stem cells.

7. The method of claim 1, wherein the population of embryonic stem cells are human embryonic stem cells.

* * * * *

SEQUENCE LISTING

```
<160> NUMBER OF SEQ ID NOS: 60

<210> SEQ ID NO 1
<211> LENGTH: 21
<212> TYPE: DNA
<213> ORGANISM: Artificial
<220> FEATURE:
<223> OTHER INFORMATION: Primer

<400> SEQUENCE: 1
cctccctggg cttcttggca t                                              21

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
agctgccaac cagaaagaca ctgt                                           24

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
gcattcctac ataccaatta                                                20

<210> SEQ ID NO 4
```

```
<211> LENGTH: 20
<212> TYPE: DNA
<213> ORGANISM: Artificial
<220> FEATURE:
<223> OTHER INFORMATION: Primer

<400> SEQUENCE: 4
gatttaattt agctgggctg                                                   20

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
cagatgccag tagacaccac                                                   20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
gtagatgttc cttgacttgc                                                   20

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
ggaagtgtta tagcaattgt tc                                                22

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
gtgttatagc aattgttctt g                                                 21

<210> SEQ ID NO 9
<211> LENGTH: 19
<212> TYPE: DNA
<213> ORGANISM: Artificial
<220> FEATURE:
<223> OTHER INFORMATION: siRNA

<400> SEQUENCE: 9
gagtgaattg ctttgtgtc                                                    19

<210> SEQ ID NO 10
<211> LENGTH: 21
<212> TYPE: DNA
<213> ORGANISM: Artificial
<220> FEATURE:
<223> OTHER INFORMATION: siRNA

<400> SEQUENCE: 10
```
agagacatag aatcgcacgc a                                          21

<210> SEQ ID NO 11
<211> LENGTH: 2292
<212> TYPE: DNA
<213> ORGANISM: Mus musculus

<400> SEQUENCE: 11

| | | | | | |
|---|---|---|---|---|---|
| gacacacagt | gcctccctgg | gcttcttggc | atcacccttg | aagttcaccg | gagaaagcag | 60 |
| tgaggtggag | gaataggtaa | actttccttc | ctagtggtct | tgaatgtctt | ttacagtaca | 120 |
| tccatcaact | gttagcattt | tcgtaaagtc | acaaaacaga | tattaaacta | ctatagttga | 180 |
| atctttcaca | ccattgtcac | cacaatggct | tcacagcagg | caccagcaaa | agaccttcag | 240 |
| accaacaatt | tagagtttac | tccaactgat | agttctggtg | tgcagtgggc | agaagacatc | 300 |
| tctaactcac | caagtgctca | gctaaacttt | tccccaagta | acaatggctg | ctgggcaact | 360 |
| caggagctgc | aaagtctctg | gaagatgttc | aactcctggt | tgcagccaga | aaagcagact | 420 |
| aaggagcaga | tgatttctca | actggtcttg | gagcagtttc | tcctcactgg | gcactgcaag | 480 |
| gacaagtatg | cttttgacaga | gaagtggaaa | gccagtggta | gcgatatgag | gagattcatg | 540 |
| gagagtctga | ctgatgagtg | cttgaagcct | cctgtcatgg | tccatgtttc | aatgcaagga | 600 |
| caagaagccc | tcttttctga | aaacatgcca | ttaaaagaag | tcatcaagct | tttgaaacaa | 660 |
| cagcaatctg | caacaaggcc | aacaccagat | aatgagcaga | tgccagtaga | caccacacaa | 720 |
| gatagattat | tggccacagg | acaagaaaac | agtgaaaatg | aatgcaacaa | ctcttgtaat | 780 |
| gctactgaag | caaatgttgg | tgaaagctgt | agtggaaatg | aaatggactc | ccttcttatt | 840 |
| atccagaaag | aacagcaccc | tgagcatgaa | gaggggaatg | ttgtttgtca | attccctcat | 900 |
| ggtgccagaa | gagcaagtca | aggcaccccc | agtcatcatg | tagacttccc | gagtgctccg | 960 |
| actactgccg | atgtccccat | ggaggaacaa | ccaaaggatt | tatccagaga | aaacatctct | 1020 |
| gaggacaaga | acaattgcta | taacacttcc | agaaatgcag | ctactcaagt | atatagtggt | 1080 |
| gataatattc | ccaggaacaa | gtcagactcc | cttttcatta | acaagagaat | atatcatcct | 1140 |
| gagcctgagg | tgggagatat | tccttatgga | gttcctcagg | attctacaag | agcaagtcaa | 1200 |
| ggaacatcta | catgcctgca | agagtcactt | ggggaatgtt | tttctgaaaa | cgacccaagg | 1260 |
| gaggtaccag | ggttgcagtc | taggcaagag | cagcctatct | ctgatcctgt | ccttcttggt | 1320 |
| aagaatcatg | aggcaaactt | accatgtgaa | agtcatcaaa | agagattctg | tagagatgcc | 1380 |
| aaactataca | agtgtgaaga | atgttctagg | atgttcaaac | atgccaggag | cctttcatcc | 1440 |
| caccagagaa | ctcacctgaa | taagaagagt | gaattgcttt | gtgtcacctg | tcagaaaatg | 1500 |
| ttcaaacgag | tctctgaccg | ccgcacccat | gagatcatac | acatgccaga | aaagcctttc | 1560 |
| aagtgcagca | catgtgaaaa | gtccttcagc | cacaagacca | acctgaagtc | tcatgagatg | 1620 |
| attcacacag | gagaaatgcc | ttatgtctgt | tccctatgta | gccgtcgctt | tcgccaatca | 1680 |
| tccacttacc | atcgtcacct | gaggaattac | cacagatctg | actgaactat | ctaacatcct | 1740 |
| cagcagagac | tggtagggct | tcagcctcag | tatgtcatct | tcaaagagag | aagaatgttg | 1800 |
| caagtaaatt | gtactgtccc | aataatgata | taacatgctt | gtggattgcc | actttatgt | 1860 |
| tttgtttttgt | tttttatttt | gtgtgtgtgt | gtatgtaatt | ttttgtctgt | atttccatat | 1920 |
| ttccacagca | taagttatta | gaatactttg | ctgttaattc | ttgagttgct | tcttgctttt | 1980 |
| agacagtgtc | tttctggttg | gcagctttat | aaacctgtct | ttctggcact | agagtttcca | 2040 |
| aacatttct | ggtctccact | tttattctct | acagtgttct | tgacagaagc | ctggcattcc | 2100 |

-continued

| | |
|---|---|
| ctctgacatt ttctacatgt tggggttttc atcccaagtc ttagggttgc aagttaaatg | 2160 |
| cattgcctct tcagacatct catgccatgt ctactgctta cagttcaaga atatttctct | 2220 |
| acattactag aacgacgttc aaagtggaat aataaataaa taaataatca acaattaaaa | 2280 |
| aaaaaaaaaa aa | 2292 |

<210> SEQ ID NO 12
<211> LENGTH: 2288
<212> TYPE: DNA
<213> ORGANISM: Mus musculus

<400> SEQUENCE: 12

| | |
|---|---|
| cacagtgcct ccctgggctt cttggcatca cccttaaagt tcactggaga aagaggtgag | 60 |
| gtggaggagt aggtaaactt ccctacctag tggtcttgaa tgtcttttat agtcatccaa | 120 |
| tcaactgtta gcattttcct aaagtcacaa aacagatact aaactgctat agttgaatct | 180 |
| ttcacaccat tgtcaccaca atggcttcac agcaggcacc agcaaaagac cttcagacca | 240 |
| acaatttaga gtttactcca actgatagtt ctggtgtgca gtgggcagaa gacatctcta | 300 |
| actcaccaag tgctcagcta aacttttccc caagtaacaa tggctgctgg gcaattcagg | 360 |
| agctgcaaag tctctggaag atgttcaact cctggttgca gccagaaaag cagactaagg | 420 |
| agcagatgat ttctcaactg gtcttggagc agtttctcct cactgggcac tgcaaggaca | 480 |
| agtatacttt gacagagaag tggaaagcca gtggtagcga tatgaggaga ttcatggaga | 540 |
| gtctgactga tgagtgcttg aagcctccag tcatggtcca tgtttcaatg caaggacaag | 600 |
| aagccctctt ttctgaaaac atgccattaa agaagtcat caagcttttg aaacaacagc | 660 |
| aatctgcaac aaggccaaca ccagataatg agcagatgcc agtagacacc acacaagata | 720 |
| gattattggc cacaggacaa gaaaacagtg aaaatgaatg caacacctct tgtaatgcta | 780 |
| ctgaaggaaa tgttggtgaa agatgtggtg gaaatgaaat ggactcccct cttattatcc | 840 |
| agaaagaaca gcaccctgag catgaagagg ggaatgttgt ttgtcgattc cctcatggtg | 900 |
| ccagaagagc aagtcaaggc aactctagtc atcatgtaga cttccggagt gctctgactc | 960 |
| ctgcggatgt ccccatggag gaacaaccaa aggatttatc cagagaaaac atctctgagg | 1020 |
| acaagaacaa ttgctataac acttccagga atgcagctac tcaagtatat agcagtgata | 1080 |
| atattcccag gaaaaaaaca gactcccttt ccattaacaa gagaatatat catcctgagc | 1140 |
| ctgaggtggg agatattcct tatggagttc ctcatgattc tacaagagca agtcaaggaa | 1200 |
| catctacatg cctgcaagag tcacttgggg aatgtttttc tgaaaagac cctagggagg | 1260 |
| taccagggtt ggagtctagg caagaggagc ctatctctga tcctgtcctt cttggtaaga | 1320 |
| atcatgaggc aaacttacca tgtgaaagtc atcataagag attccgtaga gatgccaaac | 1380 |
| tatacaagtg tgaagaatgt tctaggatgt tcaaacatgc caggagcctt tcatcccacc | 1440 |
| agagaactca cctgaataag aagagtgaat tgctttgttt cacctgtcag aaaatgttca | 1500 |
| aacgagtctc tgaccgccga acccatgaga tcatacacat gccagaaaag cctttcaagt | 1560 |
| gcagcacatg tgaaaagtcc ttcagccaca agaccaacct gaagtctcat gagatgattc | 1620 |
| acacaggaga aatgccttat gtctgttccc tatgtagccg tcgctttcgc caatcatcca | 1680 |
| cttaccatcg tcacctgagg aattaccaca gatctgactg aactatctaa catccttagc | 1740 |
| agagactggt agagcttcag cctcagtatg tcatcttcaa agagagaaga atgttgctac | 1800 |
| taaattgtac tttcccaatg atgatataac atgcttgtag agtgccactt ttatgttttg | 1860 |
| ttttgttttg ttttgttttg ttttgttttg tgtgtgtgtg tgtgtgtgtg taattttttg | 1920 |

| | | | | |
|---|---|---|---|---|
| tctgtatttc | catagttcca | cagcataagt | tattagaata | ctttgctgtt aattcttgag | 1980 |
| ttgtttcttg | cttttaaaca | gtggccttct | ggttggcagc | tttatacacc tgtctttatg | 2040 |
| gcattagagt | ttccaaacat | tttctgatct | ccacttttat | tctctacagt ggtcctgaca | 2100 |
| gaggcctgcc | attccctctg | acatttttct | acctgttggg | gttttaatcc acagtcttaa | 2160 |
| ggttgcaagt | taaatgcatt | gccttttcag | acatctccca | tgtcatgtct actgcttaca | 2220 |
| gtatatttct | ctacattact | agaatgacat | tcaaagtgga | gtaataaata aataataat | 2280 |
| caacaatt | | | | | 2288 |

<210> SEQ ID NO 13
<211> LENGTH: 2273
<212> TYPE: DNA
<213> ORGANISM: Mus musculus

<400> SEQUENCE: 13

| | | | | | |
|---|---|---|---|---|---|
| cacagtgcct | ccctgggctt | cttggcatca | cccttgaagt | tcactggaga aagaggtgag | 60 |
| gtggaggaat | aggtaaactt | tccttcctag | tggtcttgaa | tgtctttac agtacatcca | 120 |
| tcaactgtta | gcattttcgt | aaagtcacaa | aacagatatt | aaactactat agttgaatct | 180 |
| ttcacaccat | tgtcaccaca | atggcttcac | agcaggcacc | agcaaaagac cttcagacca | 240 |
| acaatttaga | gttactcca | actgatagtt | ctggtgtgca | gtgggcagaa gacatctcta | 300 |
| actcaccaag | tgctcagcta | aacttttccc | caagtaacaa | tggctgctgg gcaactcagg | 360 |
| agctgcaaag | tctctggaag | atgttcaact | cctggttgca | gccagaaaag cagactaagg | 420 |
| agcagatgat | ttctcaactg | gtcttggagc | agtttctcct | cactgggcac tgcaaggaca | 480 |
| agtatgcttt | gactgagaag | tggaaagcca | gtggtagcga | tatgaggaga ttcatggaga | 540 |
| gtctgactga | tgagtgcttg | aagcctcctg | tcatggtcca | tgtttcaatg caaggacaag | 600 |
| aagccctctt | ttctgaaaac | atgccattaa | agaagtcat | caagctttg aaacaacagc | 660 |
| aatatgcaac | aaggccaaca | ccagataatg | agcagatgcc | agtagacacc acacaagata | 720 |
| gattattggc | cacaggacaa | gaaaacagtg | aaaatgaatg | caacaactct tgtaatgcta | 780 |
| ctgaaggaaa | tgttggtgaa | agctgtagtg | gaaatgaaat | ggactccctt cttattatcc | 840 |
| agaaagaaca | gcaccctgag | catgaagagg | ggaatgttgt | ttgtcaattc cctcatggtg | 900 |
| ccagaagagc | aagtcaaggc | acccccagtc | atcatgtaga | cttcccgagt gttccgacta | 960 |
| ctgccgatgt | ccccatggag | gaacaaccaa | aggatttatc | cagagaaaac atctctgagg | 1020 |
| acaagaacaa | ttgctataac | acttccagaa | atgcagctac | tcaagtatat agtggtgata | 1080 |
| atattcccag | gaacaagtca | gactcccttt | tcattaacaa | gagaatatat catcctgagc | 1140 |
| ctgaggtggg | agatattcct | tatggagttc | ctcaggattc | tacaagagca agtcaaggaa | 1200 |
| catctacatg | cctgcaagag | tcacttgggg | aatgttttc | tgaaaagac cctagggagg | 1260 |
| taccagggtt | gcagtctagg | caagagcagc | ttatctctga | tcctgtcctt cttggtaaga | 1320 |
| atcatgaggc | aaacttacca | tgtgaaagtc | atcaaaagag | attctgtaga gatgccaaac | 1380 |
| tatacaagtg | tgaagaatgt | tctaggatgt | tcaaacatgc | caggagcctt tcatcccacc | 1440 |
| agagaactca | cctgaataag | aagagtgaat | tgctttgtgt | cacctgtcag aaaatgttca | 1500 |
| aacgagtctc | tgaccgccga | acccatgaga | tcatacacat | gccagaaaag cctttcaagt | 1560 |
| gcagcacatg | tgaaaagtcc | ttcagccaca | agaccaacct | gaagtctcat gagatgattc | 1620 |
| acacaggaga | aatgccttat | gtctgttccc | tatgtagccg | tcgctttcgc caatcatcca | 1680 |
| cttaccatcg | tcacctgagg | aattaccaca | gatctgactg | aactatctaa catcctcagc | 1740 |

-continued

| | |
|---|---|
| agagactggt agggcttcag cctcagtatg tcatcttcaa agagagaaga atgttgcaag | 1800 |
| taaattgtac tgtcccaata atgatataac atgcttgtgg attgccactt ttatgttttg | 1860 |
| ttttgttttt tattttgtgt gtgtgtgtat gtaattttt gtctgtattt ccatagttcc | 1920 |
| acagcataag ttattagaat actttgctgt taattcttga gttgcttctt gcttttagac | 1980 |
| agtgtctttc tggttgacag ctttataaac ctgtctttct ggcactagag tttccaaaca | 2040 |
| ttttctgatc tccacttta ttctctacag tgttcttgac agaagcctgg cattccctct | 2100 |
| gacatttttc tacatgttgg ggttttcatc ccaagtctta gggttgcaag ttaaatgcat | 2160 |
| tgcctcttca gacatctcat gccctgtcta ctgcttacag ttcaagaata tttctctaca | 2220 |
| ttactagaac gacattcaaa gtggaataat aaataaataa ataatcaaca att | 2273 |

<210> SEQ ID NO 14
<211> LENGTH: 2273
<212> TYPE: DNA
<213> ORGANISM: Mus musculus

<400> SEQUENCE: 14

| | |
|---|---|
| cacagtgcct ccctgggctt cttggcatca ccctagaagt tcactggaga aagaggtgag | 60 |
| gtggaggaat aggtaaactt tccttcctag tggtcttgaa tgtcttttac agtacactat | 120 |
| cagctgttag cattttccta aagtcacaaa acagatacta aactgctata gttgaatctt | 180 |
| tcacaccatt gtcaccacaa tggcttcaca gcaggcacca gcaaaagacc ttcagaccaa | 240 |
| caatttagag tttactccaa ctgatagttc tggtgtgcag tgggcagaag acatctctaa | 300 |
| ctcaccaagt gctcagctaa acttttcccc aagtaacaat ggctgctggg caactcagga | 360 |
| gctgcaaagt ctctggaaga tgttcaactc ctggttgcag ccagaaaagc agactaagga | 420 |
| gcagatgatt tctcaactgg tcttggagca gtttctcctc actgggcact gcaaggacaa | 480 |
| gtatgctttg acagagaagt ggaaagccag tggtagcgat atgaggagat tcatggagag | 540 |
| tctgactgat gagtgcttga agcctcctgt catggtccat gtctcaatgc aaggacaaga | 600 |
| agcactcttt tctgaaaaca tgccattaaa agaagtcatc aagcttttga acaacagca | 660 |
| atatgcaaca aggccaacac cagataatga gcagatgcca gtagcacca cacaagatag | 720 |
| attattggcc acaggacaag aaaacagtga aaatgaatgc aacaactctt gtaatgctac | 780 |
| tgaagcaaat gttggtgaaa gctgtagtgg aaatgaaatg gactcccttc ttatcatcca | 840 |
| gaaagaacag caccctgagc atgaagaggg gaatgttgtt cgtcaattcc ctcatggtgc | 900 |
| cagaagcagca agtcaaggca cccccagtca tcatgtagca atccagagtc ctccgactac | 960 |
| tgccgatgtc accatggagg aacaaccaaa ggatttatcc agagaaaaca tctctgagga | 1020 |
| caagaacaat tgctataaca cttccaggaa tgcagctact caagtatata gtggtgataa | 1080 |
| tattcccagg aacaagtcag actcccttt cattaacaag agaatatatc atcctgagcc | 1140 |
| tgaggtggga gatattcctt atggatttcc tcaggattct acaagagcaa gtcaaggaac | 1200 |
| atctacatgc ctgcaagagt cacttgggga atgtttttct gaaaaagacc ctagggaggt | 1260 |
| accagggttg cagtctaggc aagagcagct tatctctgat cctgtccttc ttggtaagaa | 1320 |
| tcatgaggca aacttaccat gtaaaagtca tcaaaagaga ttctgtagag atgccaaact | 1380 |
| atacaagtgt gaagaatgtt ctaggatgtt caaacatgcc aggagccttt catcccacca | 1440 |
| gaaaactcac ctcaataaga agagtgaatt gctttgtgtc acctgtcaga aaatgttcaa | 1500 |
| acgagtctct gaccgccgaa cccatgagat catacacatg ccagaaaagc ctttcaagtg | 1560 |
| cagcacatgt gaaaagtcct tcagccacaa gaccaacctg aagtctcatg agatgattca | 1620 |

-continued

| | |
|---|---|
| cacaggagaa atgccttatg tctgttccct atgtagccgt cgctttcgcc aatcatccac | 1680 |
| ttaccatcgt cacctgagga attaccacag atctgactga actatctaac atcctcagca | 1740 |
| gagactggta gggcttcagc ctcagtatgt catcttcaaa gagagaagaa tgttgcaagt | 1800 |
| aaattgtact gtcccaataa tgatataaca tgcttgtgga ttgccacttt tatgttttgt | 1860 |
| tttgttttgt ttttattttt gtgtgtgtgt gtaatttttt gtctgtattt ccatagttcc | 1920 |
| acagcataag ttattagaat actttgctgt taattcttga gttgcttctt gcttttagac | 1980 |
| agtgtctttc tggttggcag ctttataaac ctgtctttct ggcactagag tttccaaaca | 2040 |
| ttttctgatc tccactttta ttctctacag tgttcttgac agaagcctgg cattccctct | 2100 |
| gacatttttc tacatgttgg ggttttcatc ccaagtctta gggttgcaag ttaaatgcat | 2160 |
| tgcctcttca gacatctcat atcatgtcta ctgcttacag ttcaagaatc tttctctaaa | 2220 |
| ttactagaac gatgttcaaa gtggaataat aaataaataa ataatcaaca att | 2273 |

<210> SEQ ID NO 15
<211> LENGTH: 2275
<212> TYPE: DNA
<213> ORGANISM: Mus musculus

<400> SEQUENCE: 15

| | |
|---|---|
| cacagtgcct ccctgggctt cttggcatca cccttgaagt tcactggaga aagagttgag | 60 |
| gtggaggaat aggtaaactt cccttcctag tggtcttgaa tgtcttttac agtacatcca | 120 |
| tcaactgtta gcattttcgt aaagtcacaa aacagatatt aaactactat agttgaatct | 180 |
| ttcacaccat tgtcaccaca atggcttcac agcaggcacc agcaaaagac cttcagacca | 240 |
| acaatttaga gtttactcca actgatagtt ctggtgtgca gtgggcagaa gacatctcta | 300 |
| actcaccaag tgctcagcta aacttttccc caagtaacaa tggctgctgg gcaactcagg | 360 |
| agctgcaaag tctctggaag atgttcaact cctggttgca gccagaaaag cagactaagg | 420 |
| agcagatgat ttctcaactg gtcttggagc agtttctcct cactgggcac tgcaaggaca | 480 |
| agtatgcttt gacagagaag tggaaagcca gtggtagcga tatgaggaga ttcatggaga | 540 |
| gtctgactga tgagtgcttg aagcctcctg tcatggtcca tgtctcaatg caaggacaag | 600 |
| aagccctctt ttctgaaaac atgccattaa agaagtcat caagctttg aaacaacagc | 660 |
| aatctgcaac aaggccaaca ccagataatg cacagatgcc agtagacacc acacaagata | 720 |
| gattattggc cacaggacaa gaaaacagtg aaaatgaatg caacacctct tgtaatgcta | 780 |
| ctgaaggaaa tgttggtgag agctgtagtg gaaatgaaat ggactcctct cttattatcc | 840 |
| agaaagaaca gtaccctgag catgaagagg ggaatgttgt ttgtcaattc cctcttgatg | 900 |
| ccagaagagc aagtcaaggc acctccagtc atcatgtaga cttcctgagt gctctgacta | 960 |
| ctgccgatgt ccccatggag gaacaaccaa aggatttatc cagagaaaac atctctgagg | 1020 |
| acaagaacaa ttgctataac acttccagga atgcagctac taaagtatat agtggtgata | 1080 |
| atattcccag gaaaaagaca gactcccttt ccattaacaa gaggatatat catcctgagc | 1140 |
| ctgaggtggg agatattcct tatggagttc ctcaggattc tacaagagca agtcaaggaa | 1200 |
| catctacatg cctgcaagag tcacttgggg gatgttttc cgaaaagac cctagggagg | 1260 |
| taccaggggtt gcagtctagg taagagcagc ctatctctga tcctgtcctt cttggtaaga | 1320 |
| atcatgaggc aaacttacca tgtgaaagtc atcaaaagag attctgtaga gatgccaaac | 1380 |
| tatacaagtg tgaagaatgt tctaggatgt tcaaacatgc caggagcctt tcatcccacc | 1440 |
| agagaactca cctgaataag aagagtgaat tgctttgtgt cacctgtcag aaaattttca | 1500 |

-continued

```
aacgagtctc tgaccgccga acccatgaga tcatacacat gccagaaaag cctttcaagt    1560
gcagcacatg tgaaaagtcc ttcagccaca agaccaacct gaagtctcat gagatgattc    1620
acacaggaga atgccttat gtctgttccc tatgtagccg tcgctttcgc caatcatcca     1680
cttaccatcg tcacctgagg aattatcaca gatctgactg aagtatctaa catcctcagc    1740
agagactggt agggcttcag cctcagtatg tcatcttcaa agagagaaga atgttgcaag    1800
taaattgtac tgtcccaata atgatataac atgcttgtgg attgccactt ttatgttttg    1860
ttttgttttg tttttatt tgtgtgtgtg tatgtaattt tttgtctgta tttccatagt      1920
tccacagcat aagttattag aatactttgc tgttaattct tgagttgctt cttgcttta    1980 gacagtgtct ttctggttgg cagctttata cacctgtctt tctggcacta gagtttccaa    2040
acattttctg atctccactt ttattttcta cagtggtcct gacagaggcc tgccattccc    2100
tctgacattt ttctacatgt tggggtttca tcccaagtct tagggttgca agttaaatgc    2160
attgcctctt cagacatctc atgtcatgtc tactgcttac agttcaagaa tatttctcta    2220
cattactaga acgacgttca agtggaata ataaataaat aaataatcaa caatt          2275
```

<210> SEQ ID NO 16
<211> LENGTH: 360
<212> TYPE: PRT
<213> ORGANISM: Mus musculus

<400> SEQUENCE: 16

```
Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
                20                  25                  30

Ser Asn Ser Pro Ser Ala Gln Leu Asn Phe Ser Pro Asn Asn Gly
            35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Ser Ala Thr Arg Pro Thr
145                 150                 155                 160

Pro Asp Asn Ala Gln Met Pro Val Asp Thr Thr Gln Asp Arg Leu Leu
                165                 170                 175

Ala Thr Gly Gln Glu Asn Ser Glu Asn Glu Cys Asn Thr Ser Cys Asn
            180                 185                 190

Ala Thr Glu Gly Asn Val Gly Glu Ser Cys Ser Gly Asn Glu Met Asp
        195                 200                 205

Ser Ser Leu Ile Ile Gln Lys Glu Gln Tyr Pro Glu His Glu Glu Gly
    210                 215                 220

Asn Val Val Cys Gln Phe Pro Leu Asp Ala Arg Arg Ala Ser Gln Gly
225                 230                 235                 240

Thr Ser Ser His His Val Asp Phe Leu Ser Ala Leu Thr Thr Ala Asp
```

```
                    245                 250                 255
Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Lys
            275                 280                 285

Val Tyr Ser Gly Asp Asn Ile Pro Arg Lys Lys Thr Asp Ser Leu Ser
            290                 295                 300

Ile Asn Lys Arg Ile Tyr His Pro Glu Pro Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Gly Cys Phe Ser Glu Lys Asp Pro Arg
            340                 345                 350

Glu Val Pro Gly Leu Gln Ser Arg
            355                 360

<210> SEQ ID NO 17
<211> LENGTH: 1774
<212> TYPE: DNA
<213> ORGANISM: Mus musculus

<400> SEQUENCE: 17
cacagtgcct ccctgggctt cttggcatca cccttgaagt tcactggaga aagaggtgat    60
gtggagaagt aggtaaactt ccctttcttg tggtcttgaa tgtcttttac agtacatccg   120
tcaactgtta gcattttcct aaagtcacaa aacagatact aaactgctat agttgaatct   180
ttcagaccat tgtcaccaca atggcttcac agcaggcacc agcaaaagac cttcagacca   240
acaatttaga gtttactcca actgatagtt ctggtgtgca gtgggcagaa gacatctcta   300
actcaccaag tgctcagcta aacttttccc caagtaacaa tggctgctgg gcaactcagg   360
agctgcaaag tctctggaag atgttcaact cctggttgca gccagaaaag cagactaagg   420
agcagatgat ttctcaattg gtcttggagc agtttctcct cactgggcac tgcaaggaca   480
agtatgcttt gacagagaag tggaaagcca gtggtagcga tatgaggaga ttcatggaga   540
gtctgactga tgagtgcttg aagcctcctg tcatggtcca tgtttcaatg caaggacaag   600
aagccctctt ttctgaaaac atgccattaa agaagtcat caagcttttg aaacaacagc   660
aatctgcaac aaggccaata ccagataatg cacagatgcc agtagacacc acacaagata   720
gattattggc cacaggcaag aaaacagtga aaatgaatgc aacacctctt gcaatgctac   780
tgaagtaaat gttggtgaaa gctgtagtgg aaatgaaaag gactcccttc ttattaccca   840
gaaagaacaa aaccatgagc atgaagaggg gaatgttgtt tgtcaattcc ctcgtggtgc   900
cagaagagca agtcaagaca cctccagtca tcatgtagac ttcccgagtg ctctgactcc   960
tgcagatgtc cccatggagg aacaaccaat ggatttatcc agagaaaaca tctctgagga  1020
caagaacaat tgctataaca cttccaggaa tgcagctact caagtatata gtggtgataa  1080
tattcccagg aacaagacag actcccttt cattaacaag agaatatatc atcctgagcc  1140
tgaggtggga gatattcctt atggagttcc tcaggattct acaagagcaa gtcaaggaac  1200
atctacatgc ctgcaagagt cacttgggga tgttttttct gaaaaagacc caagggaggt  1260
accagggttg cagtctaggc aagagcagcc tatctctgat cctgtccttg gtaagaatca  1320
tgaggcaaac ttaccatgtg aaagtcatca aaagagattc catagagatg ccaaactata  1380
caagtgtgaa gaatgttcta ggatgttcaa acatgccagg agcctttcat cccaccagag  1440
aactcacctg aataagaaga gtgaattgct ttgcatcacc tgtcagaaaa tattcaaacg  1500
```

```
agtttctgac cttcgaaccc atgagatcat acacatgtca gaaaagcctt tcaagtgcag    1560
cacatgtgaa aagtccttca gccacaagac caacctgaag tatcatgaga tgattcacac    1620
aggagaaatg ccttatgtct gttccctatg tagccgtcgc tttcgccaat catccactta    1680
ccatcgtcac ctgaggaatt accacagatc tgactgaagt atctaacatc ctcagcagag    1740
actggtaggg cttcagcctc agtatgtcat cttc                                1774
```

```
<210> SEQ ID NO 18
<211> LENGTH: 195
<212> TYPE: PRT
<213> ORGANISM: Mus musculus

<400> SEQUENCE: 18

Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Ile
145                 150                 155                 160

Pro Asp Asn Ala Gln Met Pro Val Asp Thr Thr Gln Asp Arg Leu Leu
                165                 170                 175

Ala Thr Gly Lys Lys Thr Val Lys Met Asn Ala Thr Pro Leu Ala Met
            180                 185                 190

Leu Leu Lys
        195
```

```
<210> SEQ ID NO 19
<211> LENGTH: 2275
<212> TYPE: DNA
<213> ORGANISM: Mus musculus

<400> SEQUENCE: 19
cacagtgcct ccctgggctt cttggcatca cccttgaagt tcaccggaga aagcagtgag     60
gtggaggaat aggtaaactt tccttcctag tggtcttgaa tgtctttttac agtacatcca    120 tcaactgtta gcattttcgt aaagtcacaa acagatatt aaactactat agttgaatct     180
ttcacaccat tgtcaccaca atggcttcac agcaggcacc agcaaaagac cttcagacca    240
acaatttaga gtttactcca actgatagtt ctggtgtgca gtgggcagaa gacatctcta    300
actcaccaag tgctcagcta aacttttccc caagtaacaa tggctgctgg gcaactcagg    360
agctgcaaag tctctggaag atgttcaact cctggttgca gccagaaaag cagactaagg    420
```

```
agcagatgat ttctcaactg gtcttggagc agtttctcct cactgggcac tgcaaggaca      480
agtatgcttt gacagagaag tggaaagcca gtggtagcga tatgaggaga ttcatggaga      540
gtctgactga tgagtgcttg aagcctcctg tcatggtcca tgtttcaatg caaggacaag      600
aagccctctt ttctgaaaac atgccattaa agaagtcat caagcttttg aaacaacagc       660
aatctgcaac aaggccaaca ccagataatg agcagatgcc agtagacacc acacaagata      720
gattattggc cacaggacaa gaaaacagtg aaaatgaatg caacaactct tgtaatgcta      780
ctgaagcaaa tgttggtgaa agctgtagtg gaaatgaaat ggactcccct cttattatcc      840
agaaagaaca gcaccctgag catgaagagg ggaatgttgt ttgtcaattc cctcatggtg      900
ccagaagagc aagtcaaggc accccagtc atcatgtaga cttcccgagt gctccgacta       960
ctgccgatgt ccccatggag gaacaaccaa aggatttatc cagagaaaac atctctgagg     1020
acaagaacaa ttgctataac acttccagaa atgcagctac tcaagtatat agtggtgata     1080
atattcccag gaacaagtca gactcccttt tcattaacaa gagaatatat catcctgagc     1140
ctgaggtggg agatattcct tatggagttc ctcaggattc tacaagagca agtcaaggaa     1200
catctcacatg cctgcaagag tcacttgggg aatgttttc tgaaaacgac ccaagggagg     1260
taccagggtt gcagtctagg caagagcagc ctatctctga tcctgtcctt cttggtaaga    1320
atcatgaggc aaacttacca tgtgaaagtc atcaaaagag attctgtaga gatgccaaac    1380
tatacaagtg tgaagaatgt tctaggatgt tcaaacatgc caggagcctt tcatcccacc    1440
agagaactca cctgaataag aagagtgaat tgctttgtgt cacctgtcag aaaatgttca    1500
aacgagtctc tgaccgccga acccatgaga tcatacacat gccagaaaag cctttcaagt    1560
gcagcacatg tgaaaagtcc ttcagccaca agaccaacct gaagtctcat gagatgattc    1620
acacaggaga aatgccttat gtctgttccc tatgtagccg tcgctttcgc caatcatcca    1680
cttaccatcg tcacctgagg aattaccaca gatctgactg aactatctaa catcctcagc    1740
agagactggt agggcttcag cctcagtatg tcatcttcaa agagagaaga atgttgcaag    1800
taaattgtac tgtcccaata atgatataac atgcttgtgg attgccactt ttatgttttg    1860
ttttgttttg ttwtttatkt tgtgtgtgtg tatgtaattt tttgtctgta tttccatatt    1920
tccacagcat aagttattag aatactttgc tgttaattct tgagttgctt cttgcttta     1980
gacagtgtct ttctggttgg cagctttata cacctgtctt tctggcacta gagttttccaa   2040
acattttctg atctccactt ttattttcta cagtgttctt gacagaagcc tggcattccc    2100
tctgacattt tctacatgtt ggggttttca tcccaagtct tagggttgca agttaaatgc    2160
attgcctctt cagacatctc atgccatgtc tactgcttac agttcaagaa tatttctcta    2220
cattactaga acgacgttca aagtggaata ataaataaat aaataatcaa caatt         2275
```

<210> SEQ ID NO 20  
<211> LENGTH: 506  
<212> TYPE: PRT  
<213> ORGANISM: Mus musculus

<400> SEQUENCE: 20

Met Ala Ser Gln Gln Ala Pro Ala Lys Asp Leu Gln Thr Asn Asn Leu  
1               5                   10                  15

Glu Phe Thr Pro Thr Asp Ser Ser Gly Val Gln Trp Ala Glu Asp Ile  
            20                  25                  30

Ser Asn Ser Pro Ser Ala Gln Leu Asn Phe Ser Pro Ser Asn Asn Gly  
        35                  40                  45

Cys Trp Ala Thr Gln Glu Leu Gln Ser Leu Trp Lys Met Phe Asn Ser

-continued

```
             50                  55                  60
Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Val Met Val His Val
        115                 120                 125

Ser Met Gln Gly Gln Glu Ala Leu Phe Ser Glu Asn Met Pro Leu Lys
        130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
        210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
        290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Asn Asp Pro Arg
            340                 345                 350

Glu Val Pro Gly Leu Gln Ser Arg Gln Glu Gln Pro Ile Ser Asp Pro
        355                 360                 365

Val Leu Leu Gly Lys Asn His Glu Ala Asn Leu Pro Cys Glu Ser His
        370                 375                 380

Gln Lys Arg Phe Cys Arg Asp Ala Lys Leu Tyr Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Arg Thr His Glu Ile Ile His Met Pro
        435                 440                 445

Glu Lys Pro Phe Lys Cys Ser Thr Cys Glu Lys Ser Phe Ser His Lys
        450                 455                 460

Thr Asn Leu Lys Ser His Glu Met Ile His Thr Gly Glu Met Pro Tyr
465                 470                 475                 480
```

```
Val Cys Ser Leu Cys Ser Arg Arg Phe Arg Gln Ser Ser Thr Tyr His
            485                 490                 495
Arg His Leu Arg Asn Tyr His Arg Ser Asp
            500                 505

<210> SEQ ID NO 21
<211> LENGTH: 2268
<212> TYPE: DNA
<213> ORGANISM: Mus musculus

<400> SEQUENCE: 21
cacagtgcct ccctgggctt cttggcatca cccttgaagt tcactggaca aagaggtgag      60
gtggaggagt aggtaaactt cccttcctag tggtcgtgaa tgtcttttac agtacatcca     120
tcaactgtta gcattttcat aaagtcacaa aacagatact aaactgctat agttgaatct     180
ttcacaccat tgtcaccaca atggcttcac agcaggcacc agcaaaagac cttcagacca     240
acaatttaga gtttactcca tctcatagtt ctggtgtgca gtgggtagaa gacatctcta     300
actcaccaag tgctcagcta aacttttctc caagtaacaa tggctgctgg gcaactcagg     360
agctgcaaag tctctggaag atgttcaact cctggttgca gccagaaaag cagactaagg     420
agcagatgat ttctcaactg gtcttggagc agtttctcct cattgggcac tgcaaggaca     480
agtatgcttt gacagagaag tggaaagcca gtggtagcga tatgaggaga ttcatggaga     540
gtctgactga tgagtgcttg aagcctcctg tcatggtcca tgtttcaatg caaggacaag     600
aagctctctt ttctgaaaac atgccattaa agaagtcat caagcttttg aaacaacagc      660
aatctgcaac aaggccaaca ccagataatg agcagatgcc agtagacacc acacaagata     720
gattattggc cacaggacaa gaaaacagtg aaaatgaatg caacaactct tgtaatgcta     780
ctgaagcaaa tgttggtgaa agctgtagtg gaaatgaaat ggactcccct cttattatcc     840
agaaagaaca gcaccctgag catgaagagg ggaatgttgt ttttcaattc cctcttgatg     900
ccagaagagc aagtcaaggc aactccagtc atcatgtaga cttccggagt gctccgactc     960
ctgcggatgt ccccatggag gaacaaccaa aggatttatc cagagaaaac atctctgagg    1020
acaagaacaa ttgctataac acttccagga atgcagctac tcaagtatat agaagtgata    1080
atattcccag gaaaaagaca gactcccttt ccattaacaa gagaatatat cattctgagc    1140
ctgaggaggg agatattcct tatggagttc ctcaggattc tacaagagca agtcaaggaa    1200
catctacatg cttgcaagag tcacttgggg aatgttttt tgaaaaagac cctagggagc    1260 taccaggggtt ggagtctagg caagaggagc ctatctctga tcctgtcttt cttggtaagg    1320
atcatgaggc aaacttacca tgtgaaagtc atcaaaagag attccgtaga gatgccaaac    1380
tattcaagtg tgaagaatgt tctaggatgt tcaaacatgc caggagcctt tcgtcccacc    1440
agagaactca cctgaataag aagagtgaat tgctttgtgt cacctgtcag aaaatgttca    1500
aacgagtctc tgaccgccga acccatgaga tcatacacat gccagaaaag cctttcaagt    1560
gcagcacatg tgaaaaagtcc ttcagccaca agaccaacct gaagtctcat gagatgattc    1620
acacaggaga aatgccttat gtctgttccc tatgtagccg tcgctttcgc caatcatcca    1680
cttaccatcg tcacctgagg aattaccaca gatctgactg aagtatctaa catcctcagc    1740
agagactggt agggcttcag cctcagtatg tcatcttcaa agagaagaa atgttgcaag     1800 taaattgtac tgtcccaata atgatataac atgcttgtgg attgccactt ttatgttttg    1860 tttttttattg tgtgtgtgtg tgtatgtaat ttttgtctg taattccat agttccacag     1920 cataagttat tagaatactt tgctgttaat tcttgagttg cttcttgctt ttagacagtg    1980
```

-continued

```
tctttctggt tggcagcttt atacacctgt ctttctggca ctagagtttc caaacatttt    2040
ctgatctcca cttttattct ctacagtggt cctgacagag gcctgccatt ccctctgaca    2100 tttttttaaca tgttggggtt tcatcccaag tcttagggtt gcaagttaaa tgcattgcct    2160
cttcagacat ctcatgtcat gtctactgct tacagttcaa gaatatttct ctacattact    2220
agaatgacgt tcaaagtgga ataataaata aaaaaataat caacaatt                 2268
```

<210> SEQ ID NO 22
<211> LENGTH: 506
<212> TYPE: PRT
<213> ORGANISM: Mus musculus

<400> SEQUENCE: 22

```
Met Ala Ser Gln Gln Ala Pro Ala Lys Asp Leu Gln Thr Asn Asn Leu
 1               5                  10                  15

Glu Phe Thr Pro Ser His Ser Ser Gly Val Gln Trp Val Glu Asp Ile
                20                  25                  30

Ser Asn Ser Pro Ser Ala Gln Leu Asn Phe Ser Pro Ser Asn Asn Gly
            35                  40                  45

Cys Trp Ala Thr Gln Glu Leu Gln Ser Leu Trp Lys Met Phe Asn Ser
        50                  55                  60

Trp Leu Gln Pro Glu Lys Gln Thr Lys Glu Gln Met Ile Ser Gln Leu
    65                  70                  75                  80

Val Leu Glu Gln Phe Leu Leu Ile Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
    210                 215                 220

Asn Val Val Phe Gln Phe Pro Leu Asp Ala Arg Arg Ala Ser Gln Gly
225                 230                 235                 240

Asn Ser Ser His His Val Asp Phe Arg Ser Ala Pro Thr Pro Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Arg Ser Asp Asn Ile Pro Arg Lys Lys Thr Asp Ser Leu Ser
    290                 295                 300

Ile Asn Lys Arg Ile Tyr His Ser Glu Pro Glu Glu Gly Asp Ile Pro
305                 310                 315                 320

Tyr Gly Val Pro Gln Asp Ser Thr Arg Ala Ser Gln Gly Thr Ser Thr
                325                 330                 335
```

```
Cys Leu Gln Glu Ser Leu Gly Glu Cys Phe Ser Glu Lys Asp Pro Arg
            340                 345                 350
Glu Leu Pro Gly Leu Glu Ser Arg Gln Glu Glu Pro Ile Ser Asp Pro
            355                 360                 365
Val Phe Leu Gly Lys Asp His Glu Ala Asn Leu Pro Cys Glu Ser His
370                 375                 380
Gln Lys Arg Phe Arg Arg Asp Ala Lys Leu Phe Lys Cys Glu Glu Cys
385                 390                 395                 400
Ser Arg Met Phe Lys His Ala Arg Ser Leu Ser Ser His Gln Arg Thr
                405                 410                 415
His Leu Asn Lys Lys Ser Glu Leu Leu Cys Val Thr Cys Gln Lys Met
                420                 425                 430
Phe Lys Arg Val Ser Asp Arg Arg Thr His Glu Ile Ile His Met Pro
            435                 440                 445
Glu Lys Pro Phe Lys Cys Ser Thr Cys Glu Lys Ser Phe Ser His Lys
        450                 455                 460
Thr Asn Leu Lys Ser His Glu Met Ile His Thr Gly Glu Met Pro Tyr
465                 470                 475                 480
Val Cys Ser Leu Cys Ser Arg Arg Phe Arg Gln Ser Ser Thr Tyr His
                485                 490                 495
Arg His Leu Arg Asn Tyr His Arg Ser Asp
                500                 505

<210> SEQ ID NO 23
<211> LENGTH: 1774
<212> TYPE: DNA
<213> ORGANISM: Mus musculus

<400> SEQUENCE: 23
cacagtgcct ccctgggctt cttggcatca ccattgaagt tcactggaga aagaggtgag      60
gtggagaagt aggtaaactt ccctttcttg tggtcttgaa tgtcttttac agtacatccg     120
tcaactgtta gcattttcct aaagtcacaa aacagatact aaactgctat agttgaatct     180
ttcagaccat tgtcaccaca atggcttcac agcaggcacc agcaaaagac cttcagacca     240
acaatttaga gtttactcca actgatagtt ctggtgtgca gtgggcagaa gacatctcta     300
actcaccaag tgctcagcta aacttttccc caagtaacaa tggctgctgg gcaactcagg     360
agctgcaaag tctctggaag atgttcaact cctggttgca gccagaaaag cagactaagg     420
agcagatgat ttctcaactg gtcttggagc agtttctcct cactgggcac tgcaaggaca     480
agtatgcttt gacagagaag tggaaagcca gtggtagcga tatgaggaga ttcatggaga     540
gtctgactga tgagtgcttg aagcctcctg tcatggtcca tgtttcaatg caaggacaag     600
aagccctctt ttctgaaaac atgccattaa agaagtcat caagctttg aaacaacagc     660
aatctgcaac aaggccaata ccagataatg agcagatgcc agtagacacc acacaagata     720
gattattggc cacaggcaag aaaacagtga aatgaatgc aacacctctt gcaatgctac     780
tgaagtaaat gttggtgaaa gctgtagtgg aaatgaaaag gactcccttc ttattaccca     840
gaaagaacaa aaccatgagc atgaagaggg gaatgttgtt tgtcaattcc ctcgtggtgc     900
cagaagagca agtcaagaca cctccagtca tcatgtagac ttcccgagtg ctctgactcc     960
tgcagatgtc cccatggagg aacaaccaat ggatttatcc agagaaaaca tctctgagga    1020
caagaacaat tgctataaca cttccaggaa tgcagctact caagtatata atggtgataa    1080
tattcccagg aacaagacag actcccttt cattaacaag agaatatatc atcctgagcc    1140
```

-continued

```
tgaggtggga gatattcctt atggagttcc tcaggattct acaagagcaa gtcaaggaac    1200
atctacatgc ctgcaagagt cacttgggga atgttttcct gaaaaagacc caagggaggt    1260
accagggttg cagtctaggc aagagcagcc tatctctgat cctgtccttg gtaagaatca    1320
tgaggcaaac ttaccatgtg aaagtcatca aaagagattc catagagatg ccaaactata    1380
caagtgtgaa gaatgttcta ggatgttcaa acatgccagg agcctttcat cccaccagag    1440
aactcacctg aataagaaga gtgaattgct ttgcatcacc tgtcagaaaa tattcaaacg    1500
agtttctgac cttcgaaccc atgagatcat acacatgtca gaaaagcctt tcaagtgcag    1560
cacatgtgaa aagtccttca gccacaagac caacctgaag tatcatgaga tgattcacac    1620
aggagaaatg ccttatgtct gttccctatg tagccgtcgc tttcgccaat catccactta    1680
ccatcgtcac ctgaggaatt accacagatc tgactgaagt atctaacatc ctcagcagag    1740
actggtaggg cttcagcctc agtatgtcat cttc                                1774
```

<210> SEQ ID NO 24
<211> LENGTH: 195
<212> TYPE: PRT
<213> ORGANISM: Mus musculus

<400> SEQUENCE: 24

```
Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Ser Ala Thr Arg Pro Ile
145                 150                 155                 160

Pro Asp Asn Glu Gln Met Pro Val Asp Thr Thr Gln Asp Arg Leu Leu
                165                 170                 175

Ala Thr Gly Lys Lys Thr Val Lys Met Asn Ala Thr Pro Leu Ala Met
            180                 185                 190

Leu Leu Lys
        195
```

<210> SEQ ID NO 25
<211> LENGTH: 2273
<212> TYPE: DNA
<213> ORGANISM: Mus musculus

<400> SEQUENCE: 25

```
cacagtgcct ccctgggctt cttggcatca cccttgaagt tcactggaga aagaggtgag     60
gtggaggaat aggtaaactt tccttcctag tggtcttgaa tgtcttttac agtacatcca    120
```

```
tcaactgtta gcattttcgt aaagtcacaa aacagatatt aaactactat agttgaatct    180
ttcacaccat tgtcaccaca atggcttcac agcaggcacc agcaaaagac cttcagacca    240
acaatttaga gtttactcca actgatagtt ctggtgtgca gtgggcagaa gacatctcta    300
actcaccaag tgctcagcta aacttttccc caagtaacaa tggctgctgg gcaactcagg    360
agctgcaaag tctctggaag atgttcaact cctggttgca gccagaaaag cagactaagg    420
agcagatgat ttctcaactg gtcttggagc agtttctcct cactgggcac tgcaaggaca    480
agtatgcttt gactgagaag tggaaagcca gtggtagcga tatgaggaga ttcatggaga    540
gtctgactga tgagtgcttg aagcctcctg tcatggtcca tgtttcaatg caaggacaag    600
aagccctctt ttctgaaaac atgccattaa agaagtcat caagcttttg aaacaacagc     660
aatctgcaac aaggccaaca ccagataatg agcagatgcc agtagacacc acacaagata    720
gattattggc cacaggacaa gaaaacagtg aaaatgaatg caacaactct tgtaatgcta    780
ctgaagcaaa tgttggtgaa agctgtagtg gaaatgaaat ggactccctt cttattatgc    840
agaaagaaca gcaccctgag catgaagagg ggaatgttgt ttgtcaattc cctcatggtg    900
ccagaagagc aagtcaaggc accccagtc atcatgtaga cttcccgagt gctccgacta    960
ctgccgatgt ccccatggag gaacaaccaa aggatttatc cagagaaaac atctctgagg   1020
acaagaacaa ttgctataac acttccagaa atgcagctac tcaagtatat agtggtgata   1080
atattcccag gaacaagtca gactcccttt tcattaacaa gagaatatat catcctgagc   1140
ctgaggtggg agatattcct tatggagttc ctcaggattc tacaagagca agtcaaggaa   1200
catctacatg cctgcaagag tcacttgggg aatgttttc tgaaaagac cctagggagg    1260 taccagggtt gcagtctagg caagagcagc ttatctctga tcctgtcctt cttggtaaga   1320
atcatgaggc aaacttacca tgtgaaagtc atcaaaagag attctgtaga gatgccaaac   1380
tatacaagtg tgaagaatgt tctaggatgt tcaaacatgc caggagcctt tcatcccacc   1440
agagaactca cctgaataag aagagtgaat tgctttgtgt cacctgtcag aaaatgttca   1500
aacgagtctc tgaccgccga acccatgaga tcatacacat gccagaaaag ctttcaagt    1560 gcagcacatg tgaaaagtcc ttcagccaca agaccaacct gaagtctcat gagatgattc   1620
acacaggaga aatgccttat gtctgttccc tatgtagccg tcgctttcgc caatcatcca   1680
cttaccatcg tcacctgagg aattaccaca gatctgactg aactatctaa catcctcagc   1740
agagactggt agggcttcag cctcagtatg tcatcttcaa agagagaaga atgttgcaag   1800
taaattgtac tgtcccaata atgatataac atgcttgtgg attgccactt ttatgttttg   1860
ttttgttttt tattttgtgt gtgtgtgtat gtaattttt gtctgtattt ccatagttcc    1920
acagcataag ttattagaat actttgctgt taattcttga gttgcttctt gcttttagac   1980
agtgtctttc tggttgacag ctttataaac ctgtctttct ggcactagag tttccaaaca   2040
ttttctgatc tccacttta ttctctacag tgttcttgac agaagcctgg cattccctct    2100
gacatttttc tacatgttgg ggttttcatc ccaagtctta gggttgcaag ttaaatgcat   2160
tgcctcttca gacatctcat gccctgtcta ctgcttacag ttcaagaata tttctctaca   2220
ttactagaac gacattcaaa gtggaataat aaataaataa ataatcaaca att           2273
```

<210> SEQ ID NO 26
<211> LENGTH: 506
<212> TYPE: PRT
<213> ORGANISM: Mus musculus

<400> SEQUENCE: 26

-continued

```
Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
                35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65              70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
            115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
            195                 200                 205

Ser Leu Leu Ile Met Gln Lys Glu Gln His Pro Glu His Glu Glu Gly
    210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
            245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
    275                 280                 285

Val Tyr Ser Gly Asp Asn Ile Pro Arg Asn Lys Ser Asp Ser Leu Phe
    290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Lys Asp Pro Arg
            340                 345                 350

Glu Val Pro Gly Leu Gln Ser Arg Gln Glu Gln Leu Ile Ser Asp Pro
            355                 360                 365

Val Leu Leu Gly Lys Asn His Glu Ala Asn Leu Pro Cys Glu Ser His
    370                 375                 380

Gln Lys Arg Phe Cys Arg Asp Ala Lys Leu Tyr Lys Cys Glu Glu Cys
385                 390                 395                 400

Ser Arg Met Phe Lys His Ala Arg Ser Leu Ser Ser His Gln Arg Thr
    405                 410                 415

His Leu Asn Lys Lys Ser Glu Leu Leu Cys Val Thr Cys Gln Lys Met
```

```
                       420                 425                 430
Phe Lys Arg Val Ser Asp Arg Arg Thr His Glu Ile Ile His Met Pro
        435                 440                 445
Glu Lys Pro Phe Lys Cys Ser Thr Cys Glu Lys Ser Phe Ser His Lys
    450                 455                 460
Thr Asn Leu Lys Ser His Glu Met Ile His Thr Gly Glu Met Pro Tyr
465                 470                 475                 480
Val Cys Ser Leu Cys Ser Arg Arg Phe Arg Gln Ser Ser Thr Tyr His
                485                 490                 495
Arg His Leu Arg Asn Tyr His Arg Ser Asp
            500                 505

<210> SEQ ID NO 27
<211> LENGTH: 1524
<212> TYPE: DNA
<213> ORGANISM: Mus musculus

<400> SEQUENCE: 27
atggcatcac agttcagaga aacctttatg cccaagtcat catcaaatga ctttgaatta      60
gatgatgcaa gtttattcc aacccgggct tctgctctgc agtggggaga agacatcttt      120
cactcaccaa gtgttcagtt caatgttttc ccaaataaca atggctccct ggcaaagcag      180
gagctgcaaa cactctggga gatgtttacc tcctggttgc agccagaaaa gcagactaag      240
gagcagatga tttctcaact ggtcttggag cagtttctca tcactgggca ctgcaaggac      300
aagtatgctt tgacagagaa gtggaaagcc agtggcagaa acatggagag attcatggag      360
agtctgactg atgagtgctt gaagcctcct gtcatgatcc atgttgccat gcatgggcag      420
gaagcccttt tttctgagaa catgccctta aaagaagtca tcacactttt ggaacaacag      480
aaagtagcaa caactccaac tcaagagaat gcaagggcac tcttggagat ccccaaagat      540
aggttcttga caacagggca tgaaaataca gacgatggct gccaaagtcc ctggaaggct      600
agcgttggaa atggcagtgt aatagtatt ggaagtatga gggattccct tctaactttc      660
cagagagtac agtatccgga gcttgaagag ggggatgttt tttacacagt tccacaggtt      720
gtcagaagag caagtcaagg tacttccagg ccccaggaaa tatccctgag ggcaccttct      780
tctgaaggta tccttaagga ggtacaacca gtgcttctct ccctaacaga gcagcctgag      840
gatactggga atagccacaa caatattgat ataagtggtg gtggtgttag tctcacacat      900
gagggagatt ctgtttttcat tatccagaga gagcagtatt ctgaacctga tgtggaaagt      960
gtttcttatg gagtgcctcg ggatttaaga gtagcaatgt gtggtccctc caggtccctg     1020
gaggagtccc tgtgggcagt ttcttctgat gttgtccctg tggaggtacc aggtttcctc     1080
tctaggccag agcagcctac cccgaagcct gtccctcttt tccagaatca tgaggcaaat     1140
tccacctttg agggttacca agagagactc cagagagatc ccaaaccgta caatgtgag      1200
gaatgtccca gaaccttcaa atatccctgc aacctctcca tccaccagaa acacacagg      1260
aaggagaggc cattttttctg taaggagtgc cagataggct tttaccaaaa gtcagaactt     1320
cacgatcatg aggtcataca caaggcagag aagccttttcg catgcagtac gtgtggaagg     1380
gccttcagat acaagaccaa cctgcaggct catgagagaa ttcacacagg agaagcct       1440
tattcttgct ccctgtgtaa tagtagcttc cgccagtcat ccacattcca ccgtcacttg     1500
aggaagttcc acaaatcaga atga                                            1524

<210> SEQ ID NO 28
<211> LENGTH: 6017
```

<212> TYPE: DNA
<213> ORGANISM: Artificial
<220> FEATURE:
<223> OTHER INFORMATION: Zscan4c promoter-Emerald plasmid

<400> SEQUENCE: 28

| | | | | | | |
|---|---|---|---|---|---|---|
| gtcctgctat | tctgtgcatt | gaaacatgtc | atgtctctgt | ccctgatgtt | ttacttgaag | 60 |
| aatatggcat | ataagttcct | tcttctttgc | tttatagaat | ataatttaaa | ttataataat | 120 |
| ttcctctcta | aaagtaatgt | ttttgttaag | acctattaat | ttgttataaa | ttttgttggg | 180 |
| attacaaata | cttttctgag | agaagttctc | atgttgtaca | aactctattc | atacaaaata | 240 |
| ccttttcata | caaaagaaga | attgttgttt | tatccccaat | tctaactctt | agtataaata | 300 |
| aaataataca | gtgggttgtt | ctgatgctgc | ttatattatc | atgctaaata | ttggtttctt | 360 |
| aatctgtggt | tgtccacaaa | gtacagagcc | atacatccac | ccaatgatgc | tatttgaata | 420 |
| ttgtcccgaa | atacaactgg | tcaaaaaaaa | aaaaaaaaaa | aagcaacttg | ctatgattgg | 480 |
| tcattggagg | gagaaaggtt | ggatttgagg | attaagtgaa | gagattgctg | gtagaggaag | 540 |
| agaaagaaga | aagaagactt | aagtggagga | ggctgtcatg | ggaagtgatg | aaatataaat | 600 |
| tcttggaaca | gagaaacagc | aagtataagg | gacttgatcc | ttggggaata | agttagaata | 660 |
| gctgtaaatc | tgccttattt | aggcttgagt | ttataaataa | aatagctaga | ttgtgtttct | 720 |
| tttatatgga | caagctagca | tggatcactt | ccaacagcaa | caaccaaaaa | atgatttaaa | 780 |
| agcatggctt | ctaccttcct | agtagtagcg | gttccagggc | aaccttacta | cttctatcat | 840 |
| ctttttcttc | ttcttcttct | tcttcttctt | cttcttcttc | ttcttcttct | tcttcttctt | 900 |
| cttcttcttc | ttcttcttct | tcttcttctt | ctccgcctcc | tcctcctcct | cctcctcctc | 960 |
| ctcctcctcc | tccttcttct | tcttcttctt | cttcatgctt | ttgcatgctt | tttttttttt | 1020 |
| tttcggtgat | accttctgtt | catgcaagcc | tggctatgtt | tgaggtctat | ttgaaatcca | 1080 |
| gacttgcctc | aaacggatag | agatgctcct | ggatctgttt | tctgatctag | gattaagtgt | 1140 |
| ttagcaggga | ttaaaggcac | taacctcctt | caagtagtct | aattgctaaa | ttgaattgtg | 1200 |
| ccctttgaaa | ttcacatgca | ggaagaaaat | agtgaacaac | agtaaaatgt | ttattgttct | 1260 |
| catgaaaaaa | cactttcatc | tgaatgtttc | ttcttgttag | tattgcatta | attaattaat | 1320 |
| atactgaaca | tcatcattag | caactaaaac | aaatgataca | tttttacatg | ttgagtcaat | 1380 |
| cattgtttta | acaaatggct | aatttatttg | aagaattagt | agtgctttct | ttgtcatgtg | 1440 |
| gcatttttt | tttttttat | aaaggaagg | gcagctttag | gtataagcat | tcaaaatttt | 1500 |
| tggttttgtg | aatgtaaaag | atttcagatt | ttagaagttg | taaatcactg | attttccagt | 1560 |
| ctatttgggg | gtaagggaaa | ttaaggttct | atgttttaga | ctgaagttca | gcacaaactc | 1620 |
| agtgttagaa | gattaaacat | caacatgtga | atttaggggt | cacaattgaa | cctatcaatt | 1680 |
| agcatgattg | gacaaatcaa | ttcacaaagg | caaccacatt | taaatccacc | actctggaat | 1740 |
| taatggcaag | gatgtgtcaa | cctgatccat | actgtagggc | tattatgtct | aggcatacaa | 1800 |
| gggaaaaaat | agtctctaga | tgaaataaaa | gaaatgaaat | aaaagacata | agttcccttc | 1860 |
| agcctctatc | tttactatat | tgtgctacag | acaacttctg | gattcttctt | gcccttatctt | 1920 |
| cttgatccca | ctatcaagga | ttctacagag | ttcactgaag | cacttaggat | ccaatctctc | 1980 |
| tggaaaccag | gaaattttaa | cgagtttcca | ttgactacta | tgtgagaaca | caggatcaga | 2040 |
| ggtcatagaa | tataaatgcc | aatcttggaa | ttcctcttaa | gtgtggtact | atttccattc | 2100 |
| actacagtga | cttacaacac | ttgactagga | gatgatcttc | ttccaaagaa | gagtcaatca | 2160 |
| ttgcattaga | gatgcaaaac | tagagctgag | ttaggattcc | ttacgtgatt | caatcagcag | 2220 |

```
gaaaagatgt ctttccctat ttgtttgctt gcttgtattt tatgcccct tttggcatta    2280 tctgttcccc taggtcagac tgaccttgga tctctgggct taataggcag tgctggggac    2340
tacagactct cctgattcaa cttctattac tttgagtact atggataaaa tggtaatctg    2400
ccccacccag ggacaggagg tttgatagaa tcactgtgtg aatttaatcg tcatcagtaa    2460
ccgactaacg gaagccaggg gctataaaag ggaaccaatc ctaatagaac ctcagatgaa    2520
gcagagccaa ggcagggaca cacagtgcct ccctgggctt cttggcatca cccttgaagt    2580
tcactggaca aagaggtgag gtggaggagt aggtaaactt cccttcctag tggtcgtgaa    2640
tgtgtaagta tatgtgtatt tatgtgtgtg tttgtgtgtt tatttgtgga cttgtgagaa    2700
gattcatcac aattatgggt agatctcagt agttcaatat tgccttttgg atgctttact    2760
gatcaagagg ttgattttc taaactctaa agaaaactct gacttggtaa ccattcaggt    2820
atgtgtgtgg atatttgttt gcttctctgt gaatttaata ttcctggtta ttcattttaa    2880
atattttctt atgaaagtat tattctctgg cactttagaa tgacacagaa gggtgaaact    2940
taaaatttaa ggaacggcat aataactccc atcttttcca agggggaaa atacaacatt    3000 gctgtgttct taagatctca tgacagatct aagcaccta gatacaggac tttctggtta    3060
ttgagtcaat tttttttcta ctttcagtt gttttgccca tttccaattc catgcaagca    3120
gattgaaagg actatagtga aacatttact gtcaggaacc aataaaacca tctgtgacac    3180
aaatctcatt tggttttgtg tttgttttgt taacattaat tatgtgtttc ttccttttt    3240 aaattcacag cttttacagt acatccatca actgttagca ttttcataaa gtcacaaaac    3300
agatactaaa ctgctatagt tgaatctttc acaccattgt caccacaagg gcgaattcga    3360
cccagctttc ttgtacaaag tggttgatgc tgttaacatg gtgagcaagg gcgaggagct    3420
gttcaccggg gtggtgccca tcctggtcga gctggacggc gacgtaaacg gccacaagtt    3480
cagcgtgtcc ggcgagggcg agggcgatgc cacctacggc aagctgaccc tgaagttcat    3540
ctgcaccacc ggcaagctgc ccgtgccctg gcccaccctc gtgaccacct tcacctacgg    3600
cgtgcagtgc ttcgcccgct accccgacca catgaagcag cacgacttct tcaagtccgc    3660
catgcccgaa ggctacgtcc aggagcgcac catcttcttc aaggacgacg gcaactacaa    3720
gacccgcgcc gaggtgaagt tcgagggcga caccctggtg aaccgcatcg agctgaaggg    3780
catcgacttc aaggaggacg gcaacatcct ggggcacaag ctggagtaca actacaacag    3840
ccacaaggtc tatatcaccg ccgacaagca gaagaacggc atcaaggtga acttcaagac    3900
ccgccacaac atcgaggacg gcagcgtgca gctcgccgac cactaccagc agaacccc    3960 catcggcgac ggccccgtgc tgctgcccga caaccactac ctgagcaccc agtccgccct    4020
gagcaaagac cccaacgaga gcgcgatca catggtcctg ctggagttcg tgaccgccgc    4080
cgggatcact ctcggcatgg acgagctgta caagtaatga taagtttaaa cggggggaggc    4140 taactgaaac acggaaggag acaataccgg aaggaacccg cgctatgacg gcaataaaaa    4200
gacagaataa aacgcacggg tgttgggtcg tttgttcata aacgcggggt tcggtcccag    4260
ggctggcact ctgtcgatac cccaccgaga ccccattggg ccaatacgc ccgcgtttct    4320 tccttttccc cacccaccc cccaagttcg ggtgaaggcc cagggctcgc agccaacgtc    4380
ggggcggcag gccctgccat agcagatctg cgcagctggg gctctagggg gtatccccac    4440
gcgccctgta gcggcgcatt aagcgcggcg ggtgtggtgg ttacgcgcag cgtgaccgct    4500
acacttgcca gcgccctagc gcccgctcct ttcgctttct tcccttcctt tctcgccacg    4560
ttcgccggct ttccccgtca gctctaaat cgggggctcc ctttagggtt ccgatttagt    4620
```

```
gctttacggc acctcgaccc caaaaaactt gattagggtg atggttcacg tagtgggcca    4680
tcgccctgat agacggtttt tcgccctttg acgttggagt ccacgttctt taatagtgga    4740
ctcttgttcc aaactggaac aacactcaac cctatctcgg tctattcttt tgatttataa    4800
gggattttgc cgatttcggc ctattggtta aaaatgagc tgatttaaca aaaatttaac     4860
gcgaattaat tctgtggaat gtgtgtcagt tagggtgtgg aaagtcccca ggctccccag    4920
caggcagaag tatgcaaagc atgcatctca attagtcagc aaccaggtgt ggaaagtccc    4980
caggctcccc agcaggcaga gtatgcaaa gcatgcatct caattagtca gcaaccatag     5040
tcccgcccct aactccgccc atcccgccc taactccgcc cagttccgcc cattctccgc     5100
cccatggctg actaattttt tttatttatg cagaggccga ggccgcctct gcctctgagc    5160
tattccagaa gtagtgagga ggcttttttg gaggcctagg cttttgcaaa aagctcccgg    5220
gagcttgtat atccattttc ggatctgatc agcacgtgtt gacaattaat catcggcata    5280
gtatatcggc atagtataat acgacaaggt gaggaactaa accatggcca agcctttgtc    5340
tcaagaagaa tccaccctca ttgaaagagc aacggctaca atcaacagca tccccatctc    5400
tgaagactac agcgtcgcca gcgcagctct ctctagcgac ggccgcatct tcactggtgt    5460
caatgtatat cattttactg ggggaccttg tgcagaactc gtggtgctgg cactgctgc     5520
tgctgcggca gctggcaacc tgacttgtat cgtcgcgatc ggaaatgaga caggggcat     5580
cttgagcccc tgcggacggt gccgacaggt gcttctcgat ctgcatcctg ggatcaaagc    5640
catagtgaag acagtgatg gacagccgac ggcagtgggg attcgtgaat tgctgccctc     5700
tggttatgtg tgggagggct aagcacttcg tggccgagga gcaggactga cacgtgctac    5760
gagatttcga ttccaccgcc gccttctatg aaaggttggg cttcggaatc gttttccggg    5820
acgccggctg gatgatcctc cagcgcgggg atctcatgct ggagttcttc gcccacccca    5880
acttgtttat tgcagcttat aatggttaca aataaagcaa tagcatcaca aatttcacaa    5940
ataaagcatt ttttttcactg cattctagtt gtggtttgtc caaactcatc aatgtatctt    6000
atcatgtctg tataccg                                                    6017
```

<210> SEQ ID NO 29
<211> LENGTH: 2230
<212> TYPE: DNA
<213> ORGANISM: Homo sapiens

<400> SEQUENCE: 29

```
ccttgtaatt cataaatctc tgaaaactta aagtttgag caaagtttg tcatgtttct       60
atgagtaatt tataataaaa cttgatcaga atttgtgaga ctagcgtttg tctttatatt    120
ttccttttt ttttttttt tttgagacac agtctcgctc tgtcgtccag gctggagtgc     180
cgtggcgtaa tctcggctca ctgcaacctc tgcctcctgg attcaaacaa ttcttctgcc    240
tcagcctcct gagtagctgg gattacagga ccagtgatgc tatagaacac tgtattagag    300
acatggagct ggggctggat gaagattcca tcagtaattc aatcaacaga caagtgttat    360
ccaatcacgt ctttaaatca atcactgaca tggagctggg gctggatgaa gattccatca    420
gtaattcaat caacagacaa gtgttatcca atcacgtctt taaatcaatc actgatccca    480
gcccctataa aagggagcag ccttaggagg cacatcagat aaacccagtg tggaaagcta    540
gtcacacatc agctcagtgt tcggcccggg attacccagt caaccaagga gcttgcagtt    600
ttaaagaatc caccaactgt tgaaacaaat ccctagagac acaaggcaag agactgaatc    660
atcaaagtaa agtctctctg agaattattg ctaagaatgg ctttagatct aagaaccata    720
```

-continued

```
tttcagtgtg aaccatccga gaataatctt ggatcagaaa attcagcgtt tcaacaaagc      780
caaggacctg ctgttcagag agaagaaggg atttctgagt tctcaagaat ggtgctcaat      840
tcatttcaag acagcaataa ttcatatgca aggcaggaat tgcaaagact ttataggatc      900
tttcactcat ggctgcaacc agaaaagcac agcaaggatg aaattatttc tctattagtc      960
ctggagcagt ttatgattgg tggccactgc aatgacaaag ccagtgtgaa agagaaatgg     1020
aaatcaagtg gcaaaaactt ggagagattc atagaagacc tgactgatga cagcataaat     1080
ccacctgcct tagtccacgt ccacatgcag ggacaggaag ctctcttttc tgaggatatg     1140
cccttaagag atgtcattgt tcatctcaca aaacaagtga atgcccaaac cacaagagaa     1200
gcaaacatgg ggacaccctc ccagacttcc caagatactt ccttagaaac aggacaagga     1260
tatgaagatg aacaagatgg ctggaacagt tcttcgaaaa ctactcgagt aaatgaaaat     1320
attactaatc aaggcaatca aatagtttcc ctaatcatca tccaggaaga gaacggtcct     1380
aggcctgaag agggaggtgt ttcttctgac aacccataca actcaaaaag agcagagcta     1440
gtcactgcta gatctcagga agggtccata aatggaatca ctttccaagg tgtccctatg     1500
gtgatgggag cagggtgtat ctctcaacca gagcagtcct cccctgagtc tgcccttacc     1560
caccagagca atgagggaaa ttccacatgt gaggtacatc agaaaggatc ccatggagtc     1620
caaaatcat acaaatgtga agaatgcccc aaggtcttta gtatctctg tcacttatta     1680
gctcaccaga gaagacacag gaatgagagg ccatttgttt gtcccgagtg tcaaaaaggc     1740
ttcttccaga tatcagacct acgggtgcat cagataattc acacaggaaa gaagcctttc     1800
acatgcagca tgtgtaaaaa gtccttcagc cacaaaacca acctgcggtc tcatgagaga     1860
atccacacag gagaaaagcc ttatacatgt ccctttttgta agacaagcta ccgccagtca     1920
tccacatacc accgccatat gaggactcat gagaaaatta ccctgccaag tgttccctcc     1980
acaccagaag cttcctaagc tgctggtctg ataatgtgta taaatatgta tgcaagtatg     2040
tatattccta tagtatttat ctacttagga tataagatat aatctcctga ttatgctttc     2100
aatttattgt cttgcttcat taaaatgtaa ggctaaggag agcatggaat ttgtcagttt     2160
tgttcactaa agtattccaa gtggttggga aagtggaaca tttccaagaa ccaataaatt     2220
tctgttgaat                                                           2230
```

<210> SEQ ID NO 30
<211> LENGTH: 433
<212> TYPE: PRT
<213> ORGANISM: Homo sapiens

<400> SEQUENCE: 30

```
Met Ala Leu Asp Leu Arg Thr Ile Phe Gln Cys Glu Pro Ser Glu Asn
1               5                   10                  15

Asn Leu Gly Ser Glu Asn Ser Ala Phe Gln Gln Ser Gln Gly Pro Ala
            20                  25                  30

Val Gln Arg Glu Glu Gly Ile Ser Glu Phe Ser Arg Met Val Leu Asn
        35                  40                  45

Ser Phe Gln Asp Ser Asn Asn Ser Tyr Ala Arg Gln Glu Leu Gln Arg
    50                  55                  60

Leu Tyr Arg Ile Phe His Ser Trp Leu Gln Pro Glu Lys His Ser Lys
65                  70                  75                  80

Asp Glu Ile Ile Ser Leu Leu Val Leu Glu Gln Phe Met Ile Gly Gly
                85                  90                  95

His Cys Asn Asp Lys Ala Ser Val Lys Glu Lys Trp Lys Ser Ser Gly
```

```
                    100                 105                 110
Lys Asn Leu Glu Arg Phe Ile Glu Asp Leu Thr Asp Asp Ser Ile Asn
            115                 120                 125

Pro Pro Ala Leu Val His Val His Met Gln Gly Gln Glu Ala Leu Phe
130                 135                 140

Ser Glu Asp Met Pro Leu Arg Asp Val Ile Val His Leu Thr Lys Gln
145                 150                 155                 160

Val Asn Ala Gln Thr Thr Arg Glu Ala Asn Met Gly Thr Pro Ser Gln
                165                 170                 175

Thr Ser Gln Asp Thr Ser Leu Gly Thr Gly Gln Gly Tyr Glu Asp Glu
            180                 185                 190

Gln Asp Gly Trp Asn Ser Ser Lys Thr Thr Arg Val Asn Glu Asn
            195                 200                 205

Ile Thr Asn Gln Gly Asn Gln Ile Val Ser Leu Ile Ile Gln Glu
        210                 215                 220

Glu Asn Gly Pro Arg Pro Glu Glu Gly Gly Val Ser Ser Asp Asn Pro
225                 230                 235                 240

Tyr Asn Ser Lys Arg Ala Glu Leu Val Thr Ala Arg Ser Gln Glu Gly
                245                 250                 255

Ser Ile Asn Gly Ile Thr Phe Gln Gly Val Pro Met Val Met Gly Ala
            260                 265                 270

Gly Cys Ile Ser Gln Pro Glu Ser Ser Pro Glu Ser Ala Leu Thr
            275                 280                 285

His Gln Ser Asn Glu Gly Asn Ser Thr Cys Glu Val His Gln Lys Gly
            290                 295                 300

Ser His Gly Val Gln Lys Ser Tyr Lys Cys Glu Glu Cys Pro Lys Val
305                 310                 315                 320

Phe Lys Tyr Leu Cys His Leu Leu Ala His Gln Arg His Arg Asn
                325                 330                 335

Glu Arg Pro Phe Val Cys Pro Cys Gln Lys Gly Phe Phe Gln Ile
            340                 345                 350

Ser Asp Leu Arg Val His Gln Ile Ile His Thr Gly Lys Lys Pro Phe
            355                 360                 365

Thr Cys Ser Met Cys Lys Lys Ser Phe Ser His Lys Thr Asn Leu Arg
            370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
                405                 410                 415

Thr His Glu Lys Ile Thr Leu Pro Ser Val Pro Ser Thr Pro Glu Ala
            420                 425                 430

Ser

<210> SEQ ID NO 31
<211> LENGTH: 4996
<212> TYPE: DNA
<213> ORGANISM: Mus musculus

<400> SEQUENCE: 31
ccaaagaggt tctatgggaa cccctaaaca actcaggata ttgtcaaaac tacatttcct      60
tctctctcca gctcttatca taactaaatc cactgcccag gggccaatat ctgattctct     120
agaatataaa gacaaaggag tactataagg tcagtcagct cagtaggctg aattattggt     180
actcactcag ttgtgggtgt catctgtgga cccaccacac ccaggtaaag aaagcaactc     240
```

```
atccagaaca ataaagactt ggtcatcaaa aatccatcta gccaggcttg gtggcacact    300
cctttaatct accccccttt tttagattta gtgtttctct gtgtagccct ggctgatctt    360
caattcactt tgtagagtag gctgtactag aactgagagc tccacctgcc tctgctttac    420
tttcattaca tggttatcag tctgtgcatt gaagaccctta ggaggggtat tttacttaag    480
attttggtaa taaaaacaaa tattgtctga tcattgtggt acatacccttt aatcccagga    540 cttgggaggc agaggcaagt ggatttaagc ccagtttaaa atctgattcc aggacagcag    600
gagctacata aagagagcc tgtctccaaa acaaacaaa caaacaaaca aacaaacagt    660
ccccaaccaa aaaacaaaa caaaacaaaa cacaacaacc aaccaaccaa ccatcatatg    720
aaaccattta aagataaata aaaccaaaaa tttacaccca cttttttataa aagtagtata    780 attcttccta ggttttgtgt ttcatactca aataatattg ccatccagtg gcatttaatg    840
tgaaaatttc tttcaaaggc ctgtgtgcta agtaaaactt agcccagtgt gtgctagtgt    900
tcatttaaac aacaccccct ctctctgaac acaaacaaat atatgttctc tgcacctcat    960
ggaactttct ctaaaactga ccacattctt ggacataaag taagtctcaa cagatagaag   1020
aaatttgaaa taactcagtg tatcctgtga ggccaccaca gaataaagct tgatatcaac   1080
aacaaagaaa caacagaaag ctcacaaaac acatggaaac tatacaattt actactgcat   1140
gaagaccaaa gtaaagaaat taaagacccc atagaattga ctagaaatgc atatacacca   1200
tacccaaaat catgggacac gagaaagggg gaagttcttt tatttttatt ttcctgagac   1260
agggtttctc tgtatagccc tggctttcct ggaactcact tgtagacca ggctggcctt   1320 gaactcagaa atctgcctgc ctcccaagtg ctgggattaa aggtgtgtgc caccactgcc   1380
ctgctaaagg ggaatgttct aaaggacaag gtcacaggac caaatgccta caaaaacaaa   1440
caaacaacta aagagaagcc aagggtgga gtctcacacc tttaatccca tcccttgaga   1500
ggaaggtggg tctctgagtt caagttcagc ctagtctgca gatccaattc caggactgcc   1560
aaggctacaa agagaaaccg tgtttctgga aaagagaagc agacctagag aaatcttgta   1620
ctagcaactt aacagcacac ctaaaagctc taggacaacc acaggaagaa ggagtacacg   1680
gcaagaaata aactgaggac tgaaatcaat aaaatagaaa caaagggaac ccttcatcag   1740
ttctttgaga aaatcagcgg gattgcaaac ccttattcaa attaactgac agaccccaga   1800
gagagagaac aggcagatga acaaaatcaa atgaaagag ggtggtgagg tggggaagtc   1860
tctaagaagt gccagagatc tgggatgggg aaggctccca ggagccaatg caggatcaag   1920
ccccatttca cttcctggtg ccccttttaat agttgaataa cacatttttat atttttttctt   1980 ttctaaattt gctatgcctg ttttaagcgc tcgttgtgag tcttaaccag agggcaaaat   2040
ctatgctggg tatttttgag actccctttt caatgcaact aatctgagtc ttattcaact   2100
gaatctcaag cagactctta agactagggc aaaaggcagt cacattcctt caccaaatat   2160
cccaagagca gcctctagtc cacatactga catccttctc ccacagttca aatcaccctc   2220
agcatcaatg tcttccatct tcctactaga atggttcact aagcctaact taaagcactt   2280
cactactttc tacatccaaa gccagcaagt caacattccc caacccaaaa catgataaag   2340
cctatccagt aacaccccag tccccagtac caacttctgc attagttagg gctctccaga   2400
gtcagagaaa tcatcggatg tctctatata tgaaggggat tgttgtctg cagtgcatct   2460 aacccagaaa tgggcagctg tgaatgggaa accccacttc acgagaaaaa tttatttca   2520 atgatttaaa aaagaagtg cctaggaaat caacaggata ttcctttgag tatgtctagg   2580
agggcctttc agagaacaag agcgaagcgc catgctgtgg gcatccatcc aatagattgg   2640
```

```
gcacataggg ataaaagaaa ggcagtgagt gagtgcaggt agtctgcctc tctgctttat    2700
ggccactgag gtgaagacct tagctctgac acctagacag agacttagct tgtatcaggg    2760
ataagctttc taactgatca cccagtacaa agtggtcagc ccttctgatg gctatgcttc    2820
gttgtaattt cactacatct ggaattaagt ataactcaag aggctggaaa ttttgttgtg    2880
aggattttc cccctcctga ctgaatcatt tgaggcagag aaaactaccg agaccctgac     2940
attttgacca tcgagaatct acctaaaatc ctagccaaag ctctggtggc agcctctata    3000
aaggacctgt aagaagggaa gggagaggaa acaatggaa ttttactttta actaaaatat    3060
atattaaaag cagatcatcc aggtgcaaag caagcaaaaa cctgattgag atgtggaagg    3120
ttccttgtaa tttcacagcc acaacattaa cacacgactc tgtctggtta acgtgaacta    3180
gcctggtggg gagctaggca tctttgaact ctaatgtcac tgtacacagc caaagtaaa    3240
tagagggaga tttgtgcatt ttttcccttt tagaacagaa agtcgagtca gtaagcaggg    3300
tagatttgga agaagtataa gttgagatca atatgagcaa aagaagttgt aatagaatcc    3360
tccaaagatc taaaaagata tttatgttga tatttgctgg aatcagaatt aagggtgcca    3420
tcatttgtta agctattaaa accaaaggat aagcatattg ctcaatatgt agttatagtt    3480
attgttgcaa aattactaat ttttttctttt agaaagctc tcatgctggg cgtggtggca    3540
caagcccttta atcccagcac gtgggaggca gaggtaggca gatttctgag tatgaggcca    3600
gcctggtcta caaagtgagt tccaggacag cctatacaga gaaaccctgt ctcgaaaaac    3660
aaacaaacaa aaaaaaaaaa aaaaaaaga aaaaaagaa aagctctcat tgcatattct    3720
aggcaggcct tgaactaaaa aaatcctcct agttcagcat tctaattcct tggattctgg    3780
gtaaaggttt gttaccacac ccagctaaac agtgatttgg gacatccctt ggggagatt    3840
tgcttgtgga gaatggccaa ggtgttagtt caatctctca tccatttaga ataatcccac    3900
ttaaggaagc tcatctattg gaagcattag taaaagggag gaagtgggtg tggtttttag    3960
agactctaag tacatccctg gggcccacca ggttcattct tctccagacc agaggtagag    4020
tgtttctaac cttttgctcc agacactgct agatctatca cctcactctc tgaggatctg    4080
atctcagagc tgagcgagta tcgcattgct accaaccatt gctaagcagg gacgaggata    4140
attgcttggg taagtgcaca gtttacaaga gaaaatttct ttttttgttcc tattttaaat    4200
acaaacaggg gtttgcttag aagttgtatt ttgctatta gcaaaacctg attcagtttg    4260
tatttgcatt ttttttcttg ggatataatg tgggttaagg ttatagataa ttttaaattt    4320
attatgcaca tgttagttga tctgatgtat tataatgaga gatagtttca agatctcctc    4380
ctcctccttc tcttccttct tcattttca agacagggtc tctctgtgta gccctagttt    4440
tcctggaact ttctttgtag atcaggctgg ccttgaactc agaaatctcc tgcctctgcc    4500
tccctctgcc tccctctgtc tcccaagtgc tccgattaaa ggcgtagcca ccactgcctg    4560
gctcaagata cttttttttat attctgtgct ttgtctaaat tctaaaatat ttcaagaaca    4620
ttctatgctt aacaaatgct ctgagtggtt ttaagaaata tcagaattta aagcttgagg    4680
tagggtgcat tttcttggat aggaaggtgc tgtttcacta acgtgcctgc agtgaaaggc    4740
cagactggag gagaagggct tggatcactc ctcaatgaat gtctctggcc tcaaagaatg    4800
taccagtttg ggctgaagtc tccaggagga atgtagatgg taggatcacc tcaggcaata    4860
tgcctgtcag ggaaagttct tggtcataaa aaaaaaaaag cctatattgc cataatcaca    4920
agttgaatca aactttgtct agtttcttgt tcctctctgg cccaataata acactgcttt    4980
ttttccccctc agaaaa                                                   4996
```

-continued

```
<210> SEQ ID NO 32
<211> LENGTH: 1341
<212> TYPE: DNA
<213> ORGANISM: Mus musculus
<220> FEATURE:
<221> NAME/KEY: CDS
<222> LOCATION: (1)..(1341)

<400> SEQUENCE: 32 atg gaa tca gac aat tta caa gac cct cag gag gaa aca ctc acc tgc      48
Met Glu Ser Asp Asn Leu Gln Asp Pro Gln Glu Glu Thr Leu Thr Cys
1               5                   10                  15 tcc atc tgc cag agt atc ttt atg aat cca gtt tat tta agg tgt ggc      96
Ser Ile Cys Gln Ser Ile Phe Met Asn Pro Val Tyr Leu Arg Cys Gly
            20                  25                  30 cat aag ttc tgc gag gca tgt ctc tta ctt tct caa gaa gac atc aaa     144
His Lys Phe Cys Glu Ala Cys Leu Leu Leu Ser Gln Glu Asp Ile Lys
        35                  40                  45 ttt cct gcc tac tgc ccc atg tgt atg caa cca ttt aac cag gaa tat     192
Phe Pro Ala Tyr Cys Pro Met Cys Met Gln Pro Phe Asn Gln Glu Tyr
    50                  55                  60 ata aat gac att tct ctg aag aag cag gtg tcc att gtc aga aag aaa     240
Ile Asn Asp Ile Ser Leu Lys Lys Gln Val Ser Ile Val Arg Lys Lys
65                  70                  75                  80 agg ctc atg aaa tat ttg aat tct aag gag cac aag tgt gtg acc cac     288
Arg Leu Met Lys Tyr Leu Asn Ser Lys Glu His Lys Cys Val Thr His
                85                  90                  95 aag gca aaa aag atg atc ttc tgt gat aag agc aag atc ctc ctc tgt     336
Lys Ala Lys Lys Met Ile Phe Cys Asp Lys Ser Lys Ile Leu Leu Cys
            100                 105                 110 cac ctg tgt tct gac tcc cag gag cac agt ggt cac aca cac tgt tcc     384
His Leu Cys Ser Asp Ser Gln Glu His Ser Gly His Thr His Cys Ser
        115                 120                 125 att gat gta gct gtt cag gag aaa atg gag gaa ctt cta aag cac atg     432
Ile Asp Val Ala Val Gln Glu Lys Met Glu Glu Leu Leu Lys His Met
    130                 135                 140 gac tca tta tgg cgg agg ctc aaa atc cag cag aat tat gta gaa ata     480
Asp Ser Leu Trp Arg Arg Leu Lys Ile Gln Gln Asn Tyr Val Glu Ile
145                 150                 155                 160 gag agg aga acg acc ttg tgg tgg ttg aag tcc gtg aag cta cgg gag     528
Glu Arg Arg Thr Thr Leu Trp Trp Leu Lys Ser Val Lys Leu Arg Glu
                165                 170                 175 gaa gtg atc aag aga gtg twt gga aaa caa tgt cca ccc ctc tgt gaa     576
Glu Val Ile Lys Arg Val Xaa Gly Lys Gln Cys Pro Pro Leu Cys Glu
            180                 185                 190 gaa agg gat caa cac ata gag tgt ttg aga cat caa agc aac act act     624
Glu Arg Asp Gln His Ile Glu Cys Leu Arg His Gln Ser Asn Thr Thr
        195                 200                 205 tta gag gag ctc agg aaa agt gaa gct acg ata gtc cac gag aga aat     672
Leu Glu Glu Leu Arg Lys Ser Glu Ala Thr Ile Val His Glu Arg Asn
    210                 215                 220 caa cta ata gag gtt tat cgg gag ctg atg aca atg tcc cag agg cca     720
Gln Leu Ile Glu Val Tyr Arg Glu Leu Met Thr Met Ser Gln Arg Pro
225                 230                 235                 240 tac cag gag ctg ctg gtg cag gac ttg gat gac ttg ttc aga agg agt     768
Tyr Gln Glu Leu Leu Val Gln Asp Leu Asp Asp Leu Phe Arg Arg Ser
                245                 250                 255 aag cta gcg gca aag ctg gac atg cca cag ggt atg ata cca aga ctc     816
Lys Leu Ala Ala Lys Leu Asp Met Pro Gln Gly Met Ile Pro Arg Leu
            260                 265                 270 cat gcc cat tcc att cct ggg ctg act gca agg ctc aac tcc ttc cga     864
```

```
His Ala His Ser Ile Pro Gly Leu Thr Ala Arg Leu Asn Ser Phe Arg
            275                 280                 285 gtg aag att tcc ttt aaa cat tca atc atg ttc ggc tac acc tca gtc        912
Val Lys Ile Ser Phe Lys His Ser Ile Met Phe Gly Tyr Thr Ser Val
        290                 295                 300 aga cct ttt gat atc aga ctt ctc cat gaa agc aca tct ctg gat tca        960
Arg Pro Phe Asp Ile Arg Leu Leu His Glu Ser Thr Ser Leu Asp Ser
305                 310                 315                 320 gct gaa acc cat cgt gtt tcc tgg gga aaa aag agc ttc tcc agg gga       1008
Ala Glu Thr His Arg Val Ser Trp Gly Lys Lys Ser Phe Ser Arg Gly
            325                 330                 335 aaa tac tac tgg gag gtg gat ttg aag gac cat gag cag tgg act gta       1056
Lys Tyr Tyr Trp Glu Val Asp Leu Lys Asp His Glu Gln Trp Thr Val
            340                 345                 350 gga gtc cgt aag gat ccc tgg tta agg ggg aga agc tat gcg gcg aca       1104
Gly Val Arg Lys Asp Pro Trp Leu Arg Gly Arg Ser Tyr Ala Ala Thr
            355                 360                 365 ccc aca gat cta ttt ctt ctt gag tgt ttg aga aag gaa gat cat tac       1152
Pro Thr Asp Leu Phe Leu Leu Glu Cys Leu Arg Lys Glu Asp His Tyr
370                 375                 380 att ctc atc acc cgc ata gga ggt gaa cac tat ata gag aag cca gtt       1200
Ile Leu Ile Thr Arg Ile Gly Gly Glu His Tyr Ile Glu Lys Pro Val
385                 390                 395                 400 ggc caa gtt ggc gtg ttc ctt gat tgt gag ggt gga tat gta agt ttc       1248
Gly Gln Val Gly Val Phe Leu Asp Cys Glu Gly Gly Tyr Val Ser Phe
            405                 410                 415 gtg gat gta gcc aag agt tcc ctc ata ctc agc tac tct cct gga act       1296
Val Asp Val Ala Lys Ser Ser Leu Ile Leu Ser Tyr Ser Pro Gly Thr
            420                 425                 430 ttc cat tgt gct gtc agg cct ttc ttc tct gct gtc tac aca taa           1341
Phe His Cys Ala Val Arg Pro Phe Phe Ser Ala Val Tyr Thr
            435                 440                 445

<210> SEQ ID NO 33
<211> LENGTH: 446
<212> TYPE: PRT
<213> ORGANISM: Mus musculus
<220> FEATURE:
<221> NAME/KEY: misc_feature
<222> LOCATION: (183)..(183)
<223> OTHER INFORMATION: The 'Xaa' at location 183 stands for Tyr, or
      Phe.

<400> SEQUENCE: 33

Met Glu Ser Asp Asn Leu Gln Asp Pro Gln Glu Glu Thr Leu Thr Cys
1               5                   10                  15

Ser Ile Cys Gln Ser Ile Phe Met Asn Pro Val Tyr Leu Arg Cys Gly
            20                  25                  30

His Lys Phe Cys Glu Ala Cys Leu Leu Leu Ser Gln Glu Asp Ile Lys
        35                  40                  45

Phe Pro Ala Tyr Cys Pro Met Cys Met Gln Pro Phe Asn Gln Glu Tyr
    50                  55                  60

Ile Asn Asp Ile Ser Leu Lys Lys Gln Val Ser Ile Val Arg Lys Lys
65                  70                  75                  80

Arg Leu Met Lys Tyr Leu Asn Ser Lys Glu His Lys Cys Val Thr His
                85                  90                  95

Lys Ala Lys Lys Met Ile Phe Cys Asp Lys Ser Lys Ile Leu Leu Cys
            100                 105                 110

His Leu Cys Ser Asp Ser Gln Glu His Ser Gly His Thr His Cys Ser
        115                 120                 125
```

```
Ile Asp Val Ala Val Gln Glu Lys Met Glu Glu Leu Leu Lys His Met
130                 135                 140
Asp Ser Leu Trp Arg Arg Leu Lys Ile Gln Gln Asn Tyr Val Glu Ile
145                 150                 155                 160
Glu Arg Arg Thr Thr Leu Trp Trp Leu Lys Ser Val Lys Leu Arg Glu
                165                 170                 175
Glu Val Ile Lys Arg Val Xaa Gly Lys Gln Cys Pro Pro Leu Cys Glu
            180                 185                 190
Glu Arg Asp Gln His Ile Glu Cys Leu Arg His Gln Ser Asn Thr Thr
        195                 200                 205
Leu Glu Glu Leu Arg Lys Ser Glu Ala Thr Ile Val His Glu Arg Asn
210                 215                 220
Gln Leu Ile Glu Val Tyr Arg Glu Leu Met Thr Met Ser Gln Arg Pro
225                 230                 235                 240
Tyr Gln Glu Leu Leu Val Gln Asp Leu Asp Asp Leu Phe Arg Arg Ser
                245                 250                 255
Lys Leu Ala Ala Lys Leu Asp Met Pro Gln Gly Met Ile Pro Arg Leu
            260                 265                 270
His Ala His Ser Ile Pro Gly Leu Thr Ala Arg Leu Asn Ser Phe Arg
        275                 280                 285
Val Lys Ile Ser Phe Lys His Ser Ile Met Phe Gly Tyr Thr Ser Val
290                 295                 300
Arg Pro Phe Asp Ile Arg Leu Leu His Glu Ser Thr Ser Leu Asp Ser
305                 310                 315                 320
Ala Glu Thr His Arg Val Ser Trp Gly Lys Lys Ser Phe Ser Arg Gly
                325                 330                 335
Lys Tyr Tyr Trp Glu Val Asp Leu Lys Asp His Glu Gln Trp Thr Val
            340                 345                 350
Gly Val Arg Lys Asp Pro Trp Leu Arg Gly Arg Ser Tyr Ala Ala Thr
        355                 360                 365
Pro Thr Asp Leu Phe Leu Leu Glu Cys Leu Arg Lys Glu Asp His Tyr
370                 375                 380
Ile Leu Ile Thr Arg Ile Gly Gly Glu His Tyr Ile Glu Lys Pro Val
385                 390                 395                 400
Gly Gln Val Gly Val Phe Leu Asp Cys Glu Gly Gly Tyr Val Ser Phe
                405                 410                 415
Val Asp Val Ala Lys Ser Ser Leu Ile Leu Ser Tyr Ser Pro Gly Thr
            420                 425                 430
Phe His Cys Ala Val Arg Pro Phe Phe Ser Ala Val Tyr Thr
        435                 440                 445

<210> SEQ ID NO 34
<211> LENGTH: 886
<212> TYPE: DNA
<213> ORGANISM: Mus musculus
<220> FEATURE:
<221> NAME/KEY: CDS
<222> LOCATION: (189)..(680)

<400> SEQUENCE: 34
gcaagtctat cagtttgagg gtactagagc aagctggtct gtgattccat cttctactga    60
taaccaattg agacatccag cctcagtgag tgagaacttc tggattcttg gacttttctt   120
caaattcagc tggtgtggaa taagctcgac tgcaacctaa agtcaggac tttggtgaag    180 ccaaggca atg aag cgg ttc tgt ccc tgt ctt gtc caa gat aca tca cat   230
         Met Lys Arg Phe Cys Pro Cys Leu Val Gln Asp Thr Ser His
         1               5                  10
```

| | | |
|---|---|---|
| tcc gaa gag cat gca ctg cag act tca caa gaa ttg cca gcc ctg aga<br>Ser Glu Glu His Ala Leu Gln Thr Ser Gln Glu Leu Pro Ala Leu Arg<br>15                  20                 25                 30 | | 278 |
| cca cga tat tcc agg tct gag cca cag tgt ttc tgt gga gag cca aac<br>Pro Arg Tyr Ser Arg Ser Glu Pro Gln Cys Phe Cys Gly Glu Pro Asn<br>                 35                 40                 45 | | 326 |
| cac tgc cat gag gat gac tgg att gtt gat tgg gaa cca tac tac ctt<br>His Cys His Glu Asp Asp Trp Ile Val Asp Trp Glu Pro Tyr Tyr Leu<br>                 50                 55                 60 | | 374 |
| ccc tgt gta ctt gaa agc tgg gac tgc ttg aga tac cac tcc gga ttg<br>Pro Cys Val Leu Glu Ser Trp Asp Cys Leu Arg Tyr His Ser Gly Leu<br>        65                 70                 75 | | 422 |
| aat tgt gcc atg aag aag ggc aca gag gtc ttc cag att gag agt cag<br>Asn Cys Ala Met Lys Lys Gly Thr Glu Val Phe Gln Ile Glu Ser Gln<br>80                             85                 90 | | 470 |
| agg ggg cca caa gtg ttc cca gga gat atg gac aat gac aaa gat aca<br>Arg Gly Pro Gln Val Phe Pro Gly Asp Met Asp Asn Asp Lys Asp Thr<br>95                        100               105               110 | | 518 |
| gag gag cca gac caa ccc ttg cca agc ttg ctc agg gag aaa ggg ctg<br>Glu Glu Pro Asp Gln Pro Leu Pro Ser Leu Leu Arg Glu Lys Gly Leu<br>                      115                     120               125 | | 566 |
| gaa ctt gag acc tgt gat ggt gga gac tgc cct gac cag gat ccc gct<br>Glu Leu Glu Thr Cys Asp Gly Gly Asp Cys Pro Asp Gln Asp Pro Ala<br>                130                   135               140 | | 614 |
| tct gac agt ccc aag cac cta ggc tgc tgc tta tgg ctt caa agg gct<br>Ser Asp Ser Pro Lys His Leu Gly Cys Cys Leu Trp Leu Gln Arg Ala<br>                145                   150               155 | | 662 |
| ttt ggc cag aag aag tga gaaagccacc cagaactctg tgtggagccc<br>Phe Gly Gln Lys Lys<br>     160 | | 710 |
| aggagccctg atgcctgcta agacttgcaa tgagggatc ctcggtcagc tcctgctatt | | 770 |
| acagagagac acacccctgc ctctctcaca tccaaaggca attgtgtctt cagccatctg | | 830 |
| gatgttgttt gtttgtttgt tgttacagc tttcttaata aaagtgttaa aaagct | | 886 |

<210> SEQ ID NO 35
<211> LENGTH: 163
<212> TYPE: PRT
<213> ORGANISM: Mus musculus

<400> SEQUENCE: 35

Met Lys Arg Phe Cys Pro Cys Leu Val Gln Asp Thr Ser His Ser Glu
1                 5                     10                   15

Glu His Ala Leu Gln Thr Ser Gln Glu Leu Pro Ala Leu Arg Pro Arg
                 20                 25                 30

Tyr Ser Arg Ser Glu Pro Gln Cys Phe Cys Gly Glu Pro Asn His Cys
                     35                 40                 45

His Glu Asp Asp Trp Ile Val Asp Trp Glu Pro Tyr Tyr Leu Pro Cys
       50                 55                 60

Val Leu Glu Ser Trp Asp Cys Leu Arg Tyr His Ser Gly Leu Asn Cys
65                   70                 75                 80

Ala Met Lys Lys Gly Thr Glu Val Phe Gln Ile Glu Ser Gln Arg Gly
                 85                 90                 95

Pro Gln Val Phe Pro Gly Asp Met Asp Asn Asp Lys Asp Thr Glu Glu
                 100               105               110

Pro Asp Gln Pro Leu Pro Ser Leu Leu Arg Glu Lys Gly Leu Glu Leu
               115               120               125

Glu Thr Cys Asp Gly Gly Asp Cys Pro Asp Gln Asp Pro Ala Ser Asp

```
            130                 135                 140
Ser Pro Lys His Leu Gly Cys Cys Leu Trp Leu Gln Arg Ala Phe Gly
145                 150                 155                 160

Gln Lys Lys

<210> SEQ ID NO 36
<211> LENGTH: 1625
<212> TYPE: DNA
<213> ORGANISM: Mus musculus
<220> FEATURE:
<221> NAME/KEY: CDS
<222> LOCATION: (102)..(1547)

<400> SEQUENCE: 36
acactcagag acctgcagcc tgataactgc ctggtgcagc tgggacttgg agacctatct     60
gcagtgctca actggagcct tctgactgga gactgaagag g atg agt gtt cag act    116
                                             Met Ser Val Gln Thr
                                               1               5 ctg tcc act ctc cag aat ctg aca ttg aag gct ctg ctg aga gat gag     164
Leu Ser Thr Leu Gln Asn Leu Thr Leu Lys Ala Leu Leu Arg Asp Glu
         10                  15                  20 gct ttg gcc ttg tcc tgt ctg gag gag gtg cct ttt ctg ctc ttc cca     212
Ala Leu Ala Leu Ser Cys Leu Glu Glu Val Pro Phe Leu Leu Phe Pro
 25                  30                  35 gca ctg ttc cag agg gcc ttt gct ggc aga ctt aag aag ctc atg aag     260
Ala Leu Phe Gln Arg Ala Phe Ala Gly Arg Leu Lys Lys Leu Met Lys
     40                  45                  50 gca atc atg gca gcc tgg act ttt ccc tgt ctc cct gtg ggg gct ttg     308
Ala Ile Met Ala Ala Trp Thr Phe Pro Cys Leu Pro Val Gly Ala Leu
 55                  60                  65 atg aag tca cct aac ctg gag acc ttg cag gct gtg cta gat gga ata     356
Met Lys Ser Pro Asn Leu Glu Thr Leu Gln Ala Val Leu Asp Gly Ile
 70                  75                  80                  85 gac atg caa ctg aca aga gaa tct cac ccc agg gga aaa ctt cag gtt     404
Asp Met Gln Leu Thr Arg Glu Ser His Pro Arg Gly Lys Leu Gln Val
             90                  95                 100 ctg gac ctg agg aat gtg cac cat gcc ttc tgg gac ata tgg gct ggt     452
Leu Asp Leu Arg Asn Val His His Ala Phe Trp Asp Ile Trp Ala Gly
        105                 110                 115 gca gag gat ggt agc tgt tct tca gag ccc ttg gat gag aag cct aca     500
Ala Glu Asp Gly Ser Cys Ser Ser Glu Pro Leu Asp Glu Lys Pro Thr
    120                 125                 130 gta gtg aag gtc ctt cgc aga tat gca agg agg agg cag ctg aag gtg     548
Val Val Lys Val Leu Arg Arg Tyr Ala Arg Arg Arg Gln Leu Lys Val
135                 140                 145 gta gca gac ctg tgc ctc agg ccc cgc cat gat gaa aca caa gca tac     596
Val Ala Asp Leu Cys Leu Arg Pro Arg His Asp Glu Thr Gln Ala Tyr
150                 155                 160                 165 ttc ttg aag tgg gcc cag cag aga aag gac tcc cta cat ttg tgc tgt     644
Phe Leu Lys Trp Ala Gln Gln Arg Lys Asp Ser Leu His Leu Cys Cys
            170                 175                 180 ata aac atg aag atc tgg gct atg ccc gtg gac ttt gtc tta gag att     692
Ile Asn Met Lys Ile Trp Ala Met Pro Val Asp Phe Val Leu Glu Ile
        185                 190                 195 ttg aat gtc ttt cat cca gag cac atc gag gaa ttc gaa ctg aac act     740
Leu Asn Val Phe His Pro Glu His Ile Glu Glu Phe Glu Leu Asn Thr
    200                 205                 210 gag tgg aat gtg ttc aat ctg gcc cgt ttt gct ccc tgc tta tgg cag     788
Glu Trp Asn Val Phe Asn Leu Ala Arg Phe Ala Pro Cys Leu Trp Gln
215                 220                 225
```

```
atg aga aat ctt cgc aaa ctt ctc ctg gca ccc ctc tat aag aat gtc      836
Met Arg Asn Leu Arg Lys Leu Leu Leu Ala Pro Leu Tyr Lys Asn Val
230             235                 240                 245 ttc aag att gcc aat agg aca gga gac aga gaa gat aag tgt gtc aag      884
Phe Lys Ile Ala Asn Arg Thr Gly Asp Arg Glu Asp Lys Cys Val Lys
                250                 255                 260 gag ttc gtt tct atc ttc tcc aaa ttc aat tgt ctc cag cat ctc tcc      932
Glu Phe Val Ser Ile Phe Ser Lys Phe Asn Cys Leu Gln His Leu Ser
            265                 270                 275 atg caa ggt gtc cac ttt ctc aca gac cac atg agt cag gtc ttc agg      980
Met Gln Gly Val His Phe Leu Thr Asp His Met Ser Gln Val Phe Arg
        280                 285                 290 tgc ttg atg aca ccc ttg ggg tcc ctc tcc atc act cac tac caa att     1028
Cys Leu Met Thr Pro Leu Gly Ser Leu Ser Ile Thr His Tyr Gln Ile
    295                 300                 305 tca cag tca gac ttg gat tcc ttc tct tgc tgt cag agt ctc ttt cag     1076
Ser Gln Ser Asp Leu Asp Ser Phe Ser Cys Cys Gln Ser Leu Phe Gln
310                 315                 320                 325 cta aat cat ctg gag atg aaa ggc gtg gtc tta cag gtt ttg gat gtg     1124
Leu Asn His Leu Glu Met Lys Gly Val Val Leu Gln Val Leu Asp Val
                330                 335                 340 atg cct ctg aga ggt ctc tta gag aaa gtg gta aaa act ctt gag act     1172
Met Pro Leu Arg Gly Leu Leu Glu Lys Val Val Lys Thr Leu Glu Thr
            345                 350                 355 ctg aat ttg cag gga tgt aag ctg aag gac tct cag ctc aat gca ctc     1220
Leu Asn Leu Gln Gly Cys Lys Leu Lys Asp Ser Gln Leu Asn Ala Leu
        360                 365                 370 cta cct tcc ttc ata caa tgc tct cag ctc acc aag gtc aac ttt tac     1268
Leu Pro Ser Phe Ile Gln Cys Ser Gln Leu Thr Lys Val Asn Phe Tyr
    375                 380                 385 aac aat gac ttc tcc atg ccc atc ctg aag gac ctt tta cag cac aca     1316
Asn Asn Asp Phe Ser Met Pro Ile Leu Lys Asp Leu Leu Gln His Thr
390                 395                 400                 405 gcc aac tgg aac aag atg aat gtg gaa cag tac cct gcc tct ctg gag     1364
Ala Asn Trp Asn Lys Met Asn Val Glu Gln Tyr Pro Ala Ser Leu Glu
                410                 415                 420 tgc tat aat gag ttg gga cat gtc tct gta gaa aga ttt gcc caa ctt     1412
Cys Tyr Asn Glu Leu Gly His Val Ser Val Glu Arg Phe Ala Gln Leu
            425                 430                 435 tgt cag gaa ctc atg gat aca cta agg gca ata agg cag ccc aag agc     1460
Cys Gln Glu Leu Met Asp Thr Leu Arg Ala Ile Arg Gln Pro Lys Ser
        440                 445                 450 ctc tct ttt gct aca cgt ata tgc cac aaa tgt ggt gag tgc tgt gtc     1508
Leu Ser Phe Ala Thr Arg Ile Cys His Lys Cys Gly Glu Cys Cys Val
    455                 460                 465 tat ggc aag aga gcc aga ctt tgt ttt tgc tgg cgg tga acatggattc     1557
Tyr Gly Lys Arg Ala Arg Leu Cys Phe Cys Trp Arg
470                 475                 480 agaacttctg catgtgaata aatgacagtc ttgagacgca aaaaaaaaaa aaaaaaaaaa   1617
aaaaaaaa                                                           1625

<210> SEQ ID NO 37
<211> LENGTH: 481
<212> TYPE: PRT
<213> ORGANISM: Mus musculus

<400> SEQUENCE: 37

Met Ser Val Gln Thr Leu Ser Thr Leu Gln Asn Leu Thr Leu Lys Ala
1               5                   10                  15

Leu Leu Arg Asp Glu Ala Leu Ala Leu Ser Cys Leu Glu Glu Val Pro
```

```
                20              25              30
Phe Leu Leu Phe Pro Ala Leu Phe Gln Arg Ala Phe Ala Gly Arg Leu
            35              40              45
Lys Lys Leu Met Lys Ala Ile Met Ala Ala Trp Thr Phe Pro Cys Leu
50              55              60
Pro Val Gly Ala Leu Met Lys Ser Pro Asn Leu Glu Thr Leu Gln Ala
65              70              75              80
Val Leu Asp Gly Ile Asp Met Gln Leu Thr Arg Glu Ser His Pro Arg
                85              90              95
Gly Lys Leu Gln Val Leu Asp Leu Arg Asn Val His His Ala Phe Trp
            100             105             110
Asp Ile Trp Ala Gly Ala Glu Asp Gly Ser Cys Ser Ser Glu Pro Leu
            115             120             125
Asp Glu Lys Pro Thr Val Val Lys Val Leu Arg Arg Tyr Ala Arg Arg
            130             135             140
Arg Gln Leu Lys Val Val Ala Asp Leu Cys Leu Arg Pro Arg His Asp
145             150             155             160
Glu Thr Gln Ala Tyr Phe Leu Lys Trp Ala Gln Gln Arg Lys Asp Ser
                165             170             175
Leu His Leu Cys Cys Ile Asn Met Lys Ile Trp Ala Met Pro Val Asp
            180             185             190
Phe Val Leu Glu Ile Leu Asn Val Phe His Pro Glu His Ile Glu Glu
            195             200             205
Phe Glu Leu Asn Thr Glu Trp Asn Val Phe Asn Leu Ala Arg Phe Ala
            210             215             220
Pro Cys Leu Trp Gln Met Arg Asn Leu Arg Lys Leu Leu Leu Ala Pro
225             230             235             240
Leu Tyr Lys Asn Val Phe Lys Ile Ala Asn Arg Thr Gly Asp Arg Glu
                245             250             255
Asp Lys Cys Val Lys Glu Phe Val Ser Ile Phe Ser Lys Phe Asn Cys
            260             265             270
Leu Gln His Leu Ser Met Gln Gly Val His Phe Leu Thr Asp His Met
            275             280             285
Ser Gln Val Phe Arg Cys Leu Met Thr Pro Leu Gly Ser Leu Ser Ile
            290             295             300
Thr His Tyr Gln Ile Ser Gln Ser Asp Leu Asp Ser Phe Ser Cys Cys
305             310             315             320
Gln Ser Leu Phe Gln Leu Asn His Leu Glu Met Lys Gly Val Val Leu
                325             330             335
Gln Val Leu Asp Val Met Pro Leu Arg Gly Leu Leu Glu Lys Val Val
            340             345             350
Lys Thr Leu Glu Thr Leu Asn Leu Gln Gly Cys Lys Leu Lys Asp Ser
            355             360             365
Gln Leu Asn Ala Leu Leu Pro Ser Phe Ile Gln Cys Ser Gln Leu Thr
            370             375             380
Lys Val Asn Phe Tyr Asn Asn Asp Phe Ser Met Pro Ile Leu Lys Asp
385             390             395             400
Leu Leu Gln His Thr Ala Asn Trp Asn Lys Met Asn Val Glu Gln Tyr
                405             410             415
Pro Ala Ser Leu Glu Cys Tyr Asn Glu Leu Gly His Val Ser Val Glu
            420             425             430
Arg Phe Ala Gln Leu Cys Gln Glu Leu Met Asp Thr Leu Arg Ala Ile
            435             440             445
```

```
Arg Gln Pro Lys Ser Leu Ser Phe Ala Thr Arg Ile Cys His Lys Cys
    450                 455                 460

Gly Glu Cys Cys Val Tyr Gly Lys Arg Ala Arg Leu Cys Phe Cys Trp
465                 470                 475                 480

Arg

<210> SEQ ID NO 38
<211> LENGTH: 1325
<212> TYPE: DNA
<213> ORGANISM: Mus musculus
<220> FEATURE:
<221> NAME/KEY: CDS
<222> LOCATION: (120)..(1202)

<400> SEQUENCE: 38
acttgtagta gtccagggaa gtaagcagag ctccttgcac tgcagactct tgtgaacacc      60
gggacacatt agaccctagt ttcctcactg tgttcgggaa aggaagctca ggagacaaa     119 atg cag aga gaa gat aac cga gtc caa agt gtg aga aat gac aaa gaa     167
Met Gln Arg Glu Asp Asn Arg Val Gln Ser Val Arg Asn Asp Lys Glu
1               5                   10                  15 gcc aat agg agg agg agg ctg agg caa gaa ggc caa agt tcc tca ggt     215
Ala Asn Arg Arg Arg Arg Leu Arg Gln Glu Gly Gln Ser Ser Ser Gly
            20                  25                  30 ccg tgt gat agc ccg tgg act gag gat gaa atc tgg atc ttg ctg caa     263
Pro Cys Asp Ser Pro Trp Thr Glu Asp Glu Ile Trp Ile Leu Leu Gln
        35                  40                  45 gag tgg gca atg gtt gaa tat gaa ctc gga gac cca ggc aat aag atg     311
Glu Trp Ala Met Val Glu Tyr Glu Leu Gly Asp Pro Gly Asn Lys Met
    50                  55                  60 cat gcg aag gcc aag tcc ctt agc aga cgc ctc tct aat cgg ggt ctg     359
His Ala Lys Ala Lys Ser Leu Ser Arg Arg Leu Ser Asn Arg Gly Leu
65                  70                  75                  80 agg aag agc aag aat agc tgc ctt gat gtg atg gtg aag atg aag gac     407
Arg Lys Ser Lys Asn Ser Cys Leu Asp Val Met Val Lys Met Lys Asp
                85                  90                  95 ctg cac aca cgt ctt tgt aac gag agg ccc cgg gct tac cgc ttg tat     455
Leu His Thr Arg Leu Cys Asn Glu Arg Pro Arg Ala Tyr Arg Leu Tyr
            100                 105                 110 tcg act tat gaa tgg atc ctg tac gag atc ttg ggc cac ccc aga tcc     503
Ser Thr Tyr Glu Trp Ile Leu Tyr Glu Ile Leu Gly His Pro Arg Ser
        115                 120                 125 cag gga ggc tat gtg cca ggt cct tgg ttt gat ggg cac ggt aac cca     551
Gln Gly Gly Tyr Val Pro Gly Pro Trp Phe Asp Gly His Gly Asn Pro
    130                 135                 140 cca gct tcc tat gca act tcc ctc tgc att ggt ggt gcc atc tct cta     599
Pro Ala Ser Tyr Ala Thr Ser Leu Cys Ile Gly Gly Ala Ile Ser Leu
145                 150                 155                 160 ggc cct tcc ttt agc cca tgg acc gac cct gaa atc aag atc ttc ctg     647
Gly Pro Ser Phe Ser Pro Trp Thr Asp Pro Glu Ile Lys Ile Phe Leu
                165                 170                 175 cag gag tgg caa gtg gtt gaa cgg gaa ttt ggc cac cca ggc cag aag     695
Gln Glu Trp Gln Val Val Glu Arg Glu Phe Gly His Pro Gly Gln Lys
            180                 185                 190 atc aag cag aag agc agt ctt gtt tgc cag cgt ctc tat cat cga ggc     743
Ile Lys Gln Lys Ser Ser Leu Val Cys Gln Arg Leu Tyr His Arg Gly
        195                 200                 205 ctg ttc aag gac atc caa agc tgt ttg gac ctg atg tgg acc atg aag     791
Leu Phe Lys Asp Ile Gln Ser Cys Leu Asp Leu Met Trp Thr Met Lys
    210                 215                 220 gat ctg cac tcc act ctc agt aga gag aga tca agg act gta ccc ttg     839
```

```
Asp Leu His Ser Thr Leu Ser Arg Glu Arg Ser Arg Thr Val Pro Leu
225                 230                 235                 240 ttt tct cct tat aga gat tat ctg gaa agg atc ttc gac ccc aaa tgt       887
Phe Ser Pro Tyr Arg Asp Tyr Leu Glu Arg Ile Phe Asp Pro Lys Cys
                    245                 250                 255 cag aga ggc cat gtt cca ggt gtt cag tat aat tgg tct ggt tac cac       935
Gln Arg Gly His Val Pro Gly Val Gln Tyr Asn Trp Ser Gly Tyr His
                260                 265                 270 agg cct tcc tca aac cct caa act cca atg gtg atg cca tct cct gta       983
Arg Pro Ser Ser Asn Pro Gln Thr Pro Met Val Met Pro Ser Pro Val
            275                 280                 285 tac cag cct tgg gat tat ggc atg gct gca tct tct ggt cag ctt ccc      1031
Tyr Gln Pro Trp Asp Tyr Gly Met Ala Ala Ser Ser Gly Gln Leu Pro
        290                 295                 300 tgg atc cca tta cta atc atg tcc agt cag gac tta ctg gtt ccc aga      1079
Trp Ile Pro Leu Leu Ile Met Ser Ser Gln Asp Leu Leu Val Pro Arg
305                 310                 315                 320 tgg gat gcc tgg aat gcc acc tat cca ttg cca gtt caa cat gta ttt      1127
Trp Asp Ala Trp Asn Ala Thr Tyr Pro Leu Pro Val Gln His Val Phe
                325                 330                 335 cag gcc tct ctc cct gga gac aac aac ttt cag cag ctg tgg tca cct      1175
Gln Ala Ser Leu Pro Gly Asp Asn Asn Phe Gln Gln Leu Trp Ser Pro
                340                 345                 350 cgt gat gag agc tca agt cct cag tga agacatgtgg ggacttttct            1222
Arg Asp Glu Ser Ser Ser Pro Gln
            355                 360 ttttcctctg aaaaccacta agaatcttcc agcactgtat ggatcctcaa tgtctctatt    1282
ttattgtaaa ggaaatgtga aatcaaataa attatttttga cac                     1325

<210> SEQ ID NO 39
<211> LENGTH: 360
<212> TYPE: PRT
<213> ORGANISM: Mus musculus

<400> SEQUENCE: 39

Met Gln Arg Glu Asp Asn Arg Val Gln Ser Val Arg Asn Asp Lys Glu
1               5                   10                  15

Ala Asn Arg Arg Arg Leu Arg Gln Glu Gly Gln Ser Ser Ser Gly
            20                  25                  30

Pro Cys Asp Ser Pro Trp Thr Glu Asp Glu Ile Trp Ile Leu Leu Gln
        35                  40                  45

Glu Trp Ala Met Val Glu Tyr Glu Leu Gly Asp Pro Gly Asn Lys Met
50                  55                  60

His Ala Lys Ala Lys Ser Leu Ser Arg Arg Leu Ser Asn Arg Gly Leu
65                  70                  75                  80

Arg Lys Ser Lys Asn Ser Cys Leu Asp Val Met Val Lys Met Lys Asp
                85                  90                  95

Leu His Thr Arg Leu Cys Asn Glu Arg Pro Arg Ala Tyr Arg Leu Tyr
            100                 105                 110

Ser Thr Tyr Glu Trp Ile Leu Tyr Glu Ile Leu Gly His Pro Arg Ser
        115                 120                 125

Gln Gly Gly Tyr Val Pro Gly Pro Trp Phe Asp Gly His Gly Asn Pro
    130                 135                 140

Pro Ala Ser Tyr Ala Thr Ser Leu Cys Ile Gly Gly Ala Ile Ser Leu
145                 150                 155                 160

Gly Pro Ser Phe Ser Pro Trp Thr Asp Pro Glu Ile Lys Ile Phe Leu
                165                 170                 175
```

```
Gln Glu Trp Gln Val Val Glu Arg Glu Phe Gly His Pro Gly Gln Lys
            180                 185                 190
Ile Lys Gln Lys Ser Ser Leu Val Cys Gln Arg Leu Tyr His Arg Gly
        195                 200                 205
Leu Phe Lys Asp Ile Gln Ser Cys Leu Asp Leu Met Trp Thr Met Lys
    210                 215                 220
Asp Leu His Ser Thr Leu Ser Arg Glu Arg Ser Arg Thr Val Pro Leu
225                 230                 235                 240
Phe Ser Pro Tyr Arg Asp Tyr Leu Glu Arg Ile Phe Asp Pro Lys Cys
                245                 250                 255
Gln Arg Gly His Val Pro Gly Val Gln Tyr Asn Trp Ser Gly Tyr His
            260                 265                 270
Arg Pro Ser Ser Asn Pro Gln Thr Pro Met Val Met Pro Ser Pro Val
        275                 280                 285
Tyr Gln Pro Trp Asp Tyr Gly Met Ala Ala Ser Ser Gly Gln Leu Pro
    290                 295                 300
Trp Ile Pro Leu Leu Ile Met Ser Ser Gln Asp Leu Leu Val Pro Arg
305                 310                 315                 320
Trp Asp Ala Trp Asn Ala Thr Tyr Pro Leu Pro Val Gln His Val Phe
                325                 330                 335
Gln Ala Ser Leu Pro Gly Asp Asn Asn Phe Gln Gln Leu Trp Ser Pro
            340                 345                 350
Arg Asp Glu Ser Ser Ser Pro Gln
        355                 360

<210> SEQ ID NO 40
<211> LENGTH: 1415
<212> TYPE: DNA
<213> ORGANISM: Mus musculus
<220> FEATURE:
<221> NAME/KEY: CDS
<222> LOCATION: (81)..(1145)

<400> SEQUENCE: 40
agctgtggga ggctgcactc actcgaggtc ctgagttgca ccgagccggt tctcctaggg     60
taatcccctc cctgccaatc atg ttc ctg agg agc agc gcc tcc cgt ctc ctc    113
                      Met Phe Leu Arg Ser Ser Ala Ser Arg Leu Leu
                        1               5                  10 cac ggg caa att cct tgc gtc ctg acg aga tcc gtc cac tct gta gct     161
His Gly Gln Ile Pro Cys Val Leu Thr Arg Ser Val His Ser Val Ala
                15                  20                  25 ata gtc gga gcc cct ttc tct cgg gga cag aag aag cta gga gtg gaa     209
Ile Val Gly Ala Pro Phe Ser Arg Gly Gln Lys Lys Leu Gly Val Glu
            30                  35                  40 tat ggt cca gct gcc att cga gaa gct ggc ttg ctg aag agg ctc tcc     257
Tyr Gly Pro Ala Ala Ile Arg Glu Ala Gly Leu Leu Lys Arg Leu Ser
        45                  50                  55 agg ttg gga tgc cac cta aaa gac ttt gga gac ttg agt ttt act aat     305
Arg Leu Gly Cys His Leu Lys Asp Phe Gly Asp Leu Ser Phe Thr Asn
60                  65                  70                  75 gtc cca caa gat gat ccc tac aat aat ctg gtt gtg tat cct cgt tca     353
Val Pro Gln Asp Asp Pro Tyr Asn Asn Leu Val Val Tyr Pro Arg Ser
                80                  85                  90 gtg ggc ctt gcc aac cag gaa ctg gct gaa gtg gtt agt aga gct gtg     401
Val Gly Leu Ala Asn Gln Glu Leu Ala Glu Val Val Ser Arg Ala Val
            95                 100                 105 tca ggt ggc tac agc tgt gtc acc atg gga gga gac cac agc ctg gca     449
Ser Gly Gly Tyr Ser Cys Val Thr Met Gly Gly Asp His Ser Leu Ala
        110                 115                 120
```

```
ata ggt acc att atc ggt cac gcc cgg cac cgc cca gat ctc tgt gtc      497
Ile Gly Thr Ile Ile Gly His Ala Arg His Arg Pro Asp Leu Cys Val
    125                 130                 135 atc tgg gtt gat gct cat gcg gac att aat aca cct ctc acc act gta      545
Ile Trp Val Asp Ala His Ala Asp Ile Asn Thr Pro Leu Thr Thr Val
140                 145                 150                 155 tct gga aat ata cat gga cag cca ctt tcc ttt ctc atc aaa gaa cta      593
Ser Gly Asn Ile His Gly Gln Pro Leu Ser Phe Leu Ile Lys Glu Leu
                160                 165                 170 caa gac aag gta cca caa ctg cca gga ttt tcc tgg atc aaa cct tgc      641
Gln Asp Lys Val Pro Gln Leu Pro Gly Phe Ser Trp Ile Lys Pro Cys
            175                 180                 185 ctc tct ccc cca aat att gtg tac att ggc ctg aga gat gtg gag cct      689
Leu Ser Pro Pro Asn Ile Val Tyr Ile Gly Leu Arg Asp Val Glu Pro
        190                 195                 200 cct gaa cat ttt att tta aag aat tat gac atc cag tat ttt tcc atg      737
Pro Glu His Phe Ile Leu Lys Asn Tyr Asp Ile Gln Tyr Phe Ser Met
    205                 210                 215 aga gag att gat cga ctt ggg atc cag aag gtg atg gaa cag aca ttt      785
Arg Glu Ile Asp Arg Leu Gly Ile Gln Lys Val Met Glu Gln Thr Phe
220                 225                 230                 235 gat cgg ctg att ggc aaa agg cag agg cca atc cac ctg agt ttt gac      833
Asp Arg Leu Ile Gly Lys Arg Gln Arg Pro Ile His Leu Ser Phe Asp
                240                 245                 250 att gat gca ttt gac cct aaa ctg gct cca gcc aca gga acc cct gtt      881
Ile Asp Ala Phe Asp Pro Lys Leu Ala Pro Ala Thr Gly Thr Pro Val
            255                 260                 265 gta ggg gga tta acc tac aga gaa gga gtg tat att act gaa gaa ata      929
Val Gly Gly Leu Thr Tyr Arg Glu Gly Val Tyr Ile Thr Glu Glu Ile
        270                 275                 280 cat aat aca ggg ttg ctg tca gct ctg gat ctt gtt gaa gtc aat cct      977
His Asn Thr Gly Leu Leu Ser Ala Leu Asp Leu Val Glu Val Asn Pro
    285                 290                 295 cat ttg gcc act tct gag gaa gag gcc aag gca aca gcc aga cta gca     1025
His Leu Ala Thr Ser Glu Glu Glu Ala Lys Ala Thr Ala Arg Leu Ala
300                 305                 310                 315 gtg gat gtg att gct tca agt ttt ggt cag aca aga gaa gga gga cac     1073
Val Asp Val Ile Ala Ser Ser Phe Gly Gln Thr Arg Glu Gly Gly His
                320                 325                 330 att gtc tat gac cac ctt cct act cct agt tca cca cac gaa tca gaa     1121
Ile Val Tyr Asp His Leu Pro Thr Pro Ser Ser Pro His Glu Ser Glu
            335                 340                 345 aat gaa gaa tgt gtg aga att tag gaaatactgt actctggcac ctttcacaac    1175
Asn Glu Glu Cys Val Arg Ile
        350 agcattacag agttgcaagg cattcgaagg gacagatatg aaatggctgt ctggatcaat   1235 attgccttaa tgagaacatc tgtgcactct cacaactgta aaactcccct ctctattttg   1295 gtcaccaaca ctattactgt aaatgtattt tttgttgttt ttgaagttta caagctatta   1355 atgttataca tgtaagtttg aaggagtcat aaacaacatt tattacctta gtatatcata   1415

<210> SEQ ID NO 41
<211> LENGTH: 354
<212> TYPE: PRT
<213> ORGANISM: Mus musculus

<400> SEQUENCE: 41

Met Phe Leu Arg Ser Ser Ala Ser Arg Leu Leu His Gly Gln Ile Pro
1               5                   10                  15
```

```
Cys Val Leu Thr Arg Ser Val His Ser Val Ala Ile Val Gly Ala Pro
            20                  25                  30

Phe Ser Arg Gly Gln Lys Lys Leu Gly Val Glu Tyr Gly Pro Ala Ala
        35                  40                  45

Ile Arg Glu Ala Gly Leu Leu Lys Arg Leu Ser Arg Leu Gly Cys His
 50                  55                  60

Leu Lys Asp Phe Gly Asp Leu Ser Phe Thr Asn Val Pro Gln Asp Asp
 65                  70                  75                  80

Pro Tyr Asn Asn Leu Val Val Tyr Pro Arg Ser Val Gly Leu Ala Asn
                85                  90                  95

Gln Glu Leu Ala Glu Val Val Ser Arg Ala Val Ser Gly Gly Tyr Ser
            100                 105                 110

Cys Val Thr Met Gly Gly Asp His Ser Leu Ala Ile Gly Thr Ile Ile
        115                 120                 125

Gly His Ala Arg His Arg Pro Asp Leu Cys Val Ile Trp Val Asp Ala
130                 135                 140

His Ala Asp Ile Asn Thr Pro Leu Thr Thr Val Ser Gly Asn Ile His
145                 150                 155                 160

Gly Gln Pro Leu Ser Phe Leu Ile Lys Glu Leu Gln Asp Lys Val Pro
                165                 170                 175

Gln Leu Pro Gly Phe Ser Trp Ile Lys Pro Cys Leu Ser Pro Pro Asn
            180                 185                 190

Ile Val Tyr Ile Gly Leu Arg Asp Val Glu Pro Pro Glu His Phe Ile
        195                 200                 205

Leu Lys Asn Tyr Asp Ile Gln Tyr Phe Ser Met Arg Glu Ile Asp Arg
210                 215                 220

Leu Gly Ile Gln Lys Val Met Glu Gln Thr Phe Asp Arg Leu Ile Gly
225                 230                 235                 240

Lys Arg Gln Arg Pro Ile His Leu Ser Phe Asp Ile Asp Ala Phe Asp
                245                 250                 255

Pro Lys Leu Ala Pro Ala Thr Gly Thr Pro Val Val Gly Gly Leu Thr
            260                 265                 270

Tyr Arg Glu Gly Val Tyr Ile Thr Glu Glu Ile His Asn Thr Gly Leu
        275                 280                 285

Leu Ser Ala Leu Asp Leu Val Glu Val Asn Pro His Leu Ala Thr Ser
290                 295                 300

Glu Glu Glu Ala Lys Ala Thr Ala Arg Leu Ala Val Asp Val Ile Ala
305                 310                 315                 320

Ser Ser Phe Gly Gln Thr Arg Glu Gly Gly His Ile Val Tyr Asp His
                325                 330                 335

Leu Pro Thr Pro Ser Ser Pro His Glu Ser Glu Asn Glu Glu Cys Val
            340                 345                 350

Arg Ile

<210> SEQ ID NO 42
<211> LENGTH: 858
<212> TYPE: DNA
<213> ORGANISM: Mus musculus
<220> FEATURE:
<221> NAME/KEY: CDS
<222> LOCATION: (151)..(666)

<400> SEQUENCE: 42
gcctgtgatt ccgtcttcta ctgaagacca cctgaaccat ccatcctcag gaactgagaa    60
cttctggaat cttggacttt acttcctctc cagctgttgt ggaataagta caactgcagc   120
```

```
ctgaggtgga ggatttacct tcagggatcc atg gat aaa gcc aag aag atg atg         174
                                    Met Asp Lys Ala Lys Lys Met Met
                                    1               5 cag tcc att ccc agt ttt gtc aag gat aca tca gat att gaa gaa cat         222
Gln Ser Ile Pro Ser Phe Val Lys Asp Thr Ser Asp Ile Glu Glu His
    10              15                  20 gca ctg ccc agt gca cag gtc ttg cca gcc cag agt aca agg tgt tct         270
Ala Leu Pro Ser Ala Gln Val Leu Pro Ala Gln Ser Thr Arg Cys Ser
25              30                  35                  40 aat tct gag gca ctt tgt tta ggc aaa gat caa agc cac tgc tct gag         318
Asn Ser Glu Ala Leu Cys Leu Gly Lys Asp Gln Ser His Cys Ser Glu
                45                  50                  55 gat ggc tgg att gcc gaa tgg gat cta tac tcc ttt tgt gta ttt gag         366
Asp Gly Trp Ile Ala Glu Trp Asp Leu Tyr Ser Phe Cys Val Phe Glu
            60                  65                  70 agt gtg gac tac ctg aga tcc tac cga aga ttg aat tct gcc atg aag         414
Ser Val Asp Tyr Leu Arg Ser Tyr Arg Arg Leu Asn Ser Ala Met Lys
            75                  80                  85 aag ggc aca gag gtc ttc cag agt gag agt cag agg aag cca aaa gtg         462
Lys Gly Thr Glu Val Phe Gln Ser Glu Ser Gln Arg Lys Pro Lys Val
90              95                  100 tcc cca gga gat gtg gaa aac tac aaa gac aaa gat aca gag aag cca         510
Ser Pro Gly Asp Val Glu Asn Tyr Lys Asp Lys Asp Thr Glu Lys Pro
105             110                 115                 120 gac caa ccc tcc cca agc ttg ctc agg gag aaa ggt ctg gat ctt gtg         558
Asp Gln Pro Ser Pro Ser Leu Leu Arg Glu Lys Gly Leu Asp Leu Val
                125                 130                 135 acc tgt gac ggt gga gac tgc cct gtc cgg gat cct gtt tct gac agt         606
Thr Cys Asp Gly Gly Asp Cys Pro Val Arg Asp Pro Val Ser Asp Ser
            140                 145                 150 tcc agg cac cta ggc tgc tgg gca tgg ttt caa agg gct ttt ggc cat         654
Ser Arg His Leu Gly Cys Trp Ala Trp Phe Gln Arg Ala Phe Gly His
            155                 160                 165 aag aag aag tga gaaaggcact aagaactgtg tttggagccc atgaaccctg             706
Lys Lys Lys
        170 atgcctgcta agacttgcaa ttaggggacc ttctgtcagc ttctgctgtt agagcaaagg       766 cacacaaagg cagttgtgtc tttgcagcca tctggtttgt gtttgtttgt ttatttgttt       826 acagcatttc ttaataaaat tgttaaaaag ct                                     858

<210> SEQ ID NO 43
<211> LENGTH: 171
<212> TYPE: PRT
<213> ORGANISM: Mus musculus

<400> SEQUENCE: 43

Met Asp Lys Ala Lys Lys Met Met Gln Ser Ile Pro Ser Phe Val Lys
1               5                   10                  15

Asp Thr Ser Asp Ile Glu Glu His Ala Leu Pro Ser Ala Gln Val Leu
                20                  25                  30

Pro Ala Gln Ser Thr Arg Cys Ser Asn Ser Glu Ala Leu Cys Leu Gly
            35                  40                  45

Lys Asp Gln Ser His Cys Ser Glu Asp Gly Trp Ile Ala Glu Trp Asp
        50                  55                  60

Leu Tyr Ser Phe Cys Val Phe Glu Ser Val Asp Tyr Leu Arg Ser Tyr
65                  70                  75                  80

Arg Arg Leu Asn Ser Ala Met Lys Lys Gly Thr Glu Val Phe Gln Ser
                85                  90                  95
```

```
Glu Ser Gln Arg Lys Pro Lys Val Ser Pro Gly Asp Val Glu Asn Tyr
                100                 105                 110

Lys Asp Lys Asp Thr Glu Lys Pro Asp Gln Pro Ser Pro Ser Leu Leu
            115                 120                 125

Arg Glu Lys Gly Leu Asp Leu Val Thr Cys Asp Gly Asp Cys Pro
        130                 135                 140

Val Arg Asp Pro Val Ser Asp Ser Ser Arg His Leu Gly Cys Trp Ala
145                 150                 155                 160

Trp Phe Gln Arg Ala Phe Gly His Lys Lys Lys
                165                 170

<210> SEQ ID NO 44
<211> LENGTH: 876
<212> TYPE: DNA
<213> ORGANISM: Mus musculus
<220> FEATURE:
<221> NAME/KEY: CDS
<222> LOCATION: (182)..(691)

<400> SEQUENCE: 44
```

| | |
|---|---:|
| agtctatact tcgctggcac tagagcccct tgcatgtgat tccatcttct attgaagacc | 60 |
| agctgaaaca tccatcctca ggaactgaga acttctggaa tcttggactt tacttcctct | 120 |
| ccagctgttg tggaataagt tcaactccag actgaggtgg aggatttacc ttcaggatc | 180 |

```
c atg gat aaa gcc aag aag atg atg cag tcc att ccc agt ttt gtc aag    229
  Met Asp Lys Ala Lys Lys Met Met Gln Ser Ile Pro Ser Phe Val Lys
   1               5                  10                  15 gat aca tca gat att gaa gaa cat gca ctg ccc agt gca cag gtc ttg    277
Asp Thr Ser Asp Ile Glu Glu His Ala Leu Pro Ser Ala Gln Val Leu
            20                  25                  30 cca gcc cag agt aca agg tgt tcc aat tct gag aca ctt tgt ttc agc    325
Pro Ala Gln Ser Thr Arg Cys Ser Asn Ser Glu Thr Leu Cys Phe Ser
        35                  40                  45 aaa gag caa agc cac tgc tct gag gat ggc tgg att gcc aat tgg gat    373
Lys Glu Gln Ser His Cys Ser Glu Asp Gly Trp Ile Ala Asn Trp Asp
    50                  55                  60 cta tac tcc ttt tgt gta ttt gag agt gtg gac tac ctg aaa tcc tac    421
Leu Tyr Ser Phe Cys Val Phe Glu Ser Val Asp Tyr Leu Lys Ser Tyr
65                  70                  75                  80 cgc aga ttg aat tct gcc atg aag aag ggc aca gag gtc ttc cag agt    469
Arg Arg Leu Asn Ser Ala Met Lys Lys Gly Thr Glu Val Phe Gln Ser
                85                  90                  95 gag agt cag agg gag cca caa gtg tcc cca gga gat gtg gaa aac tac    517
Glu Ser Gln Arg Glu Pro Gln Val Ser Pro Gly Asp Val Glu Asn Tyr
            100                 105                 110 aaa gac aaa gat aca gag gag cca gac caa ccc tca cta agc ttg ctc    565
Lys Asp Lys Asp Thr Glu Glu Pro Asp Gln Pro Ser Leu Ser Leu Leu
        115                 120                 125 agg gag aaa ggg ctg gaa ctt gtg acc tgt gat ggt gga gac tgc cct    613
Arg Glu Lys Gly Leu Glu Leu Val Thr Cys Asp Gly Gly Asp Cys Pro
    130                 135                 140 gac cag gat cct gca tct tat agt gcc agg cac cta ggc tgc tgg gca    661
Asp Gln Asp Pro Ala Ser Tyr Ser Ala Arg His Leu Gly Cys Trp Ala
145                 150                 155                 160 tgg ctt caa aga gct ttt cgc cag aag tga gaaagtcacc cagaactgtt       711
Trp Leu Gln Arg Ala Phe Arg Gln Lys
                165
```

| | |
|---|---:|
| tggatcccag attcctgcta agacttgcaa ttaggggatc ttctgtcagc tcctgctggt | 771 |
| acagcaaagg cacacaaagg cagttgtgtc ttttcagcca tctggtttgt gtttgtttgt | 831 |

```
ttgtttattt gtttgcagct ttcttaataa aattgttaaa aagct            876
```

<210> SEQ ID NO 45
<211> LENGTH: 169
<212> TYPE: PRT
<213> ORGANISM: Mus musculus

<400> SEQUENCE: 45

```
Met Asp Lys Ala Lys Lys Met Met Gln Ser Ile Pro Ser Phe Val Lys
1               5                   10                  15

Asp Thr Ser Asp Ile Glu Glu His Ala Leu Pro Ser Ala Gln Val Leu
            20                  25                  30

Pro Ala Gln Ser Thr Arg Cys Ser Asn Ser Glu Thr Leu Cys Phe Ser
        35                  40                  45

Lys Glu Gln Ser His Cys Ser Glu Asp Gly Trp Ile Ala Asn Trp Asp
    50                  55                  60

Leu Tyr Ser Phe Cys Val Phe Glu Ser Val Asp Tyr Leu Lys Ser Tyr
65                  70                  75                  80

Arg Arg Leu Asn Ser Ala Met Lys Lys Gly Thr Glu Val Phe Gln Ser
                85                  90                  95

Glu Ser Gln Arg Glu Pro Gln Val Ser Pro Gly Asp Val Glu Asn Tyr
            100                 105                 110

Lys Asp Lys Asp Thr Glu Glu Pro Asp Gln Pro Ser Leu Ser Leu Leu
        115                 120                 125

Arg Glu Lys Gly Leu Glu Leu Val Thr Cys Asp Gly Asp Cys Pro
    130                 135                 140

Asp Gln Asp Pro Ala Ser Tyr Ser Ala Arg His Leu Gly Cys Trp Ala
145                 150                 155                 160

Trp Leu Gln Arg Ala Phe Arg Gln Lys
                165
```

<210> SEQ ID NO 46
<211> LENGTH: 811
<212> TYPE: DNA
<213> ORGANISM: Mus musculus
<220> FEATURE:
<221> NAME/KEY: CDS
<222> LOCATION: (1)..(492)

<400> SEQUENCE: 46

```
atg gct gac aaa atg gac atg tca ttg gaa gac atc att aag ctg atc      48
Met Ala Asp Lys Met Asp Met Ser Leu Glu Asp Ile Ile Lys Leu Ile
1               5                   10                  15 ttg tca aat ctg cac ttc gga gtg tca gat gct gat att cag cta ctc      96
Leu Ser Asn Leu His Phe Gly Val Ser Asp Ala Asp Ile Gln Leu Leu
            20                  25                  30 ttt gct gaa ttt gga acg ttg aag aaa tct gct gtg cac tat gat cgc     144
Phe Ala Glu Phe Gly Thr Leu Lys Lys Ser Ala Val His Tyr Asp Arg
        35                  40                  45 tgt gga cga agt tta ggg aca gca cag gtg cac ttt gaa agg aaa gca     192
Cys Gly Arg Ser Leu Gly Thr Ala Gln Val His Phe Glu Arg Lys Ala
    50                  55                  60 gat gcc ctg aag gct atg aga gag tac aat ggc gcc cct ttg gat ggc     240
Asp Ala Leu Lys Ala Met Arg Glu Tyr Asn Gly Ala Pro Leu Asp Gly
65                  70                  75                  80 cgc cct atg aac atc cag ctt gcc acc tca cag att gat aga caa gga     288
Arg Pro Met Asn Ile Gln Leu Ala Thr Ser Gln Ile Asp Arg Gln Gly
                85                  90                  95 aga cct gca caa agc aaa aat agg ggc ggc atg aca aga aac cct ggc     336
Arg Pro Ala Gln Ser Lys Asn Arg Gly Gly Met Thr Arg Asn Pro Gly
```

```
tct gga gta tta agt ggt gga ggc acc aag aaa tgg aca ctt gga ggc      384
Ser Gly Val Leu Ser Gly Gly Gly Thr Lys Lys Trp Thr Leu Gly Gly
        115                 120                 125 agc cag gga aga ggg aga ggc acc atc agg aac tca aag cag cag cta      432
Ser Gln Gly Arg Gly Arg Gly Thr Ile Arg Asn Ser Lys Gln Gln Leu
130                 135                 140 tct gca gag gag ctg gat gcc cag ctg gat gct tat cag gaa atg atg      480
Ser Ala Glu Glu Leu Asp Ala Gln Leu Asp Ala Tyr Gln Glu Met Met
145                 150                 155                 160 gac acc agc tga acaattgagc aaagctgcac aagaacggaa cccatggcct          532
Asp Thr Ser ggtctgtgat gcctagactg agggttggct actggaccat gaacacaatg gtggattcct    592
cctttgcttc ttttgctttt ctcctgtttt aaaaccccat gtaaagttct ttctttctct    652
ccttctttct tttatttaca ttcagaaata cacctgtttt gtgctgagtt attttgtgga    712
taaattatag ttttttgcttt tgtgaagttg gcatttcac ctttgcccta ataaaattgt    772
gtgtagaaat aaacaagtat tctggagtca taaagtaat                           811

<210> SEQ ID NO 47
<211> LENGTH: 163
<212> TYPE: PRT
<213> ORGANISM: Mus musculus

<400> SEQUENCE: 47

Met Ala Asp Lys Met Asp Met Ser Leu Glu Asp Ile Ile Lys Leu Ile
1               5                   10                  15

Leu Ser Asn Leu His Phe Gly Val Ser Asp Ala Asp Ile Gln Leu Leu
            20                  25                  30

Phe Ala Glu Phe Gly Thr Leu Lys Lys Ser Ala Val His Tyr Asp Arg
        35                  40                  45

Cys Gly Arg Ser Leu Gly Thr Ala Gln Val His Phe Glu Arg Lys Ala
    50                  55                  60

Asp Ala Leu Lys Ala Met Arg Glu Tyr Asn Gly Ala Pro Leu Asp Gly
65                  70                  75                  80

Arg Pro Met Asn Ile Gln Leu Ala Thr Ser Gln Ile Asp Arg Gln Gly
                85                  90                  95

Arg Pro Ala Gln Ser Lys Asn Arg Gly Met Thr Arg Asn Pro Gly
            100                 105                 110

Ser Gly Val Leu Ser Gly Gly Gly Thr Lys Lys Trp Thr Leu Gly Gly
        115                 120                 125

Ser Gln Gly Arg Gly Arg Gly Thr Ile Arg Asn Ser Lys Gln Gln Leu
130                 135                 140

Ser Ala Glu Glu Leu Asp Ala Gln Leu Asp Ala Tyr Gln Glu Met Met
145                 150                 155                 160

Asp Thr Ser

<210> SEQ ID NO 48
<211> LENGTH: 2881
<212> TYPE: DNA
<213> ORGANISM: Mus musculus
<220> FEATURE:
<221> NAME/KEY: CDS
<222> LOCATION: (354)..(788)

<400> SEQUENCE: 48
ggaaaggggc gtggccggcc gttgcctagg aagggcgcgt cgtctctctg ctcgtccggc    60
```

```
tgtgacgggg aaggggtccc gctgcgtttt ggtcactact caggaggaga ccacaccttc      120
cggagaacca ggccagaacc gaagtactat tttgtagctc tcagaagcca ggactctgca      180
acactgtttg ctgcctgtgg atcttctata ttcacagtgt cccagttgct tctgatctac      240
cactgttaga tacttctgcc acccatccta agagtatagt tgttcttgga aaggagtctc      300
agctgctgtc agcaggagtc cctcattcga ctcctgtggt tgcccttcc atc atg        356
                                                          Met
                                                          1 cca aag aat aaa ggc aaa gga ggc aaa aac agg cgc aga ggt aaa aat      404
Pro Lys Asn Lys Gly Lys Gly Gly Lys Asn Arg Arg Arg Gly Lys Asn
        5                   10                  15 gaa aat gaa tct gag aaa aga gag ttg gtg ttt aaa gag gat ggg cag      452
Glu Asn Glu Ser Glu Lys Arg Glu Leu Val Phe Lys Glu Asp Gly Gln
        20                  25                  30 gag tat gct cag gtg atc aaa atg ctg gga aat gga cgg ttg gaa gca      500
Glu Tyr Ala Gln Val Ile Lys Met Leu Gly Asn Gly Arg Leu Glu Ala
    35                  40                  45 atg tgc ttt gac ggt gtg agg agg ctg tgc cat ata aga ggg aag ctg      548
Met Cys Phe Asp Gly Val Arg Arg Leu Cys His Ile Arg Gly Lys Leu
50              55                  60                  65 aga aaa aag gtt tgg ata aat acc tcg gac att ata ttg att ggt cta      596
Arg Lys Lys Val Trp Ile Asn Thr Ser Asp Ile Ile Leu Ile Gly Leu
                70                  75                  80 cga gac tat caa gat aac aaa gct gat gta atc tta aag tat aat gca      644
Arg Asp Tyr Gln Asp Asn Lys Ala Asp Val Ile Leu Lys Tyr Asn Ala
            85                  90                  95 gat gaa gca aga agt ctg aag gcc tgt gga gaa ctt cca gaa cat gcc      692
Asp Glu Ala Arg Ser Leu Lys Ala Cys Gly Glu Leu Pro Glu His Ala
        100                 105                 110 aaa atc aat gaa acg gac aca ttt ggt cct ggg gat gat gat gaa atc      740
Lys Ile Asn Glu Thr Asp Thr Phe Gly Pro Gly Asp Asp Asp Glu Ile
    115                 120                 125 caa ttt gat gat att gga gat gat gat gaa gac att gat gac atc tag      788
Gln Phe Asp Asp Ile Gly Asp Asp Asp Glu Asp Ile Asp Asp Ile
130                 135                 140 cctgacctaa gccatgctac cttccaagtt gtctgaagat agctccacac agtggcatct      848
tgaccttcat ctgttaagta aaacttcatg gcatgtgtat gacttgttaa tgcaaggtaa      908
tgaattttat ttttgaagt actatatttc tttgaaaacc aaagatgttg agttatcatc       968
ttaagtgaca tgttaacact ttgtgctttt gaatataatt gaacctagcg cacagcagtg     1028
agcactgtta agagactgcc tttccatttg tagcttcatt tctggcacgg gagtgttttg     1088
tgtcagcagt tctgccaggt ggccatcgtg aggctgaagt aagtcctagt ccagcacatc     1148
tgcttcaggc ctttgtactc tagtcatctg gctgcgttcg agacttctca gcagacttat     1208
agatgtgtac ggctgcactt ggagtcagac aagatatggc tactttgta cttatggagc      1268 catgccattt tatactttca cgttgtatac attcgtttga tcctttaagt tgttgccacc     1328
cataaaaagg catcttacag tgcagttttt aaattacatg ggtagcaatt ttgagttta      1388 aaaattagtc attgcagaaa ttaaatactt agaggagata atccattatc ttgactttag     1448
gaatataata gttgacaatg tttatatata atttacttc tctaaggcat acccaaaaat      1508
agaaaatgaa aaagagcagt gagtctgttc tgatgcttgc attgcataga gaagttttcc     1568
aacaaagcag ctgttaataa cacataaaat atgttttact ttgcaaagta ggttgtgtta     1628
agtcattttc aaaagttac ctactatatc gaggctctgg ataattacta tgtgttgatt     1688
aaagttagtt acagaattgt acaagctaag ttttccttaa actaagctta ggttaaaggg     1748
```

-continued

```
agaggagcca cagctcaatg aaaacacggt tcctgttttc taaatggagg cgcccagaaa  1808
cacaataaaa catgttggta caaaaacttt ttcttttaa tatgttcatt gtatctctgg  1868
tatataacaa aaataaatga ctgggtgatt tctggtatat catgagaggc ttttttttt   1928
ttttttaaa ttagactctg ggatttaaat gggacttaac tattttccca tttaaatgac   1988
gccagtattg gggtcctgca gcctaacccct gctgcttagg gagtgagtat aaaccgcgac  2048
tgtcagtcct cagatgcctt ccttttaaa gactagttct ttctcaggtc ttcttcttga   2108
cacctacaaa tggtgcctga ccacaagacg acagtattca tcttcacttt tattttttga   2168
ttgcttgttt tctagttaac ccagaataat atagcttatg aaaatctccc agtcaggaag   2228
aaagaaagaa agagaaagaa aagcaaatat gattttcctg atcattgatt ggtggatctc   2288
ttctagatgg agatatgtag atctttgtaa aggttaattt tataaagtga gagtagacat   2348
ggtacccaca cttagaagca gatcccacat ccccagaagg acagtgtgtg tttagaaaga   2408
acacatcact ggagctttt attgctctac acagtgtatc taaataagct gtcaactaca    2468
atttatccta ttgctgctgt aaattttttat gacagaaaga aaacctgacc atggaccagc  2528
tagcttgatg gccttcagca gcaaacaaga aactgtccaa gttaggaggt gaggactagt   2588
gcctgaagat gtcctctcag tccacaacat gtacaggtgc ccatacacac atcagcactc   2648
gcacaaagat gctctggagg ctatagtagt gtgtcttggt cattgcaaac catcagaggc   2708
aaaccctgag gtattcccat ttcctgtttc ctgcttgcag tgtctacatt tctctcccat    2768
tctaatgaag gaatgatcct tttataacat gagtgatttt atgctgttta tagaagtaaa   2828
tgttgacatg tgttagaatt aaaatgactt agagaacctg aaaaaaaaaa acc          2881
```

<210> SEQ ID NO 49
<211> LENGTH: 144
<212> TYPE: PRT
<213> ORGANISM: Mus musculus

<400> SEQUENCE: 49

```
Met Pro Lys Asn Lys Gly Lys Gly Gly Lys Asn Arg Arg Arg Gly Lys
1               5                   10                  15
Asn Glu Asn Glu Ser Glu Lys Arg Glu Leu Val Phe Lys Glu Asp Gly
                20                  25                  30
Gln Glu Tyr Ala Gln Val Ile Lys Met Leu Gly Asn Gly Arg Leu Glu
            35                  40                  45
Ala Met Cys Phe Asp Gly Val Arg Arg Leu Cys His Ile Arg Gly Lys
        50                  55                  60
Leu Arg Lys Lys Val Trp Ile Asn Thr Ser Asp Ile Ile Leu Ile Gly
65                  70                  75                  80
Leu Arg Asp Tyr Gln Asp Asn Lys Ala Asp Val Ile Leu Lys Tyr Asn
                85                  90                  95
Ala Asp Glu Ala Arg Ser Leu Lys Ala Cys Gly Glu Leu Pro Glu His
            100                 105                 110
Ala Lys Ile Asn Glu Thr Asp Thr Phe Gly Pro Gly Asp Asp Asp Glu
        115                 120                 125
Ile Gln Phe Asp Asp Ile Gly Asp Asp Glu Asp Ile Asp Ile
    130                 135                 140
```

<210> SEQ ID NO 50
<211> LENGTH: 1918
<212> TYPE: DNA
<213> ORGANISM: Mus musculus
<220> FEATURE:
<221> NAME/KEY: CDS

<222> LOCATION: (275)..(1918)

<400> SEQUENCE: 50

```
attttgctct cggcttgcta gctagtgtac tccttctctg gcatcagagc ctactctttt      60
gggattccag ctcttactga agaccagctg agacattgac tgagcaactt tggattcttg     120
gactttccat tcatagacag acgtcactgg attagcaaga gcccatccta atctttggga     180
gacctgaggt acttccaacc caaaggactg ggcttcagga tttgcaaaca tcagctgtca     240
gctccttgcc tagcccaagg aatcctttgc caca atg tcc tgt gtg cac tac aaa    295
                                    Met Ser Cys Val His Tyr Lys
                                      1               5
```

| | | | | | | | | | | | | | | | | |
|---|---|---|---|---|---|---|---|---|---|---|---|---|---|---|---|---|
| ttt | tcc | tct | aaa | ctc | agc | tac | aac | acc | atc | acc | ttt | gat | ggg | ctc | cat | 343 |
| Phe | Ser | Ser | Lys | Leu | Ser | Tyr | Asn | Thr | Ile | Thr | Phe | Asp | Gly | Leu | His | |
| | | 10 | | | | 15 | | | | 20 | | | | | | |

```
atc tcc ctc ttc tac tta aag aag cag att atg ggg aga gaa aag ctg    391
Ile Ser Leu Phe Tyr Leu Lys Lys Gln Ile Met Gly Arg Glu Lys Leu
         25                  30                  35 aaa act ggc aat agt gat ctg cag atc atc aat gca gag acg gaa gaa    439
Lys Thr Gly Asn Ser Asp Leu Gln Ile Ile Asn Ala Glu Thr Glu Glu
 40                  45                  50                  55 gaa tat act gac gat aat gcg ctc atc cct aag aat tca tct gtg att    487
Glu Tyr Thr Asp Asp Asn Ala Leu Ile Pro Lys Asn Ser Ser Val Ile
                 60                  65                  70 gtc aga aga att cct gtt gta ggt gtg aag tct aaa agc aag aca tat    535
Val Arg Arg Ile Pro Val Val Gly Val Lys Ser Lys Ser Lys Thr Tyr
 75                  80                  85 caa ata agt cac act aaa tca gtg atg gga act aca aga gca gtt aat    583
Gln Ile Ser His Thr Lys Ser Val Met Gly Thr Thr Arg Ala Val Asn
         90                  95                 100 gac tct tct gca ccg atg tct ctg gcc cag ctt ata gag act gcc aat    631
Asp Ser Ser Ala Pro Met Ser Leu Ala Gln Leu Ile Glu Thr Ala Asn
105                 110                 115 ctg gct gag gcc aat gct tca gag gaa gac aaa att aaa gca atg atg    679
Leu Ala Glu Ala Asn Ala Ser Glu Glu Asp Lys Ile Lys Ala Met Met
120                 125                 130                 135 ata caa tct ggc cat gaa tat gac cca atc aat tac atg aag aaa act    727
Ile Gln Ser Gly His Glu Tyr Asp Pro Ile Asn Tyr Met Lys Lys Thr
                140                 145                 150 cca gta ggc ttg cca cct cca tct tac acc tgc ttt cgt tgt ggt aaa    775
Pro Val Gly Leu Pro Pro Pro Ser Tyr Thr Cys Phe Arg Cys Gly Lys
                155                 160                 165 cct ggt cat tat act aag aat tgc cca aca agt gtg aat aag gac ttt    823
Pro Gly His Tyr Thr Lys Asn Cys Pro Thr Ser Val Asn Lys Asp Phe
        170                 175                 180 gaa tct tgt cct agg atc aga aag agc act gga att cct aga aat ttt    871
Glu Ser Cys Pro Arg Ile Arg Lys Ser Thr Gly Ile Pro Arg Asn Phe
185                 190                 195 atg atg gaa gtg aaa gat cct aac atg aaa ggt gca atg ctt aca aaa    919
Met Met Glu Val Lys Asp Pro Asn Met Lys Gly Ala Met Leu Thr Lys
200                 205                 210                 215 act ggg caa tat gca ata ccg act ata aat gca gag gcc tat gca att    967
Thr Gly Gln Tyr Ala Ile Pro Thr Ile Asn Ala Glu Ala Tyr Ala Ile
                220                 225                 230 ggg aag aaa agg aaa cca ccc ttc tta cca ggg gaa cct tca tca tca   1015
Gly Lys Lys Arg Lys Pro Pro Phe Leu Pro Gly Glu Pro Ser Ser Ser
                235                 240                 245 tct tca gaa gaa gtt ggt cct gtc cca gaa gag ctc ttg tgc ctc atc   1063
Ser Ser Glu Glu Val Gly Pro Val Pro Glu Glu Leu Leu Cys Leu Ile
250                 255                 260
```

```
tgc aag gac acc atg act gat gct gct atc atc ccc tgc tgt gga aac    1111
Cys Lys Asp Thr Met Thr Asp Ala Ala Ile Ile Pro Cys Cys Gly Asn
265                 270                 275 agt tac tgt gat gaa tgt ata aga aca gca ctt ctg gag tca gat gaa    1159
Ser Tyr Cys Asp Glu Cys Ile Arg Thr Ala Leu Leu Glu Ser Asp Glu
280                 285                 290                 295 cat aca tgt cca aca tgt cat caa aat gat gtt tct cct gat gct tta    1207
His Thr Cys Pro Thr Cys His Gln Asn Asp Val Ser Pro Asp Ala Leu
            300                 305                 310 gtt gcc aac aag gtt tta cga cag gct gtt aat aac ttt aaa aat caa    1255
Val Ala Asn Lys Val Leu Arg Gln Ala Val Asn Asn Phe Lys Asn Gln
        315                 320                 325 act ggc tat aca aag aga ctg caa aaa cag gtc act ctg tcc cct ccc    1303
Thr Gly Tyr Thr Lys Arg Leu Gln Lys Gln Val Thr Leu Ser Pro Pro
    330                 335                 340 cca cta cct cca cca agt gca ctc att cag cag aac ctg cag cct cct    1351
Pro Leu Pro Pro Pro Ser Ala Leu Ile Gln Gln Asn Leu Gln Pro Pro
345                 350                 355 atg aaa tct ccc aca tca aga caa cag gat cct ctg aag att cca gtg    1399
Met Lys Ser Pro Thr Ser Arg Gln Gln Asp Pro Leu Lys Ile Pro Val
360                 365                 370                 375 aca tcg tcc tca gct cac cca act ccc tct gta acc tca tta gct tca    1447
Thr Ser Ser Ser Ala His Pro Thr Pro Ser Val Thr Ser Leu Ala Ser
            380                 385                 390 aat cca tct tcc tcc gct cct tct gtg cct gga aac cca tct tct gcc    1495
Asn Pro Ser Ser Ser Ala Pro Ser Val Pro Gly Asn Pro Ser Ser Ala
        395                 400                 405 cca gct cca gta cct gat aca act gca aga gta tgt ata tca gtc cat    1543
Pro Ala Pro Val Pro Asp Thr Thr Ala Arg Val Cys Ile Ser Val His
    410                 415                 420 tca gaa aaa tca gat gga ccc ttt cgg gaa tca gaa aac aaa tta tta    1591
Ser Glu Lys Ser Asp Gly Pro Phe Arg Glu Ser Glu Asn Lys Leu Leu
425                 430                 435 cca gct act gcc ctt aca tca gaa cat tca aag gaa gcc tct tca att    1639
Pro Ala Thr Ala Leu Thr Ser Glu His Ser Lys Glu Ala Ser Ser Ile
440                 445                 450                 455 gct gtt act gct cct atg gaa gaa aag cgt ggc cag gtg cca gtc ctt    1687
Ala Val Thr Ala Pro Met Glu Glu Lys Arg Gly Gln Val Pro Val Leu
            460                 465                 470 gaa act cca cct ttg ttg gga cag tca tta tta tac aaa cag ttt atc    1735
Glu Thr Pro Pro Leu Leu Gly Gln Ser Leu Leu Tyr Lys Gln Phe Ile
        475                 480                 485 cct aca act ggt cca gta aga ata aat gct gct cat cca ggt ggt ggt    1783
Pro Thr Thr Gly Pro Val Arg Ile Asn Ala Ala His Pro Gly Gly Gly
    490                 495                 500 caa cca gat tgg gaa cat tcc aac aag cat ggc ttg cct ttc tcc atc    1831
Gln Pro Asp Trp Glu His Ser Asn Lys His Gly Leu Pro Phe Ser Ile
505                 510                 515 ttg ata tcc ctt gtg ttt ttt ggt ctg ggt gac tgt act gag gag ttt    1879
Leu Ile Ser Leu Val Phe Phe Gly Leu Gly Asp Cys Thr Glu Glu Phe
520                 525                 530                 535 gcc tct ttt gtc cct gga ttg tct cag atc tcc tgg tag                1918
Ala Ser Phe Val Pro Gly Leu Ser Gln Ile Ser Trp
            540                 545

<210> SEQ ID NO 51
<211> LENGTH: 547
<212> TYPE: PRT
<213> ORGANISM: Mus musculus

<400> SEQUENCE: 51
```

```
Met Ser Cys Val His Tyr Lys Phe Ser Ser Lys Leu Ser Tyr Asn Thr
1               5                   10                  15

Ile Thr Phe Asp Gly Leu His Ile Ser Leu Phe Tyr Leu Lys Lys Gln
            20                  25                  30

Ile Met Gly Arg Glu Lys Leu Lys Thr Gly Asn Ser Asp Leu Gln Ile
        35                  40                  45

Ile Asn Ala Glu Thr Glu Glu Tyr Thr Asp Asp Asn Ala Leu Ile
    50                  55                  60

Pro Lys Asn Ser Ser Val Ile Val Arg Arg Ile Pro Val Val Gly Val
65                  70                  75                  80

Lys Ser Lys Ser Lys Thr Tyr Gln Ile Ser His Thr Lys Ser Val Met
                85                  90                  95

Gly Thr Thr Arg Ala Val Asn Asp Ser Ser Ala Pro Met Ser Leu Ala
            100                 105                 110

Gln Leu Ile Glu Thr Ala Asn Leu Ala Glu Ala Asn Ala Ser Glu Glu
        115                 120                 125

Asp Lys Ile Lys Ala Met Met Ile Gln Ser Gly His Glu Tyr Asp Pro
    130                 135                 140

Ile Asn Tyr Met Lys Lys Thr Pro Val Gly Leu Pro Pro Ser Tyr
145                 150                 155                 160

Thr Cys Phe Arg Cys Gly Lys Pro Gly His Tyr Thr Lys Asn Cys Pro
            165                 170                 175

Thr Ser Val Asn Lys Asp Phe Glu Ser Cys Pro Arg Ile Arg Lys Ser
        180                 185                 190

Thr Gly Ile Pro Arg Asn Phe Met Met Glu Val Lys Asp Pro Asn Met
    195                 200                 205

Lys Gly Ala Met Leu Thr Lys Thr Gly Gln Tyr Ala Ile Pro Thr Ile
210                 215                 220

Asn Ala Glu Ala Tyr Ala Ile Gly Lys Lys Arg Lys Pro Pro Phe Leu
225                 230                 235                 240

Pro Gly Glu Pro Ser Ser Ser Ser Glu Val Gly Pro Val Pro
            245                 250                 255

Glu Glu Leu Leu Cys Leu Ile Cys Lys Asp Thr Met Thr Asp Ala Ala
        260                 265                 270

Ile Ile Pro Cys Cys Gly Asn Ser Tyr Cys Asp Glu Cys Ile Arg Thr
    275                 280                 285

Ala Leu Leu Glu Ser Asp Glu His Thr Cys Pro Thr Cys His Gln Asn
290                 295                 300

Asp Val Ser Pro Asp Ala Leu Val Ala Asn Lys Val Leu Arg Gln Ala
305                 310                 315                 320

Val Asn Asn Phe Lys Asn Gln Thr Gly Tyr Thr Lys Arg Leu Gln Lys
            325                 330                 335

Gln Val Thr Leu Ser Pro Pro Leu Pro Pro Ser Ala Leu Ile
        340                 345                 350

Gln Gln Asn Leu Gln Pro Pro Met Lys Ser Pro Thr Ser Arg Gln Gln
    355                 360                 365

Asp Pro Leu Lys Ile Pro Val Thr Ser Ser Ala His Pro Thr Pro
370                 375                 380

Ser Val Thr Ser Leu Ala Ser Asn Pro Ser Ser Ala Pro Ser Val
385                 390                 395                 400

Pro Gly Asn Pro Ser Ala Pro Ala Pro Val Pro Asp Thr Thr Ala
            405                 410                 415

Arg Val Cys Ile Ser Val His Ser Glu Lys Ser Asp Gly Pro Phe Arg
        420                 425                 430
```

```
Glu Ser Glu Asn Lys Leu Leu Pro Ala Thr Ala Leu Thr Ser Glu His
        435                 440                 445

Ser Lys Glu Ala Ser Ser Ile Ala Val Thr Ala Pro Met Glu Glu Lys
    450                 455                 460

Arg Gly Gln Val Pro Val Leu Glu Thr Pro Leu Leu Gly Gln Ser
465                 470                 475                 480

Leu Leu Tyr Lys Gln Phe Ile Pro Thr Thr Gly Pro Val Arg Ile Asn
            485                 490                 495

Ala Ala His Pro Gly Gly Gln Pro Asp Trp Glu His Ser Asn Lys
                500                 505                 510

His Gly Leu Pro Phe Ser Ile Leu Ile Ser Leu Val Phe Gly Leu
            515                 520                 525

Gly Asp Cys Thr Glu Glu Phe Ala Ser Phe Val Pro Gly Leu Ser Gln
    530                 535                 540

Ile Ser Trp
545

<210> SEQ ID NO 52
<211> LENGTH: 3680
<212> TYPE: DNA
<213> ORGANISM: Mus musculus
<220> FEATURE:
<221> NAME/KEY: CDS
<222> LOCATION: (606)..(2558)

<400> SEQUENCE: 52
agatcagctt tttcatctga aagcaacgag tctatcggat ccttgaggtg ggaggcaaag      60
aacgcgatta ttttagtgat cctcgctggg agaggtacag attcgtgggt cagacggagg     120
gacaatggat tcctgggcct ggaggttcca gacattccct aatcatttac cctttccaaa     180
gcactggaac cacactgacc ctgataccta ctaattggtt attgaagggg gtgtgcaagt     240
ctcagcctgt tttcacttcc agccagtctc tttcccatcg cccaacgtgt gattattgtt     300
ctgcttcctg gtagaagtc cctaacgagt ccctgttgg cctgggtgag tctcctcaac      360
aagcttcttt tctgagcagg aacacctttc taatgtggac attgcaggac aatcgctcgc     420
gaatcctaag tgcatgtgac cccaccttcc agcagcagag gacgtttctc ctcgctccag     480
agtgcttgga atatcttggt ggcaccttct gttaccagtg acaacctgtt gacactaaga     540
ggtctggaca ggatttcccg tcaccgcagc cataccacct attacatctc gattttctgt     600 gac ttt  atg cgc tcc ggt ctc tgc acg cct gca gag gca ttg gag atg cct     650
         Met Arg Ser Gly Leu Cys Thr Pro Ala Glu Ala Leu Glu Met Pro
          1               5                  10                  15 tct agc aca gag gcg gcg acc gat gaa tgt gac gat gcg gag ctc cgg     698
Ser Ser Thr Glu Ala Ala Thr Asp Glu Cys Asp Asp Ala Glu Leu Arg
                 20                  25                  30 tgc cgg gta gcc gtg gag gag ctg agt cct gga ggg caa cct cgc aag     746
Cys Arg Val Ala Val Glu Glu Leu Ser Pro Gly Gly Gln Pro Arg Lys
         35                  40                  45 cgc cag gcc ctg cgc gcc gca gag ctg agc cta ggt cga aac gaa cga     794
Arg Gln Ala Leu Arg Ala Ala Glu Leu Ser Leu Gly Arg Asn Glu Arg
     50                  55                  60 cgt gag tta atg ctg cga ctg cag gca ccg gga ccc acg ggg cgg cca     842
Arg Glu Leu Met Leu Arg Leu Gln Ala Pro Gly Pro Thr Gly Arg Pro
 65                  70                  75 cgc tgt ttc ccg cta cgc gcc gtg cgc ctc ttc acc cgc ttc gct gcg     890
Arg Cys Phe Pro Leu Arg Ala Val Arg Leu Phe Thr Arg Phe Ala Ala
 80                  85                  90                  95
```

```
act ggg cgc agc acg ttg cgg ctc ccc acc gat gga gtc cct gga gct    938
Thr Gly Arg Ser Thr Leu Arg Leu Pro Thr Asp Gly Val Pro Gly Ala
        100                 105                 110 ggc tca gtg caa ctg ctc ctc tcc gac tgt ccc ccg gag cgc ttg cgc    986
Gly Ser Val Gln Leu Leu Leu Ser Asp Cys Pro Pro Glu Arg Leu Arg
            115                 120                 125 cgc ttc ctg cgc acg ctg cgc ctg aag ctg gcg gtt gcc cct ggg ccg   1034
Arg Phe Leu Arg Thr Leu Arg Leu Lys Leu Ala Val Ala Pro Gly Pro
        130                 135                 140 gga ccc gcc tct gcc cgc gca cag ttg ctc ggc ccg cgg ccc cga gac   1082
Gly Pro Ala Ser Ala Arg Ala Gln Leu Leu Gly Pro Arg Pro Arg Asp
    145                 150                 155 ttt gtc acc atc agt cca gtg cag cca gag gaa ctg cag cgt gct gca   1130
Phe Val Thr Ile Ser Pro Val Gln Pro Glu Glu Leu Gln Arg Ala Ala
160                 165                 170                 175 gcc acc aag gct cca gat tct gcg ctg gaa aag cgg cca atg gaa tcc   1178
Ala Thr Lys Ala Pro Asp Ser Ala Leu Glu Lys Arg Pro Met Glu Ser
                180                 185                 190 cag act agt acg gaa gct cca agg tgg ccc ctg cct gtg aag aag ctg   1226
Gln Thr Ser Thr Glu Ala Pro Arg Trp Pro Leu Pro Val Lys Lys Leu
            195                 200                 205 cgc atg ccc tcc acc aaa ccg aag ctt tct gaa gag cag gcc gct gtg   1274
Arg Met Pro Ser Thr Lys Pro Lys Leu Ser Glu Glu Gln Ala Ala Val
        210                 215                 220 ctg agg atg gtt ctg aaa ggc cag agc att ttc ttc act ggg agc gca   1322
Leu Arg Met Val Leu Lys Gly Gln Ser Ile Phe Phe Thr Gly Ser Ala
    225                 230                 235 ggg aca gga aag tcc tac ctg ctg aaa cat atc ctg ggt tcc ctg ccc   1370
Gly Thr Gly Lys Ser Tyr Leu Leu Lys His Ile Leu Gly Ser Leu Pro
240                 245                 250                 255 cct act ggt act gtg gcc act gcc agc act ggg gtg gca gcc tgc cac   1418
Pro Thr Gly Thr Val Ala Thr Ala Ser Thr Gly Val Ala Ala Cys His
                260                 265                 270 att ggg ggc acc acc ctt cat gcc ttt gca ggc atc ggc tca ggc cag   1466
Ile Gly Gly Thr Thr Leu His Ala Phe Ala Gly Ile Gly Ser Gly Gln
            275                 280                 285 gct ccc ctg gcc cag tgc atg gcc ctg gcc aat cgg cca ggt gtg cgg   1514
Ala Pro Leu Ala Gln Cys Met Ala Leu Ala Asn Arg Pro Gly Val Arg
        290                 295                 300 cag ggc tgg ctg aac tgc caa cgt ttg gtc att gac gag atc tcc atg   1562
Gln Gly Trp Leu Asn Cys Gln Arg Leu Val Ile Asp Glu Ile Ser Met
    305                 310                 315 gtg gag gca gac ttc ttt gac aag ttg gaa gct gtg gcc aga gct gtc   1610
Val Glu Ala Asp Phe Phe Asp Lys Leu Glu Ala Val Ala Arg Ala Val
320                 325                 330                 335 cgg caa cag aag aag cca ttt gga ggg atc cag ctc atc atc tgt ggg   1658
Arg Gln Gln Lys Lys Pro Phe Gly Gly Ile Gln Leu Ile Ile Cys Gly
                340                 345                 350 gac ttc cta cag ttg cca cca gtg acc aaa ggc tcc cag cag cct cag   1706
Asp Phe Leu Gln Leu Pro Pro Val Thr Lys Gly Ser Gln Gln Pro Gln
            355                 360                 365 ttc tgc ttt cag gcc aag agc tgg agg agg tgt gtg cct gtg att ctg   1754
Phe Cys Phe Gln Ala Lys Ser Trp Arg Arg Cys Val Pro Val Ile Leu
        370                 375                 380 gag ctg act gag gtg tgg agg caa gca gac cag acc ttc atc tct cta   1802
Glu Leu Thr Glu Val Trp Arg Gln Ala Asp Gln Thr Phe Ile Ser Leu
    385                 390                 395 ctg cag gct gtg agg tta ggc aga tgt tca gat gaa gta acc cgc cag   1850
Leu Gln Ala Val Arg Leu Gly Arg Cys Ser Asp Glu Val Thr Arg Gln
400                 405                 410                 415
```

```
ctc agg gcc aca gct gcc cat aag gtg gga cga gat gga att gta gcc    1898
Leu Arg Ala Thr Ala Ala His Lys Val Gly Arg Asp Gly Ile Val Ala
            420                 425                 430 acg aga cta tgt acc cat cag gat gat gtg gcc ctg acc aac gag aag    1946
Thr Arg Leu Cys Thr His Gln Asp Asp Val Ala Leu Thr Asn Glu Lys
        435                 440                 445 tgg ctg aag gca ctg cca ggt gat gta cac agc ttt gag gct ata gac    1994
Trp Leu Lys Ala Leu Pro Gly Asp Val His Ser Phe Glu Ala Ile Asp
    450                 455                 460 agt gac cct gag cta agc cgg acc ctg gat gct cag tgc cct gtt agc    2042
Ser Asp Pro Glu Leu Ser Arg Thr Leu Asp Ala Gln Cys Pro Val Ser
465                 470                 475 cgt gtc ctt cag tta aag ctg ggg gct cag gtc atg ctg gtg aag aac    2090
Arg Val Leu Gln Leu Lys Leu Gly Ala Gln Val Met Leu Val Lys Asn
480                 485                 490                 495 ttg gca gtg tct cgg ggc ctg gtg aac ggt gcc cga ggg gtg gta gtt    2138
Leu Ala Val Ser Arg Gly Leu Val Asn Gly Ala Arg Gly Val Val Val
                500                 505                 510 ggg ttt gag tcc gaa ggg aga ggg ctc ccc cgg gta cgg ttc ctg tgt    2186
Gly Phe Glu Ser Glu Gly Arg Gly Leu Pro Arg Val Arg Phe Leu Cys
            515                 520                 525 ggt atc act gag gtc atc cgc act gac cgc tgg aca gta cag gtc act    2234
Gly Ile Thr Glu Val Ile Arg Thr Asp Arg Trp Thr Val Gln Val Thr
        530                 535                 540 ggg gga cag tac ctc agc cgg cag cag ctt ccc cta cag ctg gcc tgg    2282
Gly Gly Gln Tyr Leu Ser Arg Gln Gln Leu Pro Leu Gln Leu Ala Trp
    545                 550                 555 gcc ata tcc atc cac aaa agc cag ggc atg tct ctg gac tgt gtg gag    2330
Ala Ile Ser Ile His Lys Ser Gln Gly Met Ser Leu Asp Cys Val Glu
560                 565                 570                 575 atc tct ctg ggc cgt gtg ttt gcc agt ggt caa gcc tat gtg gcc ctc    2378
Ile Ser Leu Gly Arg Val Phe Ala Ser Gly Gln Ala Tyr Val Ala Leu
                580                 585                 590 tcc cgg gcc cgt agc ctc cag ggt ctt cgt gtg ctg gac ttt gac ccc    2426
Ser Arg Ala Arg Ser Leu Gln Gly Leu Arg Val Leu Asp Phe Asp Pro
            595                 600                 605 acg gtg gtt cga tgt gac tcc cga gtg ctg cat ttc tat gcc acc ctg    2474
Thr Val Val Arg Cys Asp Ser Arg Val Leu His Phe Tyr Ala Thr Leu
        610                 615                 620 cgg cag ggc agg ggc ctc agt ctg gag tcc caa gac gat gag gag gca    2522
Arg Gln Gly Arg Gly Leu Ser Leu Glu Ser Gln Asp Asp Glu Glu Ala
    625                 630                 635 aac tca gat ctg gag aac atg gac cca aac ctc tga cctcagctga         2568
Asn Ser Asp Leu Glu Asn Met Asp Pro Asn Leu
640                 645                 650 aagagaagac aaacttttag ctttttttcc tgggtcaagg ccctaggaat taactgggga  2628
gaggcctgtg tttcttccct tattcagcct ctggtagggt taagggacac agtttcccat  2688
ctacttaact agcattgcct cagtttcacc tatttccccg gggaaatgac ttccagggtt  2748
caaagctaga atggtgatg gttaccagag acaaagctc tctaccaagg gtggaacaca    2808
cagccacaga gttctttgca ggctggagag gcagtgcggg caggggctgc attcagcagc  2868
agcagcagta ggagcagcct gtcttattac accgcatgta tttattttgt gtgcttgtgc  2928
acgcacagca tattgtacat gtgaaggtca gaggacaact cgaggaagtt ggttttctct  2988
ttccccaagt gtgttctggg ggttaaattc aggtcacagg gcttggtagc aggcacttat  3048
acccgatgag caatcttgct accagggtcg gttctaattt tctttgtgtt attataacaa  3108
aatatataag gctgagtact ttatgaaaaa aatgatttat ttttaattaa tatatgctca  3168
```

-continued

```
cagttctaga agatgaagaa cacggaacca gcctcgtctc agctttgctg gggtttgacg    3228
gtagcagcaa ccgcctggcg gggacacttg caggcaggat catgagagac aggcacagag    3288
gatggtgatg ctggggaaga gtattaatcc gtccatgagg acaggacccc cttgctttag    3348
ttacctccca tgcaatccat ctctgaaagg ttacatcatc ttaacactgc tacgctaggg    3408
actaagcttc cagtacataa acctataagg gaaaccatcc aaactatggc aggagcctag    3468
aggggattca ggccagacac aagcccaaga tagaagttta attacccttca cagctgtgct    3528 cagcctagca cagccccaag taaacatcat tcagagcccg actgagaaca gacgctgcaa    3588
aatgtgctgg gtttagggga gaggccgtgt ttaggatacg gagatgtatg ttctcctttg    3648
tatttattta agccaaataa aactgtgaac cg    3680
```

<210> SEQ ID NO 53
<211> LENGTH: 650
<212> TYPE: PRT
<213> ORGANISM: Mus musculus

<400> SEQUENCE: 53

```
Met Arg Ser Gly Leu Cys Thr Pro Ala Glu Ala Leu Glu Met Pro Ser
1               5                   10                  15

Ser Thr Glu Ala Ala Thr Asp Glu Cys Asp Asp Ala Glu Leu Arg Cys
                20                  25                  30

Arg Val Ala Val Glu Glu Leu Ser Pro Gly Gly Gln Pro Arg Lys Arg
            35                  40                  45

Gln Ala Leu Arg Ala Ala Glu Leu Ser Leu Gly Arg Asn Glu Arg Arg
        50                  55                  60

Glu Leu Met Leu Arg Leu Gln Ala Pro Gly Pro Thr Gly Arg Pro Arg
65                  70                  75                  80

Cys Phe Pro Leu Arg Ala Val Arg Leu Phe Thr Arg Phe Ala Ala Thr
                85                  90                  95

Gly Arg Ser Thr Leu Arg Leu Pro Thr Asp Gly Val Pro Gly Ala Gly
                100                 105                 110

Ser Val Gln Leu Leu Leu Ser Asp Cys Pro Pro Glu Arg Leu Arg Arg
            115                 120                 125

Phe Leu Arg Thr Leu Arg Leu Lys Leu Ala Val Ala Pro Gly Pro Gly
        130                 135                 140

Pro Ala Ser Ala Arg Ala Gln Leu Leu Gly Pro Arg Pro Arg Asp Phe
145                 150                 155                 160

Val Thr Ile Ser Pro Val Gln Pro Glu Glu Leu Gln Arg Ala Ala Ala
                165                 170                 175

Thr Lys Ala Pro Asp Ser Ala Leu Glu Lys Arg Pro Met Glu Ser Gln
                180                 185                 190

Thr Ser Thr Glu Ala Pro Arg Trp Pro Leu Pro Val Lys Lys Leu Arg
            195                 200                 205

Met Pro Ser Thr Lys Pro Lys Leu Ser Glu Glu Gln Ala Ala Val Leu
        210                 215                 220

Arg Met Val Leu Lys Gly Gln Ser Ile Phe Phe Thr Gly Ser Ala Gly
225                 230                 235                 240

Thr Gly Lys Ser Tyr Leu Leu Lys His Ile Leu Gly Ser Leu Pro Pro
                245                 250                 255

Thr Gly Thr Val Ala Thr Ala Ser Thr Gly Val Ala Ala Cys His Ile
                260                 265                 270

Gly Gly Thr Thr Leu His Ala Phe Ala Gly Ile Gly Ser Gly Gln Ala
            275                 280                 285
```

```
Pro Leu Ala Gln Cys Met Ala Leu Ala Asn Arg Pro Gly Val Arg Gln
        290                 295                 300

Gly Trp Leu Asn Cys Gln Arg Leu Val Ile Asp Glu Ile Ser Met Val
305                 310                 315                 320

Glu Ala Asp Phe Phe Asp Lys Leu Glu Ala Val Ala Arg Ala Val Arg
                325                 330                 335

Gln Gln Lys Lys Pro Phe Gly Ile Gln Leu Ile Ile Cys Gly Asp
            340                 345                 350

Phe Leu Gln Leu Pro Pro Val Thr Lys Gly Ser Gln Pro Gln Phe
        355                 360                 365

Cys Phe Gln Ala Lys Ser Trp Arg Arg Cys Val Pro Val Ile Leu Glu
    370                 375                 380

Leu Thr Glu Val Trp Arg Gln Ala Asp Gln Thr Phe Ile Ser Leu Leu
385                 390                 395                 400

Gln Ala Val Arg Leu Gly Arg Cys Ser Asp Glu Val Thr Arg Gln Leu
                405                 410                 415

Arg Ala Thr Ala Ala His Lys Val Gly Arg Asp Gly Ile Val Ala Thr
            420                 425                 430

Arg Leu Cys Thr His Gln Asp Asp Val Ala Leu Thr Asn Glu Lys Trp
        435                 440                 445

Leu Lys Ala Leu Pro Gly Asp Val His Ser Phe Glu Ala Ile Asp Ser
450                 455                 460

Asp Pro Glu Leu Ser Arg Thr Leu Asp Ala Gln Cys Pro Val Ser Arg
465                 470                 475                 480

Val Leu Gln Leu Lys Leu Gly Ala Gln Val Met Leu Val Lys Asn Leu
                485                 490                 495

Ala Val Ser Arg Gly Leu Val Asn Gly Ala Arg Gly Val Val Val Gly
            500                 505                 510

Phe Glu Ser Glu Gly Arg Gly Leu Pro Arg Val Arg Phe Leu Cys Gly
        515                 520                 525

Ile Thr Glu Val Ile Arg Thr Asp Arg Trp Thr Val Gln Val Thr Gly
        530                 535                 540

Gly Gln Tyr Leu Ser Arg Gln Gln Leu Pro Leu Gln Leu Ala Trp Ala
545                 550                 555                 560

Ile Ser Ile His Lys Ser Gln Gly Met Ser Leu Asp Cys Val Glu Ile
                565                 570                 575

Ser Leu Gly Arg Val Phe Ala Ser Gly Gln Ala Tyr Val Ala Leu Ser
            580                 585                 590

Arg Ala Arg Ser Leu Gln Gly Leu Arg Val Leu Asp Phe Asp Pro Thr
        595                 600                 605

Val Val Arg Cys Asp Ser Arg Val Leu His Phe Tyr Ala Thr Leu Arg
610                 615                 620

Gln Gly Arg Gly Leu Ser Leu Glu Ser Gln Asp Asp Glu Ala Asn
625                 630                 635                 640

Ser Asp Leu Glu Asn Met Asp Pro Asn Leu
                645                 650

<210> SEQ ID NO 54
<211> LENGTH: 19
<212> TYPE: DNA
<213> ORGANISM: Artificial
<220> FEATURE:
<223> OTHER INFORMATION: Synthetic oligonucleotide

<400> SEQUENCE: 54
gtagcgatat gaggagatt                                              19
```

```
<210> SEQ ID NO 55
<211> LENGTH: 19
<212> TYPE: DNA
<213> ORGANISM: Artificial
<220> FEATURE:
<223> OTHER INFORMATION: Synthetic oligonucleotide

<400> SEQUENCE: 55
gaccaacaat ttagagttt                                               19

<210> SEQ ID NO 56
<211> LENGTH: 19
<212> TYPE: DNA
<213> ORGANISM: Artificial
<220> FEATURE:
<223> OTHER INFORMATION: Synthetic oligonucleotide

<400> SEQUENCE: 56
caccaagtgc tcagctaaa                                               19

<210> SEQ ID NO 57
<211> LENGTH: 19
<212> TYPE: DNA
<213> ORGANISM: Artificial
<220> FEATURE:
<223> OTHER INFORMATION: Synthetic oligonucleotide

<400> SEQUENCE: 57
gctgcaaagt ctctggaag                                               19

<210> SEQ ID NO 58
<211> LENGTH: 25
<212> TYPE: DNA
<213> ORGANISM: Artificial
<220> FEATURE:
<223> OTHER INFORMATION: Synthetic oligonucleotide

<400> SEQUENCE: 58
ccagtggtag cgatatgagg agatt                                        25

<210> SEQ ID NO 59
<211> LENGTH: 19
<212> TYPE: DNA
<213> ORGANISM: Artificial
<220> FEATURE:
<223> OTHER INFORMATION: Synthetic oligonucleotide

<400> SEQUENCE: 59
gagtgaattg ctttgtgtc                                               19

<210> SEQ ID NO 60
<211> LENGTH: 1848
<212> TYPE: DNA
<213> ORGANISM: Mus musculus
<220> FEATURE:
<221> NAME/KEY: misc_feature
<222> LOCATION: (45)..(45)
<223> OTHER INFORMATION: n = C or T
<220> FEATURE:
<221> NAME/KEY: misc_feature
<222> LOCATION: (49)..(49)
<223> OTHER INFORMATION: n = C or G
<220> FEATURE:
<221> NAME/KEY: misc_feature
<222> LOCATION: (54)..(54)
<223> OTHER INFORMATION: n = C or A
<220> FEATURE:
<221> NAME/KEY: misc_feature
```

```
<222> LOCATION: (55)..(55)
<223> OTHER INFORMATION: n = A or G
<220> FEATURE:
<221> NAME/KEY: misc_feature
<222> LOCATION: (69)..(69)
<223> OTHER INFORMATION: n = A or G
<220> FEATURE:
<221> NAME/KEY: misc_feature
<222> LOCATION: (81)..(81)
<223> OTHER INFORMATION: n = T or C
<220> FEATURE:
<221> NAME/KEY: misc_feature
<222> LOCATION: (96)..(96)
<223> OTHER INFORMATION: n = T or G
<220> FEATURE:
<221> NAME/KEY: misc_feature
<222> LOCATION: (139)..(139)
<223> OTHER INFORMATION: n = A or G
<220> FEATURE:
<221> NAME/KEY: misc_feature
<222> LOCATION: (159)..(159)
<223> OTHER INFORMATION: n = T or C
<220> FEATURE:
<221> NAME/KEY: misc_feature
<222> LOCATION: (166)..(166)
<223> OTHER INFORMATION: n = G or A
<220> FEATURE:
<221> NAME/KEY: misc_feature
<222> LOCATION: (261)..(261)
<223> OTHER INFORMATION: n = T or A
<220> FEATURE:
<221> NAME/KEY: misc_feature
<222> LOCATION: (264)..(264)
<223> OTHER INFORMATION: n = C or G
<220> FEATURE:
<221> NAME/KEY: misc_feature
<222> LOCATION: (286)..(286)
<223> OTHER INFORMATION: n = C or T
<220> FEATURE:
<221> NAME/KEY: misc_feature
<222> LOCATION: (329)..(329)
<223> OTHER INFORMATION: n = C or T
<220> FEATURE:
<221> NAME/KEY: misc_feature
<222> LOCATION: (463)..(463)
<223> OTHER INFORMATION: n = C or T
<220> FEATURE:
<221> NAME/KEY: misc_feature
<222> LOCATION: (494)..(494)
<223> OTHER INFORMATION: n = A or T
<220> FEATURE:
<221> NAME/KEY: misc_feature
<222> LOCATION: (605)..(605)
<223> OTHER INFORMATION: n = C or T
<220> FEATURE:
<221> NAME/KEY: misc_feature
<222> LOCATION: (839)..(839)
<223> OTHER INFORMATION: n = C or G
<220> FEATURE:
<221> NAME/KEY: misc_feature
<222> LOCATION: (883)..(883)
<223> OTHER INFORMATION: n = T or G
<220> FEATURE:
<221> NAME/KEY: misc_feature
<222> LOCATION: (895)..(895)
<223> OTHER INFORMATION: n = T or A
<220> FEATURE:
<221> NAME/KEY: misc_feature
<222> LOCATION: (898)..(898)
<223> OTHER INFORMATION: n = G or A
<220> FEATURE:
<221> NAME/KEY: misc_feature
<222> LOCATION: (922)..(922)
<223> OTHER INFORMATION: n = C or A
<220> FEATURE:
<221> NAME/KEY: misc_feature
<222> LOCATION: (924)..(924)
<223> OTHER INFORMATION: n = C or T
<220> FEATURE:
<221> NAME/KEY: misc_feature
```

```
-continued

<222> LOCATION: (946)..(946)
<223> OTHER INFORMATION: n = C or G
<220> FEATURE:
<221> NAME/KEY: misc_feature
<222> LOCATION: (960)..(960)
<223> OTHER INFORMATION: n = C or A
<220> FEATURE:
<221> NAME/KEY: misc_feature
<222> LOCATION: (965)..(965)
<223> OTHER INFORMATION: n = C or G
<220> FEATURE:
<221> NAME/KEY: misc_feature
<222> LOCATION: (1049)..(1049)
<223> OTHER INFORMATION: n = A or G
<220> FEATURE:
<221> NAME/KEY: misc_feature
<222> LOCATION: (1073)..(1073)
<223> OTHER INFORMATION: n = A or T
<220> FEATURE:
<221> NAME/KEY: misc_feature
<222> LOCATION: (1074)..(1074)
<223> OTHER INFORMATION: n = A or G
<220> FEATURE:
<221> NAME/KEY: misc_feature
<222> LOCATION: (1094)..(1094)
<223> OTHER INFORMATION: n = A or C
<220> FEATURE:
<221> NAME/KEY: misc_feature
<222> LOCATION: (1098)..(1098)
<223> OTHER INFORMATION: n = A or T
<220> FEATURE:
<221> NAME/KEY: misc_feature
<222> LOCATION: (1111)..(1111)
<223> OTHER INFORMATION: n = C or T
<220> FEATURE:
<221> NAME/KEY: misc_feature
<222> LOCATION: (1134)..(1134)
<223> OTHER INFORMATION: n = C or T
<220> FEATURE:
<221> NAME/KEY: misc_feature
<222> LOCATION: (1147)..(1147)
<223> OTHER INFORMATION: n = A or T
<220> FEATURE:
<221> NAME/KEY: misc_feature
<222> LOCATION: (1212)..(1212)
<223> OTHER INFORMATION: n = C or T
<220> FEATURE:
<221> NAME/KEY: misc_feature
<222> LOCATION: (1247)..(1247)
<223> OTHER INFORMATION: n = C or A
<220> FEATURE:
<221> NAME/KEY: misc_feature
<222> LOCATION: (1253)..(1253)
<223> OTHER INFORMATION: n = T or A
<220> FEATURE:
<221> NAME/KEY: misc_feature
<222> LOCATION: (1260)..(1260)
<223> OTHER INFORMATION: n = G or C
<220> FEATURE:
<221> NAME/KEY: misc_feature
<222> LOCATION: (1272)..(1272)
<223> OTHER INFORMATION: n = G or C
<220> FEATURE:
<221> NAME/KEY: misc_feature
<222> LOCATION: (1287)..(1287)
<223> OTHER INFORMATION: n = G or C
<220> FEATURE:
<221> NAME/KEY: misc_feature
<222> LOCATION: (1291)..(1291)
<223> OTHER INFORMATION: n = T or C
<220> FEATURE:
<221> NAME/KEY: misc_feature
<222> LOCATION: (1308)..(1308)
<223> OTHER INFORMATION: n = T or C
<220> FEATURE:
<221> NAME/KEY: misc_feature
<222> LOCATION: (1320)..(1320)
<223> OTHER INFORMATION: n = A or G
<220> FEATURE:
<221> NAME/KEY: misc_feature
```

```
<222> LOCATION: (1365)..(1365)
<223> OTHER INFORMATION: n = T or C
<220> FEATURE:
<221> NAME/KEY: misc_feature
<222> LOCATION: (1384)..(1384)
<223> OTHER INFORMATION: n = T or A
<220> FEATURE:
<221> NAME/KEY: misc_feature
<222> LOCATION: (1433)..(1433)
<223> OTHER INFORMATION: n = G or A
<220> FEATURE:
<221> NAME/KEY: misc_feature
<222> LOCATION: (1723)..(1723)
<223> OTHER INFORMATION: n = G or C

<400> SEQUENCE: 60
```

| | | | | | |
|---|---|---|---|---|---|
| cacagtgcct | ccctgggctt | cttggcatca | cccttgaagt | tcacnggana | aagnngtgag | 60 |
| gtggaggant | aggtaaactt | nccttcctag | tggtcntgaa | tgtctttac | agtacatcca | 120 |
| tcaactgtta | gcattttcnt | aaagtcacaa | aacagatant | aaactnctat | agttgaatct | 180 |
| ttcacaccat | tgtcaccaca | atggcttcac | agcaggcacc | agcaaaagac | cttcagacca | 240 |
| acaatttaga | gtttactcca | nctnatagtt | ctggtgtgca | gtgggnagaa | gacatctcta | 300 |
| actcaccaag | tgctcagcta | aacttttcnc | caagtaacaa | tggctgctgg | gcaactcagg | 360 |
| agctgcaaag | tctctggaag | atgttcaact | cctggttgca | gccagaaaag | cagactaagg | 420 |
| agcagatgat | ttctcaactg | tcttggagc | agtttctcct | cantgggcac | tgcaaggaca | 480 |
| agtatgcttt | gacngagaag | tggaaagcca | gtggtagcga | tatgaggaga | ttcatggaga | 540 |
| gtctgactga | tgagtgcttg | aagcctcctg | tcatggtcca | tgtttcaatg | caaggacaag | 600 |
| aagcnctctt | ttctgaaaac | atgccattaa | agaagtcat | caagcttttg | aaacaacagc | 660 |
| aatctgcaac | aaggccaaca | ccagataatg | agcagatgcc | agtagacacc | acacaagata | 720 |
| gattattggc | cacaggacaa | gaaaacagtg | aaaatgaatg | caacaactct | tgtaatgcta | 780 |
| ctgaagcaaa | tgttggtgaa | agctgtagtg | gaaatgaaat | ggactccctt | cttattatnc | 840 |
| agaaagaaca | gcaccctgag | catgaagagg | ggaatgttgt | ttntcaattc | cctcntgntg | 900 |
| ccagaagagc | aagtcaaggc | ancnccagtc | atcatgtaga | cttccngagt | gctccgactn | 960 |
| ctgcngatgt | ccccatggag | gaacaaccaa | aggatttatc | cagagaaaac | atctctgagg | 1020 |
| acaagaacaa | ttgctataac | acttccagna | atgcagctac | tcaagtatat | agnngtgata | 1080 |
| atattcccag | gaanaagnca | gactcccttt | ncattaacaa | gagaatatat | catnctgagc | 1140 |
| ctgaggnggg | agatattcct | tatggagttc | ctcaggattc | tacaagagca | agtcaaggaa | 1200 |
| catctacatg | cntgcaagag | tcacttgggg | aatgttttc | tgaaaangac | ccnagggagn | 1260 |
| taccagggtt | gnagtctagg | caagagnagc | ntatctctga | tcctgtcntt | cttggtaagn | 1320 |
| atcatgaggc | aaacttacca | tgtgaaagtc | atcaaaagag | attcngtaga | gatgccaaac | 1380 |
| tatncaagtg | tgaagaatgt | tctaggatgt | tcaaacatgc | caggagcctt | tcntcccacc | 1440 |
| agagaactca | cctgaataag | aagagtgaat | tgctttgtgt | cacctgtcag | aaaatgttca | 1500 |
| aacgagtctc | tgaccgccga | acccatgaga | tcatacacat | gccagaaaag | cctttcaagt | 1560 |
| gcagcacatg | tgaaaagtcc | ttcagccaca | agaccaacct | gaagtctcat | gagatgattc | 1620 |
| acacaggaga | aatgccttat | gtctgttccc | tatgtagccg | tcgctttcgc | caatcatcca | 1680 |
| cttaccatcg | tcacctgagg | aattaccaca | gatctgactg | aantatctaa | catcctcagc | 1740 |
| agagactggt | agggcttcag | cctcagtatg | tcatcttcaa | agagagaaga | atgttgcaag | 1800 |
| taaattgtac | tgtcccaata | atgatataac | atgcttgtgg | attgccac | | 1848 |